US011752348B2

(12) United States Patent
Blum et al.

(10) Patent No.: US 11,752,348 B2
(45) Date of Patent: *Sep. 12, 2023

(54) SYSTEMS AND METHODS FOR CLOSED-LOOP DETERMINATION OF STIMULATION PARAMETER SETTINGS FOR AN ELECTRICAL SIMULATION SYSTEM

(71) Applicant: Boston Scientific Neuromodulation Corporation, Valencia, CA (US)

(72) Inventors: David Blum, Boston, MA (US); Sherry Lin, Sherman Oaks, CA (US); Hemant Bokil, Cambridge, MA (US); Michael A. Moffitt, Solon, OH (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 695 days.

This patent is subject to a terminal disclaimer.

(21) Appl. No.: 16/748,161

(22) Filed: Jan. 21, 2020

(65) Prior Publication Data

US 2020/0155859 A1 May 21, 2020

Related U.S. Application Data

(63) Continuation of application No. 15/783,961, filed on Oct. 13, 2017, now Pat. No. 10,603,498.
(Continued)

(51) Int. Cl.
*A61N 1/372* (2006.01)
*A61N 1/36* (2006.01)
(Continued)

(52) U.S. Cl.
CPC ......... *A61N 1/37247* (2013.01); *A61N 1/025* (2013.01); *A61N 1/36125* (2013.01);
(Continued)

(58) Field of Classification Search
CPC ................ A61N 1/37247; A61N 1/025; A61N 1/36125; A61N 1/36132; A61N 1/36139;
(Continued)

(56) References Cited

U.S. PATENT DOCUMENTS 3,999,555 A 12/1976 Person
4,144,889 A 3/1979 Tyers et al.
(Continued)

FOREIGN PATENT DOCUMENTS

EP 1048320 11/2000
EP 1166819 1/2002
(Continued)

OTHER PUBLICATIONS

Nowinski, W. L., et al., "Statistical analysis of 168 bilateral subthalamic nucleus implantations by means of the probabilistic functional atlas.", Neurosurgery 57(4 Suppl) (Oct. 2005), 319-30.
(Continued)

*Primary Examiner* — Lindsey G Wehrheim
(74) *Attorney, Agent, or Firm* — Branch Partners PLLC; Bruce E. Black

(57) ABSTRACT

A method or system for facilitating the determining and setting of stimulation parameters for programming an electrical stimulation system using closed loop programming is provided. For example, pulse generator feedback logic is executed by a processor to interface with control instructions of an implantable pulse generator by incorporating one or more machine learning engines to automatically generate a proposed set of stimulation parameter values that each affect a stimulation aspect of the implantable pulse generator, receive one or more clinical responses and automatically generate a revised set of values taking into account the received clinical responses, and repeating the automated receiving of a clinical response and adjusting the stimulation
(Continued)

parameter values taking the clinical response into account, until or unless a stop condition is reach or the a therapeutic response is indicated within a designated tolerance.

20 Claims, 20 Drawing Sheets

Related U.S. Application Data

(60) Provisional application No. 62/545,819, filed on Aug. 15, 2017, provisional application No. 62/408,620, filed on Oct. 14, 2016.

(51) Int. Cl.
*A61N 1/02* (2006.01)
*A61N 1/05* (2006.01)

(52) U.S. Cl.
CPC ..... *A61N 1/36132* (2013.01); *A61N 1/36139* (2013.01); *A61N 1/0534* (2013.01); *A61N 1/0551* (2013.01); *A61N 1/37241* (2013.01)

(58) Field of Classification Search
CPC . A61N 1/0534; A61N 1/0551; A61N 1/37241
See application file for complete search history.

(56) References Cited

U.S. PATENT DOCUMENTS

| | | |
|---|---|---|
| 4,177,818 A | 12/1979 | De Pedro |
| 4,341,221 A | 7/1982 | Testerman |
| 4,378,797 A | 4/1983 | Osterholm |
| 4,445,500 A | 5/1984 | Osterholm |
| 4,735,208 A | 4/1988 | Wyler et al. |
| 4,765,341 A | 8/1988 | Mower et al. |
| 4,841,973 A | 6/1989 | Stecker |
| 5,067,495 A | 11/1991 | Brehm |
| 5,099,846 A | 3/1992 | Hardy |
| 5,222,494 A | 6/1993 | Baker, Jr. |
| 5,255,693 A | 10/1993 | Dutcher et al. |
| 5,259,387 A | 11/1993 | dePinto |
| 5,304,206 A | 4/1994 | Baker, Jr. et al. |
| 5,344,438 A | 9/1994 | Testerman et al. |
| 5,361,763 A | 11/1994 | Kao et al. |
| 5,452,407 A | 9/1995 | Crook |
| 5,560,360 A | 10/1996 | Filler et al. |
| 5,565,949 A | 10/1996 | Kasha, Jr. |
| 5,593,427 A | 1/1997 | Gliner et al. |
| 5,601,612 A | 2/1997 | Gliner et al. |
| 5,607,454 A | 3/1997 | Cameron et al. |
| 5,620,470 A | 4/1997 | Gliner et al. |
| 5,651,767 A | 7/1997 | Schulmann |
| 5,711,316 A | 1/1998 | Elsberry et al. |
| 5,713,922 A | 2/1998 | King |
| 5,716,377 A | 2/1998 | Rise et al. |
| 5,724,985 A | 3/1998 | Snell et al. |
| 5,749,904 A | 5/1998 | Gliner et al. |
| 5,749,905 A | 5/1998 | Gliner et al. |
| 5,776,170 A | 7/1998 | MacDonald et al. |
| 5,782,762 A | 7/1998 | Vining |
| 5,843,148 A | 12/1998 | Gijsbers et al. |
| 5,859,922 A | 1/1999 | Hoffmann |
| 5,868,740 A | 2/1999 | LeVeen et al. |
| 5,897,583 A | 4/1999 | Meyer et al. |
| 5,910,804 A | 6/1999 | Fortenbery et al. |
| 5,925,070 A | 7/1999 | King et al. |
| 5,938,688 A | 8/1999 | Schiff |
| 5,938,690 A | 8/1999 | Law et al. |
| 5,978,713 A | 11/1999 | Prutchi et al. |
| 6,016,449 A | 1/2000 | Fischell et al. |
| 6,029,090 A | 2/2000 | Herbst |
| 6,029,091 A | 2/2000 | de la Rama et al. |
| 6,050,992 A | 4/2000 | Nichols |
| 6,058,331 A | 5/2000 | King |
| 6,066,163 A | 5/2000 | John |
| 6,083,162 A | 7/2000 | Vining |
| 6,094,598 A | 7/2000 | Elsberry et al. |
| 6,096,756 A | 8/2000 | Crain et al. |
| 6,106,460 A | 8/2000 | Panescu et al. |
| 6,109,269 A | 8/2000 | Rise et al. |
| 6,128,538 A | 10/2000 | Fischell et al. |
| 6,129,685 A | 10/2000 | Howard, III |
| 6,146,390 A | 11/2000 | Heilbrun et al. |
| 6,161,044 A | 12/2000 | Silverstone |
| 6,167,311 A | 12/2000 | Rezai |
| 6,181,969 B1 | 1/2001 | Gord |
| 6,192,266 B1 | 2/2001 | Dupree et al. |
| 6,205,361 B1 | 3/2001 | Kuzma |
| 6,208,881 B1 | 3/2001 | Champeau |
| 6,240,308 B1 | 5/2001 | Hardy et al. |
| 6,246,912 B1 | 6/2001 | Sluijter et al. |
| 6,253,109 B1 | 6/2001 | Gielen |
| 6,289,239 B1 | 9/2001 | Panescu et al. |
| 6,301,492 B1 | 10/2001 | Zonenshayn |
| 6,310,619 B1 | 10/2001 | Rice |
| 6,319,241 B1 | 11/2001 | King |
| 6,336,899 B1 | 1/2002 | Yamazaki |
| 6,343,226 B1 | 1/2002 | Sunde et al. |
| 6,351,675 B1 | 2/2002 | Tholen et al. |
| 6,353,762 B1 | 3/2002 | Baudino et al. |
| 6,366,813 B1 | 4/2002 | Dilorenzo |
| 6,368,331 B1 | 4/2002 | Front et al. |
| 6,389,311 B1 | 5/2002 | Whayne et al. |
| 6,393,325 B1 | 5/2002 | Mann et al. |
| 6,421,566 B1 | 7/2002 | Holsheimer |
| 6,435,878 B1 | 8/2002 | Reynolds et al. |
| 6,442,432 B2 | 8/2002 | Lee |
| 6,463,328 B1 | 10/2002 | John |
| 6,491,699 B1 | 12/2002 | Henderson et al. |
| 6,494,831 B1 | 12/2002 | Koritzinsky |
| 6,507,759 B1 | 1/2003 | Prutchi et al. |
| 6,510,347 B2 | 1/2003 | Borkan |
| 6,516,227 B1 | 2/2003 | Meadows et al. |
| 6,517,480 B1 | 2/2003 | Krass |
| 6,539,263 B1 | 3/2003 | Schiff et al. |
| 6,560,490 B2 | 5/2003 | Grill et al. |
| 6,579,280 B1 | 6/2003 | Kovach et al. |
| 6,600,956 B2 | 7/2003 | Maschino et al. |
| 6,606,523 B1 | 8/2003 | Jenkins |
| 6,609,029 B1 | 8/2003 | Mann et al. |
| 6,609,031 B1 | 8/2003 | Law et al. |
| 6,609,032 B1 | 8/2003 | Woods et al. |
| 6,622,048 B1 | 9/2003 | Mann et al. |
| 6,631,297 B1 | 10/2003 | Mo |
| 6,654,642 B2 | 11/2003 | North et al. |
| 6,662,053 B2 | 12/2003 | Borkan |
| 6,675,046 B2 | 1/2004 | Holsheimer |
| 6,684,106 B2 | 1/2004 | Herbst |
| 6,687,392 B1 | 2/2004 | Touzawa et al. |
| 6,690,972 B2 | 2/2004 | Conley et al. |
| 6,690,974 B2 | 2/2004 | Archer et al. |
| 6,692,315 B1 | 2/2004 | Soumillion et al. |
| 6,694,162 B2 | 2/2004 | Hartlep |
| 6,694,163 B1 | 2/2004 | Vining |
| 6,708,096 B1 | 3/2004 | Frei et al. |
| 6,741,892 B1 | 5/2004 | Meadows et al. |
| 6,748,098 B1 | 6/2004 | Rosenfeld |
| 6,748,276 B1 | 6/2004 | Daignault, Jr. et al. |
| 6,778,846 B1 | 8/2004 | Martinez et al. |
| 6,788,969 B2 | 9/2004 | Dupree et al. |
| 6,795,737 B2 | 9/2004 | Gielen et al. |
| 6,827,681 B2 | 12/2004 | Tanner et al. |
| 6,830,544 B2 | 12/2004 | Tanner |
| 6,845,267 B2 | 1/2005 | Harrison et al. |
| 6,850,802 B2 | 2/2005 | Holsheimer |
| 6,895,280 B2 | 5/2005 | Meadows et al. |
| 6,909,913 B2 | 6/2005 | Vining |
| 6,937,891 B2 | 8/2005 | Leinders et al. |
| 6,937,903 B2 | 8/2005 | Schuler et al. |
| 6,944,497 B2 | 9/2005 | Stypulkowski |
| 6,944,501 B1 | 9/2005 | Pless |
| 6,950,707 B2 | 9/2005 | Whitehurst |
| 6,969,388 B2 | 11/2005 | Goldman et al. |

(56) References Cited

U.S. PATENT DOCUMENTS

| | | |
|---|---|---|
| 7,003,349 B1 | 2/2006 | Andersson et al. |
| 7,003,352 B1 | 2/2006 | Whitehurst |
| 7,008,370 B2 | 3/2006 | Tanner et al. |
| 7,008,413 B2 | 3/2006 | Kovach et al. |
| 7,035,690 B2 | 4/2006 | Goetz |
| 7,043,293 B1 | 5/2006 | Baura |
| 7,047,082 B1 | 5/2006 | Schrom et al. |
| 7,047,084 B2 | 5/2006 | Erickson et al. |
| 7,050,857 B2 | 5/2006 | Samuelsson et al. |
| 7,054,692 B1 | 5/2006 | Whitehurst et al. |
| 7,136,518 B2 | 5/2006 | Griffin et al. |
| 7,058,446 B2 | 6/2006 | Schuler et al. |
| 7,082,333 B1 | 7/2006 | Bauhahn et al. |
| 7,107,102 B2 | 9/2006 | Daignault et al. |
| 7,126,000 B2 | 10/2006 | Ogawa et al. |
| 7,127,297 B2 | 10/2006 | Law et al. |
| 7,136,695 B2 | 11/2006 | Pless et al. |
| 7,142,923 B2 | 11/2006 | North et al. |
| 7,146,219 B2 | 12/2006 | Sieracki et al. |
| 7,146,223 B1 | 12/2006 | King |
| 7,151,961 B1 | 12/2006 | Whitehurst |
| 7,155,279 B2 | 12/2006 | Whitehurst |
| 7,167,760 B2 | 1/2007 | Dawant et al. |
| 7,177,674 B2 | 2/2007 | Echauz et al. |
| 7,181,286 B2 | 2/2007 | Sieracki et al. |
| 7,184,837 B2 | 2/2007 | Goetz |
| 7,191,014 B2 | 3/2007 | Kobayashi et al. |
| 7,209,787 B2 | 4/2007 | Dilorenzo |
| 7,211,050 B1 | 5/2007 | Caplygin |
| 7,216,000 B2 | 5/2007 | Sieracki et al. |
| 7,217,276 B2 | 5/2007 | Henderson |
| 7,218,968 B2 | 5/2007 | Condie et al. |
| 7,228,179 B2 | 6/2007 | Campen et al. |
| 7,231,254 B2 | 6/2007 | DiLorenzo |
| 7,236,830 B2 | 6/2007 | Gliner |
| 7,239,910 B2 | 7/2007 | Tanner |
| 7,239,916 B2 | 7/2007 | Thompson et al. |
| 7,239,926 B2 | 7/2007 | Goetz |
| 7,242,984 B2 | 7/2007 | DiLorenzo |
| 7,244,150 B1 | 7/2007 | Brase et al. |
| 7,252,090 B2 | 8/2007 | Goetz |
| 7,254,445 B2 | 8/2007 | Law et al. |
| 7,254,446 B1 | 8/2007 | Erickson |
| 7,257,447 B2 | 8/2007 | Cates et al. |
| 7,266,412 B2 | 9/2007 | Stypulkowski |
| 7,294,107 B2 | 11/2007 | Simon et al. |
| 7,295,876 B1 | 11/2007 | Erickson |
| 7,299,096 B2 | 11/2007 | Balzer et al. |
| 7,308,302 B1 | 12/2007 | Schuler et al. |
| 7,313,430 B2 | 12/2007 | Urquhart |
| 7,324,851 B1 | 1/2008 | DiLorenzo |
| 7,346,382 B2 | 3/2008 | McIntyre et al. |
| 7,388,974 B2 | 6/2008 | Yanagita |
| 7,450,997 B1 | 11/2008 | Pianca et al. |
| 7,463,928 B2 | 12/2008 | Lee et al. |
| 7,499,048 B2 | 3/2009 | Sieracki et al. |
| 7,505,815 B2 | 3/2009 | Lee et al. |
| 7,548,786 B2 | 6/2009 | Lee et al. |
| 7,565,199 B2 | 7/2009 | Sheffield et al. |
| 7,603,177 B2 | 10/2009 | Sieracki et al. |
| 7,617,002 B2 | 11/2009 | Goetz |
| 7,623,918 B2 | 11/2009 | Goetz |
| 7,650,184 B2 | 1/2010 | Walter |
| 7,657,319 B2 | 2/2010 | Goetz et al. |
| 7,672,734 B2 | 3/2010 | Anderson et al. |
| 7,676,273 B2 | 3/2010 | Goetz et al. |
| 7,680,526 B2 | 3/2010 | McIntyre et al. |
| 7,734,340 B2 | 6/2010 | De Ridder |
| 7,761,165 B1 | 7/2010 | He et al. |
| 7,783,359 B2 | 8/2010 | Meadows |
| 7,792,590 B1 | 9/2010 | Pianca et al. |
| 7,809,446 B2 | 10/2010 | Meadows |
| 7,826,902 B2 | 11/2010 | Stone et al. |
| 7,848,802 B2 | 12/2010 | Goetz et al. |
| 7,860,548 B2 | 12/2010 | McIntyre et al. |
| 7,904,134 B2 | 3/2011 | McIntyre et al. |
| 7,945,105 B1 | 5/2011 | Jaenisch |
| 7,949,395 B2 | 5/2011 | Kuzma |
| 7,974,706 B2 | 7/2011 | Moffitt et al. |
| 8,000,794 B2 | 8/2011 | Lozano |
| 8,019,439 B2 | 9/2011 | Kuzma et al. |
| 8,175,710 B2 | 5/2012 | He |
| 8,180,601 B2 | 5/2012 | Butson et al. |
| 8,187,209 B1 | 5/2012 | Giuffrida |
| 8,195,300 B2 | 6/2012 | Gliner et al. |
| 8,224,450 B2 | 7/2012 | Brase |
| 8,257,684 B2 | 9/2012 | Covalin et al. |
| 8,262,714 B2 | 9/2012 | Hulvershorn et al. |
| 8,271,094 B1 | 9/2012 | Moffitt et al. |
| 8,280,514 B2 | 10/2012 | Lozano et al. |
| 8,295,944 B2 | 10/2012 | Howard et al. |
| 8,326,433 B2 | 12/2012 | Blum et al. |
| 8,364,278 B2 | 1/2013 | Pianca et al. |
| 8,391,985 B2 | 3/2013 | McDonald |
| 8,429,174 B2 | 4/2013 | Ramani et al. |
| 8,452,415 B2 | 5/2013 | Goetz et al. |
| 8,473,061 B2 | 6/2013 | Moffitt et al. |
| 8,483,237 B2 | 7/2013 | Zimmermann et al. |
| 8,543,189 B2 | 9/2013 | Paitel et al. |
| 8,571,665 B2 | 10/2013 | Moffitt et al. |
| 8,606,360 B2 | 12/2013 | Butson et al. |
| 8,620,452 B2 | 12/2013 | King et al. |
| 8,675,945 B2 | 3/2014 | Barnhorst et al. |
| 8,679,038 B1 | 3/2014 | Giuffrida |
| 8,688,235 B1 | 4/2014 | Pianca et al. |
| 8,792,993 B2 | 7/2014 | Pianca et al. |
| 8,831,731 B2 | 9/2014 | Blum et al. |
| 8,845,557 B1 | 9/2014 | Giuffrida et al. |
| 8,849,632 B2 | 9/2014 | Sparks et al. |
| 8,958,615 B2 | 2/2015 | Blum et al. |
| 9,248,272 B2 | 2/2016 | Romero |
| 10,603,498 B2 * | 3/2020 | Blum ................ A61N 1/37247 |
| 2001/0031071 A1 | 10/2001 | Nichols et al. |
| 2002/0032375 A1 | 3/2002 | Bauch et al. |
| 2002/0062143 A1 | 5/2002 | Baudino et al. |
| 2002/0087201 A1 | 7/2002 | Firlik et al. |
| 2002/0099295 A1 | 7/2002 | Gil et al. |
| 2002/0115603 A1 | 8/2002 | Whitehouse |
| 2002/0116030 A1 | 8/2002 | Rezei |
| 2002/0123780 A1 | 9/2002 | Grill et al. |
| 2002/0128694 A1 | 9/2002 | Holsheimer |
| 2002/0151939 A1 | 10/2002 | Rezai |
| 2002/0183607 A1 | 12/2002 | Bauch et al. |
| 2002/0183740 A1 | 12/2002 | Edwards et al. |
| 2002/0183817 A1 | 12/2002 | Van Venrooij et al. |
| 2003/0097159 A1 | 5/2003 | Schiff et al. |
| 2003/0149450 A1 | 8/2003 | Mayberg |
| 2003/0171791 A1 | 9/2003 | KenKnight et al. |
| 2003/0212439 A1 | 11/2003 | Schuler et al. |
| 2004/0034394 A1 | 2/2004 | Woods et al. |
| 2004/0044279 A1 | 3/2004 | Lewin et al. |
| 2004/0044378 A1 | 3/2004 | Holsheimer |
| 2004/0044379 A1 | 3/2004 | Holsheimer |
| 2004/0054297 A1 | 3/2004 | Wingeier et al. |
| 2004/0059395 A1 | 3/2004 | North et al. |
| 2004/0106916 A1 | 6/2004 | Quaid et al. |
| 2004/0133248 A1 | 7/2004 | Frei et al. |
| 2004/0152957 A1 | 8/2004 | Stivoric et al. |
| 2004/0181262 A1 | 9/2004 | Bauhahn |
| 2004/0186532 A1 | 9/2004 | Tadlock |
| 2004/0199216 A1 | 10/2004 | Lee et al. |
| 2004/0267330 A1 | 12/2004 | Lee et al. |
| 2005/0021090 A1 | 1/2005 | Schuler et al. |
| 2005/0033380 A1 | 2/2005 | Tanner et al. |
| 2005/0049649 A1 | 3/2005 | Luders et al. |
| 2005/0060001 A1 | 3/2005 | Singhal et al. |
| 2005/0060009 A1 | 3/2005 | Goetz |
| 2005/0070781 A1 | 3/2005 | Dawant et al. |
| 2005/0075689 A1 | 4/2005 | Toy et al. |
| 2005/0085714 A1 | 4/2005 | Foley et al. |
| 2005/0165294 A1 | 7/2005 | Weiss |
| 2005/0171587 A1 | 8/2005 | Daglow et al. |
| 2005/0228250 A1 | 10/2005 | Bitter et al. |
| 2005/0251061 A1 | 11/2005 | Schuler et al. |

(56) References Cited

U.S. PATENT DOCUMENTS

| | | |
|---|---|---|
| 2005/0261061 A1 | 11/2005 | Nguyen et al. |
| 2005/0261601 A1 | 11/2005 | Schuler et al. |
| 2005/0261747 A1 | 11/2005 | Schuler et al. |
| 2005/0267347 A1 | 12/2005 | Oster |
| 2005/0288732 A1 | 12/2005 | Schuler et al. |
| 2006/0004422 A1 | 1/2006 | De Ridder |
| 2006/0017749 A1 | 1/2006 | McIntyre et al. |
| 2006/0020292 A1 | 1/2006 | Goetz et al. |
| 2006/0069415 A1 | 3/2006 | Cameron et al. |
| 2006/0094951 A1 | 5/2006 | Dean et al. |
| 2006/0095088 A1 | 5/2006 | De Riddler |
| 2006/0155340 A1 | 7/2006 | Schuler et al. |
| 2006/0206169 A1 | 9/2006 | Schuler |
| 2006/0218007 A1 | 9/2006 | Bjorner et al. |
| 2006/0224189 A1 | 10/2006 | Schuler et al. |
| 2006/0235472 A1 | 10/2006 | Goetz et al. |
| 2006/0259079 A1 | 11/2006 | King |
| 2006/0259099 A1 | 11/2006 | Goetz et al. |
| 2007/0000372 A1 | 1/2007 | Rezai et al. |
| 2007/0017749 A1 | 1/2007 | Dold et al. |
| 2007/0027514 A1 | 2/2007 | Gerber |
| 2007/0043268 A1 | 2/2007 | Russell |
| 2007/0049817 A1 | 3/2007 | Preiss et al. |
| 2007/0067003 A1 | 3/2007 | Sanchez et al. |
| 2007/0078498 A1 | 4/2007 | Rezai et al. |
| 2007/0083104 A1 | 4/2007 | Butson et al. |
| 2007/0123953 A1 | 5/2007 | Lee et al. |
| 2007/0129769 A1 | 6/2007 | Bourget et al. |
| 2007/0135855 A1 | 6/2007 | Foshee et al. |
| 2007/0150036 A1 | 6/2007 | Anderson |
| 2007/0156186 A1 | 7/2007 | Lee et al. |
| 2007/0162086 A1 | 7/2007 | DiLorenzo |
| 2007/0162235 A1 | 7/2007 | Zhan et al. |
| 2007/0168004 A1 | 7/2007 | Walter |
| 2007/0168007 A1 | 7/2007 | Kuzma et al. |
| 2007/0185544 A1 | 8/2007 | Dawant et al. |
| 2007/0191887 A1 | 8/2007 | Schuler et al. |
| 2007/0191912 A1 | 8/2007 | Fischer et al. |
| 2007/0197891 A1 | 8/2007 | Shachar et al. |
| 2007/0203450 A1 | 8/2007 | Berry |
| 2007/0203532 A1 | 8/2007 | Tass et al. |
| 2007/0203537 A1 | 8/2007 | Goetz et al. |
| 2007/0203538 A1 | 8/2007 | Stone et al. |
| 2007/0203539 A1 | 8/2007 | Stone et al. |
| 2007/0203540 A1 | 8/2007 | Goetz et al. |
| 2007/0203541 A1 | 8/2007 | Goetz et al. |
| 2007/0203543 A1 | 8/2007 | Stone et al. |
| 2007/0203544 A1 | 8/2007 | Goetz et al. |
| 2007/0203545 A1 | 8/2007 | Stone et al. |
| 2007/0203546 A1 | 8/2007 | Stone et al. |
| 2007/0213789 A1 | 9/2007 | Nolan et al. |
| 2007/0213790 A1 | 9/2007 | Nolan et al. |
| 2007/0244519 A1 | 10/2007 | Keacher et al. |
| 2007/0245318 A1 | 10/2007 | Goetz et al. |
| 2007/0255321 A1 | 11/2007 | Gerber et al. |
| 2007/0255322 A1 | 11/2007 | Gerber et al. |
| 2007/0265664 A1 | 11/2007 | Gerber et al. |
| 2007/0276441 A1 | 11/2007 | Goetz |
| 2007/0282189 A1 | 12/2007 | Dan et al. |
| 2007/0288064 A1 | 12/2007 | Butson et al. |
| 2008/0027514 A1 | 1/2008 | DeMulling et al. |
| 2008/0039895 A1 | 2/2008 | Fowler et al. |
| 2008/0071150 A1 | 3/2008 | Miesel et al. |
| 2008/0081982 A1 | 4/2008 | Simon et al. |
| 2008/0086451 A1 | 4/2008 | Torres et al. |
| 2008/0103533 A1 | 5/2008 | Patel et al. |
| 2008/0114233 A1 | 5/2008 | McIntyre et al. |
| 2008/0114579 A1 | 5/2008 | McIntyre et al. |
| 2008/0123922 A1 | 5/2008 | Gielen et al. |
| 2008/0123923 A1 | 5/2008 | Gielen et al. |
| 2008/0133141 A1 | 6/2008 | Frost |
| 2008/0141217 A1 | 6/2008 | Goetz et al. |
| 2008/0154340 A1 | 6/2008 | Goetz et al. |
| 2008/0154341 A1 | 6/2008 | McIntyre et al. |
| 2008/0163097 A1 | 7/2008 | Goetz et al. |
| 2008/0183256 A1 | 7/2008 | Keacher |
| 2008/0188734 A1 | 8/2008 | Suryanarayanan et al. |
| 2008/0215118 A1 | 9/2008 | Goetz et al. |
| 2008/0227139 A1 | 9/2008 | Deisseroth et al. |
| 2008/0242950 A1 | 10/2008 | Jung et al. |
| 2008/0261165 A1 | 10/2008 | Steingart et al. |
| 2008/0269588 A1 | 10/2008 | Csavoy et al. |
| 2008/0300654 A1 | 12/2008 | Lambert et al. |
| 2008/0300797 A1 | 12/2008 | Tabibiazar et al. |
| 2009/0016491 A1 | 1/2009 | Li |
| 2009/0054950 A1 | 2/2009 | Stephens |
| 2009/0082640 A1 | 3/2009 | Kovach et al. |
| 2009/0082829 A1 | 3/2009 | Panken et al. |
| 2009/0112289 A1 | 4/2009 | Lee et al. |
| 2009/0118635 A1 | 5/2009 | Lujan et al. |
| 2009/0118786 A1 | 5/2009 | Meadows et al. |
| 2009/0149917 A1 | 6/2009 | Whitehurst et al. |
| 2009/0187222 A1 | 7/2009 | Barker |
| 2009/0196471 A1 | 8/2009 | Goetz et al. |
| 2009/0196472 A1 | 8/2009 | Goetz et al. |
| 2009/0198306 A1 | 8/2009 | Goetz et al. |
| 2009/0198354 A1 | 8/2009 | Wilson |
| 2009/0204192 A1 | 8/2009 | Carlton et al. |
| 2009/0208073 A1 | 8/2009 | McIntyre et al. |
| 2009/0210208 A1 | 8/2009 | McIntyre et al. |
| 2009/0242399 A1 | 10/2009 | Kamath et al. |
| 2009/0276008 A1 | 11/2009 | Lee et al. |
| 2009/0276021 A1 | 11/2009 | Meadows et al. |
| 2009/0281595 A1 | 11/2009 | King et al. |
| 2009/0281596 A1 | 11/2009 | King et al. |
| 2009/0287271 A1 | 11/2009 | Blum et al. |
| 2009/0287272 A1 | 11/2009 | Kokones et al. |
| 2009/0287273 A1 | 11/2009 | Carlton et al. |
| 2009/0287467 A1 | 11/2009 | Sparks et al. |
| 2009/0299164 A1 | 12/2009 | Singhal et al. |
| 2009/0299165 A1 | 12/2009 | Singhal et al. |
| 2009/0299380 A1 | 12/2009 | Singhal et al. |
| 2010/0010432 A1 | 1/2010 | Skelton |
| 2010/0010566 A1 | 1/2010 | Thacker et al. |
| 2010/0010646 A1 | 1/2010 | Drew et al. |
| 2010/0023103 A1 | 1/2010 | Elborno |
| 2010/0023130 A1 | 1/2010 | Henry et al. |
| 2010/0030312 A1 | 2/2010 | Shen |
| 2010/0049276 A1 | 2/2010 | Blum et al. |
| 2010/0049280 A1 | 2/2010 | Goetz |
| 2010/0064249 A1 | 3/2010 | Groetken |
| 2010/0076535 A1 | 3/2010 | Pianca et al. |
| 2010/0113959 A1 | 5/2010 | Pascual-Leone et al. |
| 2010/0121409 A1 | 5/2010 | Kothandaraman et al. |
| 2010/0135553 A1 | 6/2010 | Joglekar |
| 2010/0137944 A1 | 6/2010 | Zhu |
| 2010/0152604 A1 | 6/2010 | Kaula et al. |
| 2010/0179562 A1 | 7/2010 | Linker et al. |
| 2010/0268298 A1 | 10/2010 | Moffitt |
| 2010/0324410 A1 | 12/2010 | Paek et al. |
| 2010/0331883 A1 | 12/2010 | Schmitz et al. |
| 2011/0004267 A1 | 1/2011 | Meadows |
| 2011/0005069 A1 | 1/2011 | Pianca |
| 2011/0040351 A1 | 2/2011 | Butson et al. |
| 2011/0066407 A1 | 3/2011 | Butson et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0172737 A1 | 7/2011 | Davis et al. |
| 2011/0184487 A1 | 7/2011 | Alberts et al. |
| 2011/0191275 A1 | 8/2011 | Lujan et al. |
| 2011/0196253 A1 | 8/2011 | McIntyre et al. |
| 2011/0213440 A1 | 9/2011 | Fowler et al. |
| 2011/0238129 A1 | 9/2011 | Moffitt |
| 2011/0306845 A1 | 12/2011 | Osorio |
| 2011/0306846 A1 | 12/2011 | Osorio |
| 2011/0307032 A1 | 12/2011 | Goetz et al. |
| 2011/0313500 A1 | 12/2011 | Barker |
| 2012/0016378 A1 | 1/2012 | Pianca et al. |
| 2012/0027272 A1 | 2/2012 | Akinyemi et al. |
| 2012/0046710 A1 | 2/2012 | Digiore et al. |
| 2012/0046715 A1 | 2/2012 | Moffitt et al. |

(56) References Cited

U.S. PATENT DOCUMENTS

| | | |
|---|---|---|
| 2012/0071949 A1 | 3/2012 | Pianca et al. |
| 2012/0078106 A1 | 3/2012 | Dentinger et al. |
| 2012/0089205 A1 | 4/2012 | Boyden et al. |
| 2012/0101552 A1 | 4/2012 | Lazarewicz et al. |
| 2012/0116476 A1 | 5/2012 | Kothandaraman |
| 2012/0165898 A1 | 6/2012 | Moffitt |
| 2012/0165901 A1 | 6/2012 | Zhu et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | Digiore et al. |
| 2012/0203321 A1 | 8/2012 | Moffitt et al. |
| 2012/0207378 A1 | 8/2012 | Gupta et al. |
| 2012/0226138 A1 | 9/2012 | DeSalles et al. |
| 2012/0229468 A1 | 9/2012 | Lee et al. |
| 2012/0265262 A1 | 10/2012 | Osorio |
| 2012/0265268 A1 | 10/2012 | Blum et al. |
| 2012/0302912 A1 | 11/2012 | Moffitt et al. |
| 2012/0303087 A1 | 11/2012 | Moffitt et al. |
| 2012/0314924 A1 | 12/2012 | Carlton et al. |
| 2012/0316615 A1 | 12/2012 | Digiore et al. |
| 2012/0316619 A1 | 12/2012 | Goetz et al. |
| 2012/0330622 A1 | 12/2012 | Butson et al. |
| 2013/0039550 A1 | 2/2013 | Blum et al. |
| 2013/0060305 A1 | 3/2013 | Bokil |
| 2013/0105071 A1 | 5/2013 | Digiore et al. |
| 2013/0116744 A1 | 5/2013 | Blum et al. |
| 2013/0116748 A1 | 5/2013 | Bokil et al. |
| 2013/0116749 A1 | 5/2013 | Carlton et al. |
| 2013/0116929 A1 | 5/2013 | Carlton et al. |
| 2013/0150922 A1 | 6/2013 | Butson et al. |
| 2013/0197424 A1 | 8/2013 | Bedenbaugh |
| 2013/0197602 A1 | 8/2013 | Pianca et al. |
| 2013/0261684 A1 | 10/2013 | Howard |
| 2013/0317587 A1 | 11/2013 | Barker |
| 2013/0325091 A1 | 12/2013 | Pianca et al. |
| 2014/0039587 A1 | 2/2014 | Romero |
| 2014/0066999 A1 | 3/2014 | Carcieri et al. |
| 2014/0067018 A1 | 3/2014 | Carcieri et al. |
| 2014/0067022 A1 | 3/2014 | Carcieri et al. |
| 2014/0122379 A1 | 5/2014 | Moffitt et al. |
| 2014/0277284 A1 | 9/2014 | Chen et al. |
| 2014/0296953 A1 | 10/2014 | Pianca et al. |
| 2014/0343647 A1 | 11/2014 | Romero et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0018915 A1 | 1/2015 | Leven |
| 2015/0021817 A1 | 1/2015 | Romero et al. |
| 2015/0045864 A1 | 2/2015 | Howard |
| 2015/0051681 A1 | 2/2015 | Hershey |
| 2015/0066111 A1 | 3/2015 | Blum et al. |
| 2015/0066120 A1 | 3/2015 | Govea |
| 2015/0134031 A1 | 5/2015 | Moffitt et al. |
| 2015/0151113 A1 | 6/2015 | Govea et al. |
| 2016/0022995 A1 | 1/2016 | Kothandaraman et al. |
| 2016/0023008 A1 | 1/2016 | Kothandaraman |
| 2016/0030749 A1 | 2/2016 | Carcieri et al. |
| 2016/0096025 A1 | 4/2016 | Moffitt et al. |
| 2016/0136429 A1 | 5/2016 | Massoumi et al. |
| 2016/0136443 A1 | 5/2016 | Kothandaraman et al. |
| 2016/0228692 A1 | 8/2016 | Steinke et al. |
| 2016/0256691 A1 | 9/2016 | Cecchi et al. |
| 2016/0256693 A1 | 9/2016 | Parramon |
| 2016/0375248 A1 | 12/2016 | Carcieri et al. |
| 2016/0375258 A1 | 12/2016 | Steinke |
| 2017/0100593 A1 | 4/2017 | Zottola |
| 2017/0252570 A1 | 9/2017 | Serrano Carmona et al. |
| 2017/0304610 A1 | 10/2017 | Huibregtse et al. |
| 2017/0304633 A1 | 10/2017 | Zhang |
| 2017/0372039 A1 | 12/2017 | Mustakos et al. |

FOREIGN PATENT DOCUMENTS

| | | |
|---|---|---|
| EP | 1372780 | 1/2004 |
| EP | 1559369 | 8/2005 |
| WO | 97/39797 | 10/1997 |
| WO | 98/48880 | 11/1998 |
| WO | 01/90876 | 11/2001 |
| WO | 02/26314 | 4/2002 |
| WO | 02/28473 | 4/2002 |
| WO | 02/065896 | 8/2002 |
| WO | 02/072192 | 9/2002 |
| WO | 03/086185 | 10/2003 |
| WO | 2004/019799 A2 | 3/2004 |
| WO | 2004041080 | 5/2005 |
| WO | 2006017053 | 2/2006 |
| WO | 2006113305 | 10/2006 |
| WO | 20071097859 | 8/2007 |
| WO | 20071097861 A1 | 8/2007 |
| WO | 2007/100427 | 9/2007 |
| WO | 2007/100428 | 9/2007 |
| WO | 2007/112061 | 10/2007 |
| WO | 2009097224 | 8/2009 |
| WO | 2010/109448 | 9/2010 |
| WO | 2010/120823 A2 | 10/2010 |
| WO | 2011025865 | 3/2011 |
| WO | 2011/139779 A1 | 11/2011 |
| WO | 2011/159688 A2 | 12/2011 |
| WO | 2012088482 | 6/2012 |

OTHER PUBLICATIONS

Obeso, J. A., et al., "Deep-brain stimulation of the subthalamic nucleus or the pars interna of the globus pallidus in Parkinson's disease.", N Engl J Med., 345{131. The Deep-Brain Stimulation for Parkinson's Disease Study Group, (Sep. 27, 2001 ), 956-63.

Butson et al.. "Current Steering to control the volume of tissue activated during deep brain stimulation," vol. 1, No. 1, Dec. 3, 2007, pp. 7-15.

Patrick, S. K., et al., "Quantification of the UPDRS rigidity scale", IEEE Transactions on Neural Systems and Rehabilitation Engineering, [see also IEEE Trans. on Rehabilitation Engineering 9(1). (2001), 31-41.

Phillips, M. D., et al., "Parkinson disease: pattern of functional MR imaging activation during deep brain stimulation of subthalamic nucleus-initial experience", Radiology 239(1). (Apr. 2006), 209-16.

Ericsson, A. et al., "Construction of a patient-specific atlas of the brain: Application to normal aging," Biomedical Imaging: From Nano to Macro, ISBI 2008, 5th IEEE International Symposium, May 14, 2008, pp. 480-483.

Kaikai Shen et al., "Atlas selection strategy using least angle regression in multi-atlas segmentation propagation," Biomedical Imaging: From Nano to Macro, 2011, 8th IEEE International Symposium, ISBI 2011, Mar. 30, 2011, pp. 1746-1749.

Liliane Ramus et al., "Assessing selection methods in the cotnext of multi-atlas based segmentation," Biomedical Imaging: From Nano to Macro, 2010, IEEE International Symposium, Apr. 14, 2010, pp. 1321-1324.

Olivier Commowick et al., "Using Frankenstein's Creature Paradigm to Build a Patient Specific Atlas," Sep. 20, 2009, Medical Image Computing and Computer-Assisted Intervention, pp. 993-1000.

Lotjonen J.M.P. et al., "Fast and robust multi-atlas segmentation of brain magnetic resonance images," NeuroImage, Academic Press, vol. 49, No. 3, Feb. 1, 2010, pp. 2352-2365.

Mcintyre, C. C., et al., "How does deep brain stimulation work? Present understanding and future questions.", J Clin Neurophysiol. 21 (1 ). (Jan.-Feb. 2004 ), 40-50.

Sanchez Castro et al., "A cross validation study of deep brain stimulation targeting: From experts to Atlas-Based, Segmentation-Based and Automatic Registration Algorithms," IEEE Transactions on Medical Imaging, vol. 25, No. 11, Nov. 1, 2006, pp. 1440-1450.

Plaha, P. , et al., "Stimulation of the caudal zona incerta is superior to stimulation of the subthalamic nucleus in improving contralateral parkinsonism.", Brain 129{Pt 7) (Jul. 2006), 1732-4 7.

(56) References Cited

OTHER PUBLICATIONS

Rattay, F, "Analysis of models for external stimulation of axons", IEEE Trans. Biomed. Eng. vol. 33 (1986), 974-977.

Rattay, F., "Analysis of the electrical excitation of CNS neurons", IEEE Transactions on Biomedical Engineering 45(6). (Jun. 1998), 766-772.

Rose, T. L., et al., "Electrical stimulation with Pt electrodes. VIII. Electrochemically safe charge injection limits with 0.2 ms pulses [neuronal application]", IEEE Transactions on Biomedical Engineering, 37(11 }, (Nov. 1990), 1118-1120.

Rubinstein, J. T., et al., "Signal coding in cochlear implants: exploiting stochastic effects of electrical stimulation", Ann Otol Rhinol Laryngol Suppl.. 191, (Sep. 2003), 14-9.

Schwan, H.P., et al., "The conductivity of living tissues.", Ann NY Acad Sci., 65(6). (AUQ., 1957), 1007-13.

Taylor, R. S., et al., "Spinal cord stimulation for chronic back and leg pain and failed back surgery syndrome: a systematic review and analysis of prognostic factors", Spine 30(1 ). (Jan. 1, 2005), 152-60.

Siegel, Ralph M. et al., "Spatiotemporal dynamics of the functional architecture for gain fields in inferior parietal lobule of behaving monkey," Cerebral Cortex, New York, NY, vol. 17, No. 2, Feb. 2007, pp. 378-390.

Klein, A. et al., "Evaluation of 14 nonlinear deformation algorithms applied to human brain MRI registration," NeuroImage, Academic Press, Orlando, FL, vol. 46, No. 3, Jul. 2009, pp. 786-802.

Geddes, L. A., et al., "The specific resistance of biological material—a compendium of data for the biomedical engineer and physiologist.", Med Biol Ena. 5(3). (May 1967), 271-93.

Gimsa, J., et al., "Choosing electrodes for deep brain stimulation experiments—electrochemical considerations.", J Neurosci Methods, 142(2), (Mar. 30, 2005), 251-65.

Vadailhet, M. , et al., "Bilateral deep-brain stimulation of the globus pallidus in primary generalized dystonia", N Engl J Med. 352(5) (Feb. 3, 2005), 459-67.

Izad, Oliver, "Computationally Efficient Method in Predicating Axonal Excitation," Dissertation for Master Degree, Department of Biomedical Engineering, Case Western Reserve University, May 2009.

Jaccard, Paul, "Elude comparative de la distribution florale dans une portion odes Aples et des Jura," Bulletin de la Societe Vaudoise des Sciences Naturelles (1901), 37:547-579.

Dice, Lee R., "Measures of the Amount of Ecoiogic Association Between Species," Ecology 26(3) (1945): 297-302. doi: 10.2307/1932409, http://jstor.org/stable/1932409.

Rand, WM., "Objective criteria for the evaluation of clustering methods," Journal of the American Statistical Association (American Statistical Association) 66 (336) (1971 ): 846-850, doi:10.2307/2284239, http://jstor.org/stable/2284239.

Hubert, Lawrence et al., "Comparing partitions," Journal of Classification 2(1) (1985): 193-218, doi:10.1007/BF01908075.

Cover, T.M. et al., "Elements of information theory," (1991) John Wiley & Sons, New York, NY.

Meila, Marina, "Comparing Clusterings by the Variation of Information," Learning Theory and Kernel Machines (2003): 173-187.

Viola, P., et al., "Alignment by maximization of mutual information", International Journal of Com outer Vision 24(2). ( 1997), 137-154.

Butson et al. "StimExplorer: Deep Brain Stimulation Parameter Selection Software System," Acta Neurochirugica, Jan. 1, 2007, vol. 97, No. 2, pp. 569-574.

Butson et al. "Role of Electrode Design on the Volume of Tissue Activated During Deep Brain Stimulation," Journal of Neural Engineering, Mar. 1, 2006, vol. 3, No. 1, pp. 1-8.

Volkmann et al., Indroduction to the Programming of Deep Brain Stimulators, Movement Disorders, vol. 17, Suppl. 3, pp. S181-S187 (2002).

Miocinovic et al. "Cicerone: Stereotactic Neurophysiological Recording and Deep Brain Stimulation Electrode Placement Software System," Acta Neurochirurgica Suppl., Jan. 1, 2007, vol. 97, No. 2, pp. 561-567.

Schmidt et al. "Sketching and Composing Widgets for 3D Manipulation," Eurographics, Apr. 2008, vol. 27, No. 2, pp. 301-310.

Volkmann, J. , et al., "Basic algorithms for the programming of deep brain stimulation in Parkinson's disease", Mov Disord., 21 Suppl 14. (Jun. 2006), S284-9.

Walter, B. L., et al., "Surgical treatment for Parkinson's disease", Lancet Neural. 3(12). (Dec. 2004), 719-28.

Wei, X. F., et al., "Current density distributions, field distributions and impedance analysis of segmented deep brain stimulation electrodes", J Neural Eng . . . 2(4). (Dec. 2005), 139-47.

Zonenshayn, M. , et al., "Location of the active contact within the subthalamic nucleus (STN) in the treatment of idiopathic Parkinson's disease.", Surg Neurol., 62(3) (Sep. 2004), 216-25.

Da Silva et al (A primer on diffusion tensor imaging of anatomical substructures. Neurosurg Focus 15(1): p. 1-4, Article 4, 2003.).

Micheli-Tzanakou, E., et al., "Computational Intelligence for target assesment in Parkinson's disease", Proceedings of SPIE vol. 4479. Applications and Science of Neural Networks, Fuzzy Systems, and Evolutionary Computation IV, (2001), 54-69.

Grill, W. M., "Stimulus waveforms for selective neural stimulation", IEEE Engineering in Medicine and Biology Magazine, 14(4), (Jul.-Aug. 1995), 375-385.

Miocinovic, S., et al., "Sensitivity of temporal excitation properties to the neuronal element activated by extracellular stimulation", J Neurosci Methods. 132(1). (Jan. 15, 2004), 91-9.

Hunka, K. et al., Nursing Time to Program and Assess Deep Brain Stimulators in Movement Disorder Patients, J. Neursci Nurs., 37: 204-10 (Aug. 2005).

Moss, J. , et al., "Electron microscopy of tissue adherent to explanted electrodes in dystonia and Parkinson's disease", Brain, 127{Pt 12). (Dec., 2004), 2755-63.

Montgomery, E. B., et al., "Mechanisms of deep brain stimulation and future technical developments.", Neurol Res. 22(3). (Apr. 2000), 259-66.

Merrill, D. R., et al., "Electrical stimulation of excitable tissue: design of efficacious and safe protocols", J Neurosci Methods. 141(2), (Feb. 15, 2005), 171-98.

Fisekovic et al., "New Controller for Functional Electrical Stimulation Systems", Med. Eng. Phys. 2001; 23:391-399.

Zhang, Y., et al., "Atlas-guided tract reconstruction for automated and comprehensive examination of the white matter anatomy," Neuroimage 52(4) (2010), pp. 1289-1301.

""BioPSE" The Biomedical Problem Solving Environment", htt12:// www.sci.utah.edu/cibc/software/index.html, MCRR Center for Integrative Biomedical Computing, (2004).

Andrews, R. J., "Neuroprotection trek—the next generation: neuromodulation I. Techniques—deep brain stimulation, vagus nerve stimulation, and transcranial magnetic stimulation.", Ann NY Acad Sci. 993. (May 2003), 1-13.

Carnevale, N.T. et al., "The Neuron Book," Cambridge, UK: Cambridge University Press (2006), 480 pages.

Chaturvedi: "Development of Accurate Computational Models for Patient-Specific Deep Brain Stimulation," Electronic Thesis or Dissertation, Jan. 2012, 162 pages.

Chaturvedi, A. et al.: "Patient-specific models of deep brain stimulation: Influence of field model complexity on neural activation predictions." Brain Stimulation, Elsevier, Amsterdam, NL, vol. 3, No. 2, Apr. 2010, pp. 65-77.

Frankemolle, et al., "Reversing cognitive-motor impairments in Parkinson's disease patients using a computational modeling approach to deep brain stimulation programming," Brian 133 (2010), pp. 746-761.

McIntyre, C.C., et al., "Modeling the excitablitity of mammalian nerve fibers: influence of afterpotentials on the recovery cycle," J Neurophysiol, 87(2) (Feb. 2002), pp. 995-1006.

Peterson, et al., "Predicting myelinated axon activation using spatial characteristics of the extracellular field," Journal of Neural Engineering, 8 (2011), 12 pages.

Warman, et al., "Modeling the Effects of Electric Fields on nerver Fibers; Dermination of Excitation Thresholds,"IEEE Transactions on Biomedical Engineering, vol. 39, No. 12 (Dec. 1992), pp. 1244-1254.

(56) References Cited

OTHER PUBLICATIONS

Wesselink, et al., "Analysis of Current Density and Related Parameters in Spinal Cord Stimulation," IEEE Transactions on Rehabilitation Engineering, vol. 6, No. 2, Jun. 1998, pp. 200-207.
Andrews, R. J., "Neuroprotection trek—the next generation: neuromodulation II. Applications—epilepsy, nerve regeneration, neurotrophins.", Ann NY Acad Sci. 993 (May 2003), 14-24
Astrom, M. , et al., "The effect of cystic cavities on deep brain stimulation in the basal ganglia: a simulation-based study", J Neural Eng., 3(2), (Jun. 2006).132-8
Bazin et al., "Free Software Tools for Atlas-based Volumetric Neuroimage Analysis", Proc. SPIE 5747, Medical Imaging 2005: Image Processing, 1824 May 5, 2005.
Back, C. , et al., "Postoperative Monitoring of the Electrical Properties of Tissue and Electrodes in Deep Brain Stimulation", Neuromodulation, 6(4), (Oct. 2003 ), 248-253
Baker, K. B., et al., "Evaluation of specific absorption rate as a dosimeter of MRI-reiated implant heating", J Magn Reson Imaging., 20(2), (Aug. 2004), 315-20.
Brown, J. "Motor Cortex Stimulation," Neurosurgical Focus ( Sep. 15, 2001) 11(3):E5.
Budai et al., "Endogenous Opioid Peptides Acting at m-Opioid Receptors in the Dorsal Horn Contribute to Midbrain Modulation of Spinal Nociceptive Neurons," Journal of Neurophysiology (1998) 79(2): 677-687.
Cesselin, F. "Opioid and anti-opioid peptides," Fundamental and Clinical Pharmacology (1995) 9(5): 409-33 (Abstract only)
Rezai et al., "Deep Brain Stimulation for Chronic Pain" Surgical Management of Pain, Chapter 44 pp. 565-576 (2002).
Xu, MD., Shi-Ang, article entitled "Comparison of Half-Band and Full-Band Electrodes for Intracochlear Electrical Stimulation", Annals of Otology, Rhinology & Laryngology (Annals of Head & Neck Medicine & Surgery), vol. 102 (5) pp. 363-367 May 1993.
Bedard, C., et al., "Modeling extracellular field potentials and the frequency-filtering properties of extracellular space", Biophys J . . . 86(3). (Mar. 2004), 1829-42.
Benabid, A. L., et al., "Future prospects of brain stimulation", Neurol Res.;22(3), (Apr. 2000), 237-46.
Brummer, S. B., et al., "Electrical Stimulation with Pt Electrodes: II—Estimation of Maximum Surface Redox (Theoretical Non-Gassing) Limits", IEEE Transactions on Biomedical Engineering, vol. BME-24, Issue 5, (Sep. 1977), 440-443.
Butson, Christopher R., et al., "Deep Brain Stimulation of the Subthalamic Nucleus: Model-Based Analysis of the Effects of Electrode Capacitance on the Volume of Activation", Proceedings of the 2nd International IEEE EMBS, (Mar. 16-19, 2005), 196-197.
Mcintyre, Cameron C., et al., "Cellular effects of deep brain stimulation: model-based analysis of activation and inhibition," J Neurophysiol, 91(4) (Apr. 2004), pp. 1457-1469.
Chaturvedi, A., et al., "Subthalamic Nucleus Deep Brain Stimulation: Accurate Axonal Threshold Prediction with Diffusion Tensor Based Electric Field Models", Engineering in Medicine and Biology Society, 2006. EMBS' 06 28th Annual International Conference of the IEEE, IEEE, Piscataway, NJ USA, Aug. 30, 2006.
Butson, Christopher et al., "Predicting the Effects of Deep Brain Stimulation with Diffusion Tensor Based Electric Field Models" Jan. 1, 2001, Medical Image Computing and Computer-Assisted Intervention—Mic CAI 2006 Lecture Notes in Computer Science; LNCS, Springer, Berlin, DE.
Butson, C. R., et al., "Deep brainstimulation interactive visualization system", Society for Neuroscience vol. 898.7 (2005).
Hodaie, M., et al., "Chronic anterior thalamus stimulation for intractable epilepsy," Epilepsia, 43(6) (Jun. 2002), pp. 603-608.
Hoekema, R., et al., "Multigrid solution of the potential field in modeling electrical nerve stimulation," Comput Biomed Res., 31(5) (Oct. 1998), pp. 348-362.
Holsheimer, J., et al., "Identification of the target neuronal elements in electrical deep brain stimulation," Eur J Neurosci., 12(12) (Dec. 2000), pp. 4573-4577.

Jezernik, S., et al., "Neural network classification of nerve activity recorded in a mixed nerve," Neurol Res., 23(5) (Jul. 2001), pp. 429-434.
Jones, DK., et al., "Optimal strategies for measuring diffusion in anisotropic systems by magnetic resonance imaging," Magn. Reson. Med., 42(3) (Sep. 1999), pp. 515-525.
Krack, P., et al., "Postoperative management of subthalamic nucleus stimulation for Parkinson's disease," Mov. Disord., vol. 17(suppl 3) (2002), pp. 188-197.
Le Bihan, D., et al., "Diffusion tensor imaging: concepts and applications," J Magn Reson Imaging, 13(4) (Apr. 2001), pp. 534-546.
Lee, D. C., et al., "Extracellular electrical stimulation of central neurons: quantitative studies," In: Handbook of neuroprosthetic methods, WE Finn and PG Lopresti (eds) CRC Press (2003), pp. 95-125.
Levy, AL., et al., "An Internet-connected, patient-specific, deformable brain atlas integrated into a surgical navigation system," J Digit Imaging, 10(3 Suppl 1) (Aug. 1997), pp. 231-237.
Liu, Haiying, et al., "Intra-operative MR-guided DBS implantation for treating PD and ET," Proceedings of SPIE vol. 4319, Department of Radiology & Neurosurgery, University of Minnesota, Minneapolis, MN 55455 (2001), pp. 272-276.
Mcintyre, C. C., et al., "Extracellular stimulation of central neurons: influence of stimulus waveform and frequency on neuronal output," J. Neurophysiol., 88(4), (Oct. 2002), pp. 1592-1604.
Mcintyre, C. C., et al., "Microstimulation of spinal motoneurons: a model study," Proceedings of the 19th Annual International Conference of the IEEE Engineering in Medicine and Biology society, vol. 5, (1997), pp. 2032-2034.
Mcintyre, Cameron C., et al., "Model-based Analysis of deep brain stimulation of the thalamus," Proceedings of the Second joint EMBS/BM ES Conference, vol. 3, Annual Fall Meeting of the Biomedical Engineering Society (Cal. No. 02CH37392) IEEEPiscataway, NJ (2002), pp. 2047-2048.
Mcintyre, C. C., et al., "Model-based design of stimulus trains for selective microstimulation of targeted neuronal populations," Proceedings of the 23rd Annual International Conference of the IEEE Engineering in Medicine and Biology Society, vol. 1 (2001), pp. 806-809.
Mcintyre, C. C., et al., Model-based design of stimulus waveforms for selective microstimulation in the central nervous system,, Proceedings of the First Joint [Engineering in Medicine and Biology, 1999. 21st Annual Conf. and the 1999 Annual FallMeeting of the Biomedical Engineering Soc.] BM ES/EMBS Conference, vol. 1 (1999), p. 384.
Mcintyre, Cameron C., et al., "Modeling the excitability of mammalian nerve fibers: influence of aflerpotentials on the recovery cycle," J Neurophysiol, 87(2) (Feb. 2002), pp. 995-1006.
Mcintyre, Cameron C., et al., "Selective microstimulation of central nervous system neurons," Annals of biomedical engineering, 28(3) (Mar. 2000), pp. 219-233.
Mcintyre, C. C., et al., "Sensitivity analysis of a model of mammalian neural membrane," Biol Cybern., 79(1) (Jul. 1998), pp. 29-37.
Mcintyre, Cameron C., et al., "Uncovering the mechanism(s) of action of deep brain stimulation: activation, inhibition, or both," Clin Neurophysiol, 115(6) (Jun. 2004), pp. 1239-1248.
Mcintyre, Cameron C., et al., "Uncovering the mechanisms of deep brain stimulation for Parkinson's disease through functional imaging, neural recording, and neural modeling," Crit Rev Biomed Eng., 30(4-6) (2002), pp. 249-281.
Mouine et al. "Multi-Strategy and Multi-Algorithm Cochlear Prostheses", Biomed. Sci. Instrument, 2000; 36:233-238.
Mcintyre, Cameron C., et al., "Electric Field and Stimulating Influence generated by Deep Brain Stimulation of the Subthalamaic Nucleus," Clinical Neurophysiology, 115(3) (Mar. 2004), pp. 589-595.
Mcintyre, Cameron C., et al., "Electric field generated by deep brain stimulation of the subthalamic nucleus," Biomedical Engineering Society Annual Meeting, Nashville TN (Oct. 2003), 16 pages.

(56) References Cited

OTHER PUBLICATIONS

Mcintyre, Cameron C., et al., "Excitation of central nervous system neurons by nonuniform electric fields," Biophys. J., 76(2) (1999), pp. 878-888.
McNeal, DR., et al., "Analysis of a model for excitation of myelinated nerve," IEEE Trans Biomed Eng., vol. 23 (1976), pp. 329-337.
Micheli-Tzanakou, E. , et al., "Computational Intelligence for target assesment in Parkinson's disease," Proceedings of SPIE vol. 4479, Applications and Science of Neural Networks, Fuzzy Systems, and Evolutionary Computation IV (2001 ), pp. 54-69.
Miocinovic, S., et al., "Computational analysis of subthalamic nucleus and lenticular fasciculus activation during therapeutic deep brain stimulation," J Neurophysiol., 96(3) (Sep. 2006), pp. 1569-1580.
Miranda, P. C., et al., "The distribution of currents inducedin the brain by Magnetic Stimulation: a finite element analysis incorporating OT-MRI-derived conductivity data," Proc. Intl. Soc. Mag. Reson. Med. 9 (2001 ), p. 1540.
Miranda, P. C., et al., "The Electric Field Induced in the Brain by Magnetic Stimulation: A 3-D Finite-Element Analysis of the Effect of Tissue Heterogeneity and Anisotropy," IEEE Transactions on Biomedical Enginering, 50(9) (Sep. 2003), pp. 1074-1085.
Moffitt, MA., et al., "Prediction of myelinated nerve fiber stimulation thresholds: limitations of linear models," IEEE Transactions on Biomedical Engineering, 51 (2) (2003), pp. 229-236.
Moro, E, et al., "The impact on Parkinson's disease of electrical parameter settings in STN stimulation," Neurology, 59(5) (Sep. 10, 2002), pp. 706-713.
Nowak, LG., et al., "Axons, but not cell bodies, are activated by electrical stimulation in cortical gray matter. I. Evidence from chronaxie measurements," Exp. Brain Res., 118(4) (Feb. 1998), pp. 477-488.
Nowak, LG., et al., "Axons, but not cell bodies, are activated by electrical stimulation in cortical gray matter. II. Evidence from selective inactivation of cell bodies and axon initial segments," Exp. Brain Res., 118(4) (Feb. 1998), pp. 489-500.
O'Suilleabhain, PE., et al., "Tremor response to polarity, voltage, pulsewidth and frequency of thalamic stimulation," Neurology, 60(5) (Mar. 11, 2003), pp. 786-790.
Pierpaoli, C., et al., "Toward a quantitative assessment of diffusion anisotropy," Magn Reson Med., 36(6) (Dec. 1996), pp. 893-906.
Plonsey, R., et al., "Considerations of quasi-stationarity in electrophysiological systems," Bull Math Biophys., 29(4) (Dec. 1967), pp. 657-664.
Ranck, J B., "Specific impedance of rabbit cerebral cortex," Exp. Neurol., vol. 7 (Feb. 1963), pp. 144-152.
Ranck, J B., et al., "The Specific impedance of the dorsal columns of the cat: an anisotropic medium," Exp. Neurol., 11 (Apr. 1965), pp. 451-463.
Ranck, J B., "Which elements are excited in electrical stimulation of mammalian central nervous system: a review," Brain Res., 98(3) (Nov. 21, 1975), pp. 417-440.
Rattay, F., et al., "A model of the electrically excited human cochlear neuron. I. Contribution of neural substructures to the generation and propagation of spikes," Hear Res., 153(1-2) (Mar. 2001), pp. 43-63.
Rattay, F., "A model of the electrically excited human cochlear neuron. II. Influence of the three-dimensional cochlear structure on neural excitability," Hear Res., 153(1-2) (Mar. 2001), pp. 64-79.
Rattay, F., "Arrival at Functional Electrostimulation by modelling of fiber excitation," Proceedings of the Ninth annual Conference of the IEEE Engineering in Medicine and Biology Society (1987), pp. 1459-1460.
Rattay, F., "The influence of intrinsic noise can preserve the temporal fine structure of speech signals in models of electrically stimulated human cochlear neurones," Journal of Physiology, Scientific Meeting of the Physiological Society, London, England, UK Apr. 19-21, 1999 (Jul. 1999), p. 170P.

Rizzone, M., et al., "Deep brain stimulation of the subthalamic nucleus in Parkinson's disease: effects of variation in stimulation parameters," J. Neurol. Neurosurg. Psychiatry., 71(2) (Aug. 2001), pp. 215-219.
Saint-Cyr, J. A., et al., "Localization of clinically effective stimulating electrodes in the human subthalamic nucleus on magnetic resonance imaging," J. Neurosurg., 87(5) (Nov. 2002), pp. 1152-1166.
Sances, A., et al., "In Electroanesthesia: Biomedical and Biophysical Studies," A Sances and SJ Larson, Eds., Academic Press, NY (1975), pp. 114-124.
Si. Jean, P., et al., "Automated atlas integration and interactive three-dimensional visualization tools for planning and guidance in functional neurosurgery," IEEE Transactions on Medical Imaging, 17(5) (1998), pp. 672-680.
Starr, P.A., et al., "Implantation of deep brain stimulators into the subthalamic nucleus: technical approach and magnetic resonance imaging-verified lead locations," J. Neurosurg., 97(2) (Aug. 2002), pp. 370-387.
Sterio, D., et al., "Neurophysiological refinement of subthalamic nucleus targeting," Neurosurgery, 50(1) (Jan. 2002), pp. 58-69.
Struijk, J. J., et al., "Excitation of dorsal root fibers in spinal cord stimulation: a theoretical study," IEEE Transactions on Biomedical Engineering, 40(7) (Jul. 1993), pp. 632-639.
Struijk, J J., et al., "Recruitment of dorsal column fibers in spinal cord stimulation: influence of collateral branching," IEEE Transactions on Biomedical Engineering, 39(9) (Sep. 1992), pp. 903-912.
Tamma, F., et al., "Anatomo-clinical correlation of intraoperative stimulation-induced side-effects during HF-DBS of the subthalamic nucleus," Neurol Sci., vol. 23 (Suppl 2) (2002), pp. 109-110.
Tarler, M., et al., "Comparison between monopolar and tripolar configurations in chronically implanted nerve cuff electrodes," IEEE 17th Annual Conference Engineering in Medicine and Biology Society, vol. 2 (1995), pp. 1093-1109.
Testerman, Roy L., "Coritical response to callosal stimulation: a model for determining safe and efficient stimulus parameters," Annals of Biomedical Engineering, 6(4) (1978), pp. 438-452.
Tuch, D.S., et al., "Conductivity mapping of biological tissue using diffusion MRI," Ann NY Acad Sci., 888 (Oct. 30, 1999), pp. 314-316.
Tuch, D.S., et al., "Conductivity tensor mapping of the human brain using diffusion tensor MRI," Proc Nall Acad Sci USA, 98(20) (Sep. 25, 2001), pp. 11697-11701.
Veraart, C., et al., "Selective control of muscle activation with a multipolar nerve cuff electrode," IEEE Transactions on Biomedical Engineering, 40(7) (Jul. 1993), pp. 640-653.
Vercueil, L., et al., "Deep brain stimulation in the treatment of severe dystonia," J. Neurol., 248(8) (Aug. 2001 ), pp. 695-700.
Vilalte, "Circuit Design of the Power-on-Reset," Apr. 2000, pp. 1-25.
Vitek, J. L., "Mechanisms of deep brain stimulation: excitation or inhibition," Mov. Disord., vol. 17 (Suppl. 3) (2002), pp. 69-72.
Voges, J., et al., "Bilateral high-frequency stimulation in the subthalamic nucleus for the treatment of Parkinson disease: correlation of therapeutic effect with anatomical electrode position," J. Neurosurg., 96(2) (Feb. 2002), pp. 269-279.
Wakana, S., et al., "Fiber tract-based atlas of human white matter anatomy," Radiology, 230(1) (Jan. 2004), pp. 77-87.
Alexander, DC., et al., "Spatial transformations of diffusion tensor magnetic resonance images," IEEE Transactions on Medical Imaging, 20 (11), (2001), pp. 1131-1139.
Wu, Y. R., et al., "Does Stimulation of the GPi control dyskinesia by activating inhibitory axons?," Mov. Disord., vol. 16 (2001), pp. 208-216.
Yelnik, J., et al., "Localization of stimulating electrodes in patients with Parkinson disease by using a three-dimensional atlas-magnetic resonance imaging coregistration method," J Neurosurg., 99(1) (Jul. 2003), pp. 89-99.
Yianni, John, et al., "Globus pallidus internus deep brain stimulation for dystonic conditions: a prospective audit," Mov. Disord., vol. 18 (2003), pp. 436-442.

(56) References Cited

OTHER PUBLICATIONS

Zonenshayn, M., et al., "Comparison of anatomic and neurophysiological methods for subthalamic nucleus targeting," Neurosurgery, 47(2) (Aug. 2000), pp. 282-294.
Voghell et al., "Programmable Current Source Dedicated to Implantable Microstimulators" ICM '98 Proceedings of the Tenth International Conference, pp. 67-70.
Butson, Christopher R., et al., "Patient-specific analysis of the volume of tissue activated during deep brain stimulation", NeuroImage. vol. 34. (2007), 661-670.
Adler, DE., et al., "The tentorial notch: anatomical variation, morphometric analysis, and classification in 100 human autopsy cases," J. Neurosurg., 96(6), (Jun. 2002), pp. 1103-1112.
Jones et al., "An Advanced Demultiplexing System for Physiological Stimulation", IEEE Transactions on Biomedical Engineering, vol. 44 No. 12 Dec. 1997, pp. 1210-1220.
Alo, K. M., et al., "New trends in neuromodulation for the management of neuropathic pain," Neurosurgery, 50(4), (Apr. 2002), pp. 690-703, discussion pp. 703-704.
Ashby, P., et al., "Neurophysiological effects of stimulation through electrodes in the human subthalamic nucleus," Brain, 122 (PI 10), (Oct. 1999), pp. 1919-1931.
Baker, K. B., et al., "Subthalamic nucleus deep brain stimulus evoked potentials: Physiological and therapeutic implications," Movement Disorders, 17(5), (Sep./Oct. 2002), pp. 969-983.
Bammer, R, et al., "Diffusion tensor imaging using single-shot SENSE-EPI", Magn Reson Med., 48(1 ), (Jul. 2002), pp. 128-136.
Basser, P.J., et al., "MR diffusion tensor spectroscopy and imaging," Biophys J., 66(1 ), (Jan. 1994), pp. 259-267.
Basser, P J., et al., "New currents in electrical stimulation of excitable tissues," Annu Rev Biomed Eng., 2, (2000), pp. 377-397.
Benabid, AL., et al., "Chronic electrical stimulation of the ventralis intermedius nucleus of the thalamus as a treatment of movement disorders," J. Neurosurg., 84(2), (Feb. 1996), pp. 203-214.
Benabid, AL., et al., "Combined (Ihalamotoy and stimulation) stereotactic surgery of the VIM thalamic nucleus for bilateral Parkinson disease," Appl Neurophysiol, vol. 50, (1987), pp. 344-346.
Benabid, A L., et al., "Long-term suppression of tremor by chronic stimulation of the ventral intermediate thalamic nucleus," Lancet, 337 (8738), (Feb. 16, 1991 ), pp. 403-406.
Butson, C. R., et al., "Predicting the effects of deep brain stimulation with diffusion tensor based electric field models," Medical Image Computing and Computer-Assisted Intervention—Mic Cai 2006, Lecture Notes in Computer Science (LNCS), vol. 4191, pp. 429-437, LNCS, Springer, Berlin, DE.
Christensen, Gary E., et al., "Volumetric transformation of brain anatomy," IEEE Transactions on Medical Imaging, 16(6), (Dec. 1997), pp. 864-877.
Cooper, S , et al., "Differential effects of thalamic stimulation parameters on tremor and paresthesias in essential tremor," Movement Disorders, 17(Supp. 5), (2002), p. S193.
Coubes, P, et al., "Treatment of DYT1-generalised dystonia by stimulation of the internal globus pallidus," Lancet, 355 (9222), (Jun. 24, 2000), pp. 2220-2221.
Dasilva, A.F. M., et al., "A Primer Diffusion Tensor Imaging of Anatomical Substructures," Neurosurg. Focus; 15(1) (Jul. 2003), pp. 1-4.
Dawant, B. M., et al., "Compuerized atlas-guided positioning of deep brain stimulators: a feasibility study," Biomedical Image registration, Second International Workshop, WBIR 2003, Revised Papers (Lecture notes in Comput. Sci. vol. (2717), Springer-Verlag Berlin, Germany(2003), pp, 142-150.
Finnis, K. W., et al., "3-D functional atalas of subcortical structures for image guided stereotactic neurosurgery," Neuroimage, vol. 9, No. 6, Iss. 2 (1999), p. S206.
Finnis. K. W., et al., "3D Functional Database of Subcortical Structures for Surgical Guidance in Image Guided Stereotactic Neurosurgery," Medical Image Computing and Computer-Assisted Intervention—MICCAI'99, Second International Conference. Cambridge, UK, Sep. 19-22, 1999, Proceedings (1999), pp. 758-767.
Finnis, K. W., et al., "A 3-Dimensional Database of Deep Brain Functional Anatomy, and Its Application to Image-Guided Neurosurgery," Proceedings of the Third International Conference on Medical Image Computing and Computer-Assisted Intervention. Lecture Notes in Computer Science; vol. 1935 (2000), pp. 1-8.
Finnis, K. W., et al., "A functional database for guidance of surgical and therapeutic procedures in the deep brain," Proceedings of the 22nd Annual International Conference of the IEEE Engineering in Medicine and Biology Society, vol. 3 (2000), pp. 1787-1789.
Finnis, K. W., et al., "Application of a Population Based Electrophysiological Database to the Planning and Guidance of Deep Brain Stereotactic Neurosurgery," Proceedings of the 5th International Conference on Medical Image Computing and Computer-Assisted Intervention—Part 11, Lecture Notes in Computer Science; vol. 2489 (2002), pp. 69-76.
Finnis, K. W., et al., "Subcortical physiology deformed into a patient-specific brain atlas for image-guided stereotaxy," Proceedings of SPIE—vol. 4681 Medical Imaging 2002: Visualization, Image-Guided Procedures, and Display (May 2002), pp. 184-195.
Finnis, Krik W., et al., "Three-Dimensional Database of Subcortical Electrophysiology for Image-Guided Stereotatic Functional Neurosurgery," IEEE Transactions on Medical Imaging, 22(1) (Jan. 2003), pp. 93-104.
Gabriels, L , et al., "Deep brain stimulation for treatment-refractory obsessive-compulsive disorder: psychopathological and neuropsychological outcome in three cases," Acta Psychiatr Scand., 107(4) (2003), pp. 275-282.
Gabriels, LA., et al., "Long-term electrical capsular stimulation in patients with obsessive-compulsive disorder," Neurosurgery, 52(6) (Jun. 2003), pp. 1263-1276.
Goodall, E. V., et al., "Modeling study of activation and propagation delays during stimulation of peripheral nerve fibers with a tripolar cuff electrode," IEEE Transactions on Rehabilitation Engineering, [see also IEEE Trans. on Neural Systems and Rehabilitation], 3(3) (Sep. 1995), pp. 272-282.
Goodall, E. V., et al., "Position-selective activation of peripheral nerve fibers with a cuff electrode," IEEE Transactions on Biomedical Engineering, 43(8) (Aug. 1996), pp. 851-856.
Goodall, E. V., "Simulation of activation and propagation delay during tripolar neural stimulation," Proceedings of the 15th Annual International Conference of the IEEE Engineering in Medicine and Biology Society (1993), pp. 1203-1204.
Grill, WM., "Modeling the effects of electric fields on nerve fibers: influence of tissue electrical properties," IEEE Transactions on Biomedical Engineering, 46(8) (1999), pp. 918-928.
Grill, W. M., et al., "Neural and connective tissue response to long-term implantation of multiple contact nerve cuff electrodes," J Biomed Mater Res., 50(2) (May 2000), pp. 215-226.
Grill, W. M., "Neural modeling in neuromuscular and rehabilitation research," Proceedings of the 23rd Annual International Conference of the IEEE Engineering in Medicine and Biology Society, vol. 4 (2001 ), pp. 4065-4068.
Grill, W. M., et al., "Non-invasive measurement of the input-output properties of peripheral nerve stimulating electrodes," Journal of Neuroscience Methods, 65(1) (Mar. 1996), pp. 43-50.
Grill, W. M., et al., "Quantification of recruitment properties of multiple contact cuff electrodes," IEEE Transactions on Rehabilitation Engineering, [see also IEEE Trans. on Neural Systems and Rehabilitation], 4(2) (Jun. 1996), pp. 49-62.
Grill, W. M., "Spatially selective activation of peripheral nerve for neuroprosthetic applications," Ph.D. Case Western Reserve University, (1995), pp. 245 pages.
Grill, W. M., "Stability of the input-output properties of chronically implanted multiple contact nerve cuff stimulating electrodes," IEEE Transactions on Rehabilitation Engineering [see also IEEE Trans. on Neural Systems and Rehabilitation] (1998), pp. 364-373.
Grill, W. M., "Stimulus waveforms for selective neural stimulation," IEEE Engineering in Medicine and Biology Magazine, 14(4) (Jul.-Aug. 1995), pp. 375-385.

(56) References Cited

OTHER PUBLICATIONS

Grill, W. M., et al., "Temporal stability of nerve cuff electrode recruitment properties," IEEE 17th Annual Conference Engineering in Medicine and Biology Society, vol. 2 (1995), pp. 1089-1090.
Gross, RE., et al., "Advances in neurostimulation for movement disorders," Neurol Res., 22(3) (Apr. 2000), pp. 247-258.
Guridi et al., "The subthalamic nucleus, hemiballismus and Parkinson's disease: reappraisal of a neurological dogma," Brain, vol. 124, 2001, pp. 5-19.
Haberler, C, et al., "No tissue damage by chronic deep brain stimulation in Parkinson's disease," Ann Neurol., 48(3) (Sep. 2000), pp. 372-376.
Hamel, W, et al., "Deep brain stimulation of the subthalamic nucleus in Parkinson's disease: evaluation of active electrode contacts," J Neurol Neurosurg Psychiatry, 74(8) (Aug. 2003), pp. 1036-1046.
Hanekom, "Modelling encapsulation tissue around cochlear implant electrodes," Med. Biol. Eng. Comput. vol. 43 (2005), pp. 47-55.
Haueisen, J , et al., "The influence of brain tissue anisotropy on human EEG and MEG," Neuroimage, 15(1) (Jan. 2002), pp. 159-166.
D'Haese et al. Medical Image Computing and Computer-Assisted Intervention—MICCAI 2005 Lecture Notes in Computer Science, 2005, vol. 3750, 2005, 427-434.
Rohde et al. IEEE Transactions on Medical Imaging, vol. 22 No. 11, 2003 p. 1470-1479.
Dawant et al., Biomedical Image Registration. Lecture Notes in Computer Science, 2003, vol. 2717, 2003, 142-150.
Miocinovic et al., "Stereotactiv Neurosurgical Planning, Recording, and Visualization for Deep Brain Stimulation in Non-Human Primates", Journal of Neuroscience Methods, 162:32-41, Apr. 5, 2007, XP022021469.
Gemmar et al., "Advanced Methods for Target Navigation Using Microelectrode Recordings in Stereotactic Neurosurgery for Deep Brain Stimulation", 21st IEEE International Symposium on Computer-Based Medical Systems, Jun. 17, 2008, pp. 99-104, XP031284774.
Acar et al., "Safety Anterior Commissure-Posterior Commissure-Based Target Calculation of the Subthalamic Nucleus in Functional Stereotactic Procedures", Stereotactic Funct. Neurosura., 85:287-291, Aug. 2007.
Andrade-Souza, "Comparison of Three Methods of Targeting the Subthalamic Nucleus for Chronic Stimulation in Parkinson's Disease", Neurosurgery, 56:360-368, Apr. 2005.
Anheim et al., "Improvement in Parkinson Disease by Subthalamic Nucleus Stimulation Based on Electrode Placement", Arch Neural., 65:612-616, May 2008.
Butson et al., "Tissue and Electrode Capacitance Reduce Neural Activation Volumes During Deep Brain Stimulation", Clinical Neurophysiology, 116:2490-2500, Oct. 2005.
Butson et al., "Sources and Effects of Electrode Impedance During Deep Brain Stimulation", Clinical Neurophysiology, 117:44 7-454, Dec. 2005.
D'Haese et al., "Computer-Aided Placement of Deep Brain Stimulators: From Planning to Intraoperative Guidance", IEEE Transaction on Medical Imaging, 24:1469-1478, Nov. 2005.
Gross et al., "Electrophysiological Mapping for the Implantation of Deep Brain Stimulators for Parkinson's Disease and Tremor", Movement Disorders, 21 :S259-S283, Jun. 2006.
Halpern et al., "Brain Shift During Deep Brain Stimulation Surgery for Parkinson's Disease", Stereotact Funct. Neurosurg., 86:37-43, published online Sep. 2007.
Herzog et al., "Most Effective Stimulation Site in Subthalamic Deep Brain Stimulation for Parkinson's Disease", Movement Disorders, 19:1050-1099, published on line Mar. 2004.
Jeon et al., A Feasibility Study of Optical Coherence Tomography for Guiding Deep Brain Probes, Journal of Neuroscience Methods, 154:96-101, Jun. 2006.
Khan et al., "Assessment of Brain Shift Related to Deep Brain Stimulation Surgery", Sterreotact Funct. Neurosurg., 86:44-53, published online Sep. 2007.
Koop et al., "Improvement in a Quantitative Measure of Bradykinesia After Microelectrode Recording in Patients with Parkinson's Disease During Deep Brain Stimulation Surgery", Movement Disorders, 21 :673-678, published on line Jan. 2006.
Lemaire et al., "Brain Mapping in Stereotactic Surgery: a Brief Overview from the Probabilistic Targeting to the Patient-Based Anatomic Mapping", NeuroImage, 37:S109-S115, available online Jun. 2007.
Machado et al., "Deep Brain Stimulation for Parkinson's Disease: Surgical Technique and Perioperative Management", Movement Disorders, 21 :S247-S258, Jun. 2006.
Maks et al., "Deep Brain Stimulation Activation Volumes and Their Association with Neurophysiological Mapping and Therapeutic Outcomes", Downloaded from jnnp.bmj.com, pp. 1-21, published online Apr. 2008.
Moran et al., "Real-Time Refinment of Subthalamic Nucleous Targeting Using Bayesian Decision-Making on the Root Mean Square Measure", Movement Disorders, 21: 1425-1431, published online Jun. 2006.
Sakamoto et al., "Homogeneous Fluorescence Assays for RNA Diagnosis by Pyrene-Conjugated 2'-0-Methyloligoribonucleotides", Nucleosides, Nucleotides, and Nucleric Acids, 26:1659-1664, on line publication Oct. 2007.
Winkler et al., The First Evaluation of Brain Shift During Functional Neurosurgery by Deformation Field Analysis, J. Neural. Neurosurg. Psychiatry, 76:1161-1163, Aug. 2005.
Yelnik et al., "A Three-Dimensional, Histological and Deformable Atlas of the Human Basal J Ganglia. I. Atlas Construction Based on Immunohistochemical and MRI Data", NeuroImage, 34:618,-638, Jan. 2007.
Ward, H. E., et al., "Update on deep brain stimulation for neuropsychiatric disorders," Neurobiol Dis 38 (3) (2010), pp, 346-353.
Alberts et al. "Bilateral subthalamic stimulation impairs cognitive-motor performance in Parkinson's disease patients." Brain (2008), 131, 3348-3360, Abstract.
Butson, Christopher R., et al., "Sources and effects of electrode impedance during deep brain stimulation", Clinical Neurophysiology. vol. 117.(2006), 447-454.
An, et al., "Prefronlal cortical projections to longitudinal columns in the midbrain periaqueductal gray in macaque monkeys," J Comp Neural 401 (4) (1998), pp. 455-479.
Bulson, C. R., et al., "Tissue and electrode capacitance reduce neural activation volumes during deep brain stimulation," Clinical Neurophysiology, vol. 116 (2005), pp. 2490-2500.
Carmichael, S. T., et al., "Connectional networks within the orbital and medial prefronlal cortex of macaque monkeys," J Comp Neural 371 (2) (1996), pp. 179-207.
Croxson, et al., "Quantitative investigation of connections of the prefronlal cortex in the human and macaque using probabilistic diffusion tractography," J Neurosci 25 (39) (2005), pp. 8854-8866.
Frankemolle, et al., "Reversing cognitive-motor impairments in Parkinson's disease patients using a computational modelling approach to deep brain stimulation programming," Brain 133 (2010), pp. 746-761.
Freedman, et al., "Subcortical projections of area 25 (subgenual cortex) of the macaque monkey," J Comp Neurol 421 (2) (2000), pp. 172-188.
Giacobbe, et al., "Treatment resistant depression as a failure of brain homeostatic mechanisms: implications for deep brain stimulation," Exp Neural 219 (1) (2009), pp. 44-52.
Goodman, et al., "Deep brain stimulation for intractable obsessive compulsive disorder: pilot study using a blinded, staggered-onset design," Biol Psychiatry 67 (6) (2010), pp. 535-542.
Greenberg, et al., "Deep brain stimulation of the ventral internal capsule/ventral striatum for obsessive-compulsive disorder: worldwide experience," Mol Psychiatry 15 (1) (2010), pp. 64-79.
Greenberg. et al., "Three-year outcomes in deep brain stimulation for highly resistant obsessive-compulsive disorder," Neuropsychopharmacology 31 (11) (2006), pp. 2384-2393.
Gutman, et al., "A tractography analysis of two deep brain stimulation white matter targets for depression," Biol Psychiatry 65 (4) (2009), pp. 276-282.

(56) References Cited

OTHER PUBLICATIONS

Haber, et al., "Reward-related cortical inputs define a large striatal region in primates that interface with associative cortical connections, providing a substrate for incentive-based learning," J Neurosci 26 (32) (2006), pp. 8368-8376.
Haber, et al., "Cognitive and limbic circuits that are affected by deep brain stimulation," Front Biosci 14 (2009), pp. 1823-1834.
Hines, M. L., et al., "The Neuron simulation environment," Neural Comput., 9(6) (Aug. 15, 1997), pp. 1179-1209.
Hua, et al., "Tract probability maps in stereotaxic spaces: analyses of white matter anatomy and tract-specific quantification," Neuroimage 39 (1) (2008), pp. 336-347.
Johansen-Berg, et al., "Anatomical connectivity of the subgenual cingulate region targeted with deep brain stimulation for treatment-resistant depression," Cereb Cortex 18 (6) (2008), pp. 1374-1383.
Kopell, et al., "Deep brain stimulation for psychiatric disorders," J Clin Neurophysiol 21 (1) (2004), pp. 51-67.
Lozano, et al., "Subcallosal cingulate gyrus deep brain stimulation for treatment-resistant depression," Biol Psychiatry 64 (6) (2008), pp. 461-467.
Lujan, et al., "Tracking the mechanisms of deep brain stimulation for neuropsychiatric disorders," Front Biosci 13 (2008), pp. 5892-5904.
Lujan, J.L. et al., "Automated 3-Dimensional Brain Atlas Fitting to Microelectrode Recordings from Deep Brain Stimulation Surgeries," Stereotact. Funel. Neurosurg. 87(2009), pp. 229-240.
Machado, et al., "Functional topography of the ventral striatum and anterior limb of the internal capsule determined by electrical stimulation of awake patients," Clin Neurophysiol 120 (11) (2009), pp. 1941-1948.
Malone, et al., "Deep brain stimulation of the ventral capsule/ventral striatum for treatment-resistant depression," Biol Psychiatry 65 (4) (2009), pp. 267-275.
Mayberg, H. S., et al., "Deep brain stimulation for treatment-resistant depression," Neuron, 45(5) (Mar. 3, 2005), pp. 651-660.
Mayberg, H. S., et al., "Limbic-cortical dysregulation: a proposed model of depression," J Neuropsychiatry Clin Neurosci. 9 (3) (1997), pp. 471-481.
McIntyre, C. C., et al., "Network perspectives on the mechanisms of deep brain stimulation," Neurobiol Dis 38 (3) (2010), pp. 329-337.
Miocinovic, S., et al., "Experimental and theoretical characterization of the voltage distribution generated by deep brain stimulation," Exp Neurol 216 (i) (2009), pp. 166-176.
Nuttin, et al., "Electrical stimulation in anterior limbs of internal capsules in patients with obsessive-compulsive disorder," Lancet 354 (9189) (1999), p. 1526.
Saxena, et al., "Cerebral glucose metabolism in obsessive-compulsive hoarding," Am J Psychiatry. 161 (6) (2004), pp. 1038-1048.
Viola, et al., "Importance-driven focus of attention," IEEE Trans Vis Comput Graph 12 (5) (2006), pp. 933-940.
Wakana, S., et al., "Reproducibility of quantitative tractography methods applied to cerebral white matter," Neuroimage 36 (3) (2007), pp. 630-644.
Mayr et al., "Basic Design and Construction of the Vienna FES Implants: Existing Solutions and Prospects for New Generations of Implants", Medical Engineering & Physics, 2001; 23:53-60.
Mcintyre, Cameron, et al., "Finite element analysis of the current-density and electric field generated by metal microelectrodes", Ann Biomed Eng . 29(3), (2001 ), 227-235.
Foster, K. R., et al., "Dielectric properties of tissues and biological materials: a critical review.", Grit Rev Biomed Ena. 17(1 ). {1989), 25-104.
Limousin, P., et al., "Electrical stimulation of the subthalamic nucleus in advanced Parkinson's disease", N Engl J Med . . . 339(16), (Oct. 15, 1998), 1105-11.
Kitagawa, M., et al., "Two-year follow-up of chronic stimulation of the posterior subthalamic white matter for tremor-dominant Parkinson's disease.", Neurosurgery. 56(2). (Feb. 2005), 281-9.
Johnson, M. D., et al., "Repeated voltage biasing improves unit recordings by reducing resistive tissue impedances", IEEE Transactions on Neural Systems and Rehabilitation Engineering, [see also IEEE Trans. on Rehabilitation Engineering (2005), 160-165.
Holsheimer, J. , et al., "Chronaxie calculated from current-duration and voltage-duration data", J Neurosci Methods. 97(1). (Apr. 1, 2000), 45-50.
Hines, M. L., et al., "The Neuron simulation environment", Neural Comput. 9(6). (Aug. 15, 1997), 1179-209.
Herzog, J., et al., "Most effective stimulation site in subthalamic deep brain stimulation for Parkinson's disease", Mov Disord. 19(9). (Sep. 2004), 1050-4.
Hershey, T., et al., "Cortical and subcortical blood flow effects of subthalamic nucleus stimulation in PD.", Neurology 61(6). (Sep. 23, 2003), 816-21.
Hemm, S. , et al., "Evolution of Brain Impedance in Dystonic Patients Treated by GPi Electrical Stimulation", Neuromodulation 7(2) (Apr. 2004), 67-75.
Hemm, S., et al., "Deep brain stimulation in movement disorders: stereotactic coregistration of two-dimensional electrical field modeling and magnetic resonance imaging.", J Neurosurg. 103(6): (Dec. 2005), 949-55.
Haueisen, J, et al., "The influence of brain tissue anisotropy on human EEG and MEG", Neuroimage 15(1) (Jan. 2002), 159-166.
Haslinger, B., et al., "Frequency-correlated decreases of motor cortex activity associated with subthalamic nucleus stimulation in Parkinson's disease.", Neuroimage 28(3). (Nov. 15, 2005), 598-606.
Hashimoto, T. , et al., "Stimulation of the subthalamic nucleus changes the firing pattern of pallidal neurons", J Neurosci. 23(5). (Mar. 1, 2003), 1916-23.
Hardman, C. D., et al., "Comparison of the basal ganglia in rats, marmosets, macaques, baboons, and humans: volume and neuronal number for the output, internal relay, and striatal modulating nuclei", J Comp Neurol., 445(3). (Apr. 8, 2002), 238-55.
McNaughtan et al., "Electrochemical Issues in Impedance Tomography", 1st World Congress on Industrial Process Tomography, Buxton, Greater Manchester, Apr. 14-17, 1999.
Grill, WM., et al., "Electrical properties of implant encapsulation tissue", Ann Biomed Eng. vol. 22. (1994), 23-33.
Grill, W. M., et al., "Deep brain stimulation creates an informational lesion of the stimulated nucleus", Neuroreport. 15I7t (May 19, 2004 ), 1137-40.
U.S. Appl. No. 62/480,942, filed Apr. 3, 2017.
Pulliam CL, Heldman DA, Orcutt TH, Mera TO, Giuffrida JP, Vitek JL. Motion sensor strategies for automated optimization of deep brain stimulation in Parkinson's disease. Parkinsonism Relat Disord. Apr. 2015; 21(4):378-82.
International Search Report and Written Opinion for PCT/US2017/056664 dated Feb. 7, 2018.
Official Communication for U.S. Appl. No. 15/783,961 dated Sep. 19, 2019.

\* cited by examiner

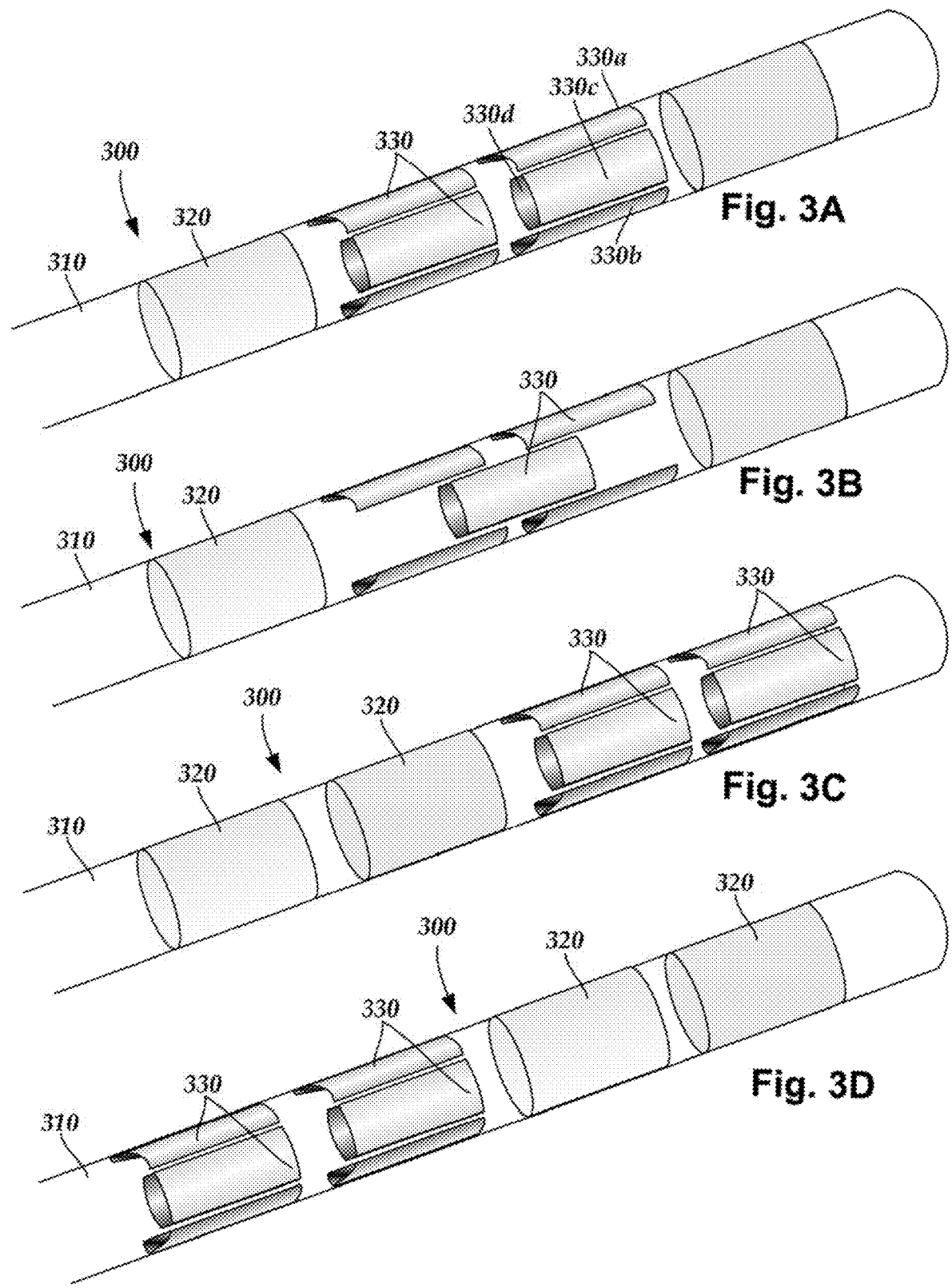

Form is filed out – in this example an optimal contact location is randomly chosen near the $5^{th}$ contact location with an optimal amplitude of 4.2 mA. The noise level is 10% (response is measured on a 0 to 4 scale).

Fig. 6B

Matrix X

| 3 | 6 | 8 | 5.2 | ... |
|---|---|---|-----|-----|
| 2 | 2 | 0 | 0.7 | ... |

| 2 | 1.7 | 2.4 | 2.1 | ... |
|---|-----|-----|-----|-----|

Vector y

*Fig. 9*

SYSTEMS AND METHODS FOR CLOSED-LOOP DETERMINATION OF STIMULATION PARAMETER SETTINGS FOR AN ELECTRICAL SIMULATION SYSTEM

CROSS-REFERENCE TO RELATED APPLICATIONS

This application is a continuation of U.S. patent application Ser. No. 15/783,961, filed Oct. 13, 2017, which claims the benefit under 35 U.S.C. § 119(e) of U.S. Provisional Patent Application Ser. No. 62/408,399, filed Oct. 14, 2016, and U.S. Provisional Patent Application Ser. No. 62/545,819, filed Aug. 15, 2017, all of which are incorporated herein by reference.

FIELD

The present invention is directed to the area of implantable electrical stimulation systems and methods of making and using the systems. The present invention is also directed to systems and methods for facilitating determining and setting of stimulation parameters for programming an electrical stimulation system.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Stimulation of the brain, such as deep brain stimulation, can be used to treat a variety of diseases or disorders.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is a system facilitating programming settings of an implantable pulse generator associated with a patient using closed loop programming, the system including a computer processor and a memory which stores a pulse generator feedback control logic. The pulse generator feedback logic is executed by the processor to interface with control instructions of an implantable pulse generator by the following actions: incorporating one or more machine learning engines, automatically generating a proposed set of stimulation parameter values that each affect a stimulation aspect of the IPG; forwarding the automatically generated proposed set of stimulation parameter values to configure stimulation parameters of the IPG accordingly; receiving one or more clinical response values as a result of the IPG being configured to the proposed set of stimulation parameter values; automatically generating, by incorporating one or more machine learning engines, a revised proposed set of stimulation parameter values taking into account the received clinical response values; forwarding the revised proposed set to configure stimulation parameters of the IPG to the revised proposed set of stimulation parameter values; and repeating the receiving one or more clinical response values as a result of the IPG being configured to the revised proposed set, automatically generating, by incorporating one or more machine learning engines, a revised proposed set of stimulation parameter values, and forwarding the revised prosed set of stimulation parameters to configure stimulation parameters of the IPG accordingly, until or unless a stop condition has been reached or the one or more received clinical response values indicates a value that corresponds to a therapeutic response indication within a designated tolerance.

In at least some embodiments of the system, the IPG is a deep brain stimulator.

In at least some embodiments of the system, the stimulation parameter values that each affect a stimulation aspect of the IPG include one or more of: electrode determination, amplitude of current, frequency of current, pulse width, spread and/or foci of stimulation, and/or geometry of stimulated tissue In at least some embodiments of the system, at least one stimulation parameter indicates a location of an electrode disposed on a lead of the electrical stimulator. In some of these embodiments, the electrode is a ring electrode or a segmented electrode.

In at least some embodiments of the system, at least one stimulation parameter indicates a location of an electrode that results in current being confined to a single direction.

In at least some embodiments of the system, the one or more clinical response values are automatically received from a sensor associated with the patient. In at least some of these embodiments, receiving the clinical response values from the sensors allows the programming of the IPG to be automated or at least semi-automated so that a clinician does not need to be present to program the IPG.

In at least some embodiments of the system, the pulse generator feedback control logic incorporates multiple machine learning techniques to automatically generate the proposed set of stimulation parameter values and/or the revised proposed set of stimulation parameter values. In at least some of these embodiments the machine learning techniques are deployed simultaneously. In at least some embodiments the multiple learning techniques are rated (or ranked) automatically based upon ability to generate a set of stimulation parameter values that corresponds to the therapeutic response indication within the designated tolerance or based upon other metrics. These ratings may change within a stimulation parameter setting or between different sessions.

In at least some embodiments of the system, the automatically generating, by incorporating one or more machine learning engines, a revised proposed set of stimulation parameter values further comprises, using the one or more machine learning engines, automatically generating one or more predicted therapeutic response values for a plurality of values of the plurality of stimulation parameters of the IPG for which a clinical response value has not yet been received; and automatically selecting a revised proposed set of stimulation parameter values to configure the IPG based in part on at least one of the predicted therapeutic response values. In at least some of these embodiments, multiple machine learning engines are deployed to generate multiple predications of the one or more predicted therapeutic response values. In at least some of these embodiments, the revised proposed set of stimulation parameter values to configure the IPG takes into account at least one of the predicted therapeutic response values to determine a next set of stimulation parameter values to try.

In at least some embodiments of the system, the automatically generating the revised proposed set of values of the plurality of stimulation parameters is based upon one or more rules. In at least some of these embodiments, the rules rank the remaining possible proposed sets of values. In at least some of these embodiments, the rules include at least one of: a rule based upon retrying locations within a number of iterations, a rule based upon mathematical proximity of proposed sets of stimulation parameter values to sets of stimulation parameter values already tested, a rule based upon values of a stimulation parameter leading to adverse side effects, and/or a rule based upon size of step between values of a same stimulation parameter.

In at least some embodiments of the system, the receiving one or more clinical response values as a result of the IPG being configured to the proposed set of stimulation parameter values indicates whether an undesired side effect has occurred.

In at least some embodiments of the system, the revised proposed set of stimulation parameter values are determined in each subsequent iteration in contact order, wherein contact order means testing along a first contact until side effects are prohibitive before testing a next proximal contact on a lead. In at least some embodiments of the system, the revised proposed set of stimulation parameter values are determined in each subsequent iteration by selectively choosing contacts along the main axis of a lead and varying other stimulation parameters for each selectively chosen contact.

In at least some embodiments of the system, the revised proposed set of stimulation parameter values are determined in each subsequent iteration randomly, based upon a model of the patient, a spatial search algorithm, or by varying size of jump to a revised proposed set of stimulation parameter values. In other embodiments, the revised proposed set of stimulation parameter values may be determined using other techniques or rules.

Another embodiment is a method for facilitating programming settings of an electrical stimulator associated with a patient using closed loop programming that includes: receiving an indication of a plurality of stimulation parameters and an indication of a desired therapeutic response value; automatically generating an initial proposed set of stimulation parameter values for testing the electrical stimulator programmed according to these initial values; receiving an indication of clinical results based upon testing the programmed electrical stimulator on a recipient, wherein the received indication indicates a therapeutic response value; automatically generating, using machine learning, one or more predicted therapeutic response values for a plurality of values of the plurality of stimulation parameters for which an indication of clinical results has not yet been received; automatically generating and indicating a next proposed set of stimulation parameter values for testing the electrical stimulator programmed accordingly, based in part on at least one of the predicted therapeutic response values; and repeating the acts of receiving the indication of clinical results based upon testing the programmed electrical simulator, automatically generating using machine learning the one or more predicted therapeutic response values, and automatically generating and indicating a next proposed set of stimulation parameter values for testing the electrical stimulator programmed accordingly, until or unless a stop condition has been reached or the received indication of clinical results indicates a therapeutic response value that is within a designated tolerance.

In some embodiments of the method, electrical stimulator is an implantable pulse generator. In some embodiments of the method, at least one stimulation parameter indicates a location of an electrode disposed on a lead of the electrical stimulator. In some embodiments of the method, the electrode is a ring electrode or a segmented electrode. In some embodiments of the method, at least one stimulation parameter results in current stimulation in multiples directions at once. In some embodiments of the method, at least one stimulation parameter indicates a location of an electrode that results in current being confined to a single direction.

In at least some embodiments of the method, the plurality of stimulation parameter values includes one or more of: electrode location, amplitude of current, frequency of current, pulse width, spread of stimulation, and/or geometry of stimulated tissue.

In at least some embodiments of the method, the receiving the indication of clinical results based upon testing the recipient with an electrical stimulator indicates whether an undesired side effect has occurred.

In at least some embodiments of the method, the automatically generating, using machine learning, one or more predicted therapeutic response values for a plurality of values of the plurality of stimulation parameters for which an indication of clinical results has not yet been received uses a training data set based upon prior data of the recipient or of other recipients.

In at least some embodiments of the method, the indication of clinical results based upon testing the electrical stimulator on a recipient is received from a data repository.

In at least some embodiments of the method, the initial proposed set of stimulation parameter values is determined using data collected in prior electrical simulator programming sessions.

In at least some embodiments of the method, multiple machine learning techniques are deployed simultaneously to generate multiple predictions of the one or more predicted therapeutic response values and the multiple machine learning techniques are rated automatically based upon ability to provide an accurate prediction of a therapeutic response measurement.

In at least some embodiments of the method, the automatically generating a next proposed set of stimulation parameter values determines the next proposed set by ranking possible sets of stimulation parameter values based upon one or more rules. In at least some of these embodiments, the rules rank remaining possible proposed sets of values. In at least some of these embodiments, the rules include at least one of: a rule based upon retrying locations within a number of iterations, rule based upon mathematical proximity of proposed sets of stimulation parameter values to sets of stimulation parameter values already tested, a rule based upon values of a stimulation parameter leading to adverse side effects, and/or a rule based upon size of step between values of a same stimulation parameter.

In at least some embodiments of the method, the next proposed set of stimulation parameter values is determined in each subsequent iteration in contact order, wherein contact order means testing along a first contact until side effects are prohibitive before testing a next proximal contact on a lead. In at least some embodiments of the method, the next proposed set of stimulation parameter values is determined in each subsequent iteration by selectively choosing contacts along the main access of a lead and varying other stimulation parameters for each selectively chosen contact. In at least some embodiments of the method, the next proposed set of stimulation parameter values is determined in each subsequent iteration randomly, based upon a model of the patient, or a spatial search algorithm. In at least some embodiments of the method, the next proposed set of stimulation parameter values is determined in each subsequent iteration by varying size of jump to a next proposed set of combined values of the plurality of stimulation parameters.

In at least some embodiments of the method, value limits are defined for at least some of the plurality of stimulation parameters.

In at least some embodiments of the method, the method is considered to have determined an optimal response based upon fastest time to determine: a therapeutic response value that is within the designated tolerance, a therapeutic response value that is closest to desired therapeutic response value, or least battery use for some therapeutic response value that is within the designated tolerance.

Yet another embodiment is a computer-readable medium having instructions stored thereon that includes any of the acts of the pulse generator feedback control logic of any of the system embodiments described or that includes any of the acts of any of the method embodiments described.

In at least one embodiment, the computer-readable medium includes instructions that control a computer processor to automatically determine programming settings of an implantable pulse generator (IPG) associated with a patient by performing a method including: automatically generating a proposed set of values of a plurality of stimulation parameters that each affect a stimulation aspect of the IPG; causing stimulation parameters of the IPG to be set to the automatically generated proposed set of stimulation parameter values; receiving one or more clinical response values as a result of the IPG being set to the proposed set of stimulation parameter values; automatically generating, by incorporating one or more machine learning engines, a revised proposed set of stimulation parameter values; causing stimulation parameters of the IPG to be set to the automatically generated revised proposed set of stimulation parameter values; and repeating the receiving the one or more clinical response values, automatically generating, by incorporating one or more machine learning engines, a revised proposed set of stimulation parameter values, and causing the stimulation parameters of the IPG to be set to the revised proposed set of stimulation parameter values, until or unless a stop condition has been reached or the received one or more clinical response values indicates a value that corresponds to a therapeutic response measurement within a designated tolerance.

In at least one embodiment, the medium is a memory in a computing system.

BRIEF DESCRIPTION OF THE DRAWINGS

Non-limiting and non-exhaustive embodiments of the present techniques are described with reference to the following drawings. In the drawings, like reference numerals refer to like parts throughout the various figures unless otherwise specified.

For a better understanding of the present techniques, reference will be made to the following Detailed Description, which is to be read in association with the accompanying drawings, wherein:

FIGS. 3A-3H are schematic perspective views of different embodiments of a distal end of a lead containing ring electrodes and segmented electrodes, according to described techniques;

FIGS. 6A-6K are example display screens for a user interface for visualizing stimulation parameter determinations using the feedback loop stimulation parameter control system according to described techniques.

FIG. 9 is an example schematic of tested location values in a clinical effects map.

DETAILED DESCRIPTION

The present invention is directed to the area of implantable electrical stimulation systems and methods of making and using the systems. The present invention is also directed to systems and methods for automatically determining advantageous stimulation parameter values using machine learning techniques to explore and/or set parameters of an electrical stimulation device.

Suitable implantable electrical stimulation systems include, but are not limited to, a least one lead with one or more electrodes disposed on a distal end of the lead and one or more terminals disposed on one or more proximal ends of the lead. Leads include, for example, percutaneous leads, paddle leads, cuff leads, or any other arrangement of electrodes on a lead. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; 8,391,985; and 8,688,235; and U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; and 2013/0197602, all of which are incorporated by reference. In the discussion below, a percutaneous lead will be exemplified, but it will be understood that the methods and systems described herein are also applicable to paddle leads and other leads.

A lead for electrical stimulation (for example, deep brain or spinal cord stimulation) includes stimulation electrodes that can be ring electrodes, segmented electrodes that extend only partially around the circumference of the lead, or any other type of electrode, or any combination thereof. The segmented electrodes can be provided in sets of electrodes, with each set having electrodes circumferentially distributed about the lead at a particular longitudinal position. For illustrative purposes, the leads, systems, and methods are described herein relative to use for deep brain stimulation, but it will be understood that any of the leads, systems, and methods can be used for applications other than deep brain stimulation, including spinal cord stimulation, peripheral nerve stimulation, dorsal root ganglion stimulation, or stimulation of other nerves, muscles, and tissues.

Figure 1:
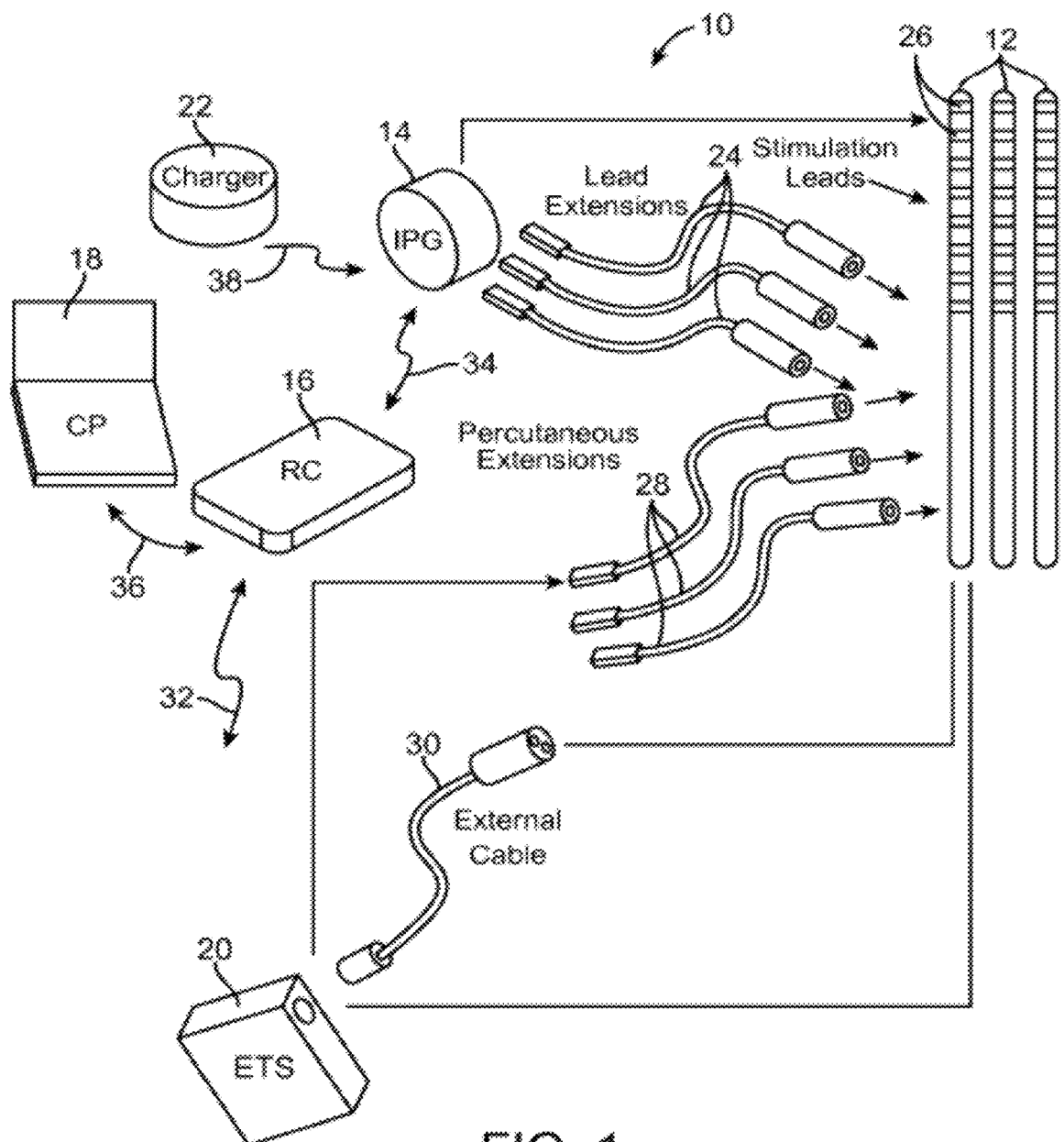
FIG. 1 is a schematic view of one embodiment of an electrical stimulation system, according to described techniques.

Turning to FIG. 1, one embodiment of an electrical stimulation system 10 includes one or more stimulation leads 12 and an implantable pulse generator (IPG) 14. The system 10 can also include one or more of an external remote control (RC) 16, a clinician's programmer (CP) 18, an external trial stimulator (ETS) 20, or an external charger 22.

The IPG 14 is physically connected, optionally via one or more lead extensions 24, to the stimulation lead(s) 12. Each lead carries multiple electrodes 26 arranged in an array. The IPG 14 includes pulse generation circuitry that delivers electrical stimulation energy in the form of, for example, a pulsed electrical waveform (i.e., a temporal series of electrical pulses) to the electrode array 26 in accordance with a set of stimulation parameters. The implantable pulse generator can be implanted into a patient's body, for example, below the patient's clavicle area or within the patient's buttocks or abdominal cavity. The implantable pulse generator can have eight or sixteen stimulation channels which may be independently programmable to control the magnitude of the current stimulus from each channel. In some embodiments, the implantable pulse generator can have more or fewer than eight or sixteen stimulation channels (e.g., 4-, 6-, 32-, or more stimulation channels). The implantable pulse generator can have one, two, three, four, or more connector ports, for receiving the terminals of the leads.

The ETS 20 may also be physically connected, optionally via the percutaneous lead extensions 28 and external cable 30, to the stimulation leads 12. The ETS 20, which may have similar pulse generation circuitry as the IPG 14, also delivers electrical stimulation energy in the form of, for example, a pulsed electrical waveform to the electrode array 26 in accordance with a set of stimulation parameters. One difference between the ETS 20 and the IPG 14 is that the ETS 20 is often a non-implantable device that is used on a trial basis after the neurostimulation leads 12 have been implanted and prior to implantation of the IPG 14, to test the responsiveness of the stimulation that is to be provided. Any functions described herein with respect to the IPG 14 can likewise be performed with respect to the ETS 20.

The RC 16 may be used to telemetrically communicate with or control the IPG 14 or ETS 20 via a uni- or bi-directional wireless communications link 32. Once the IPG 14 and neurostimulation leads 12 are implanted, the RC 16 may be used to telemetrically communicate with or control the IPG 14 via a uni- or bi-directional communications link 34. Such communication or control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. The CP 18 allows a user, such as a clinician, the ability to program stimulation parameters for the IPG 14 and ETS 20 in the operating room and in follow-up sessions.

The CP 18 may perform this function by indirectly communicating with the IPG 14 or ETS 20, through the RC 16, via a wireless communications link 36. Alternatively, the CP 18 may directly communicate with the IPG 14 or ETS 20 via a wireless communications link (not shown). The stimulation parameters provided by the CP 18 are also used to program the RC 16, so that the stimulation parameters can be subsequently modified by operation of the RC 16 in a stand-alone mode (i.e., without the assistance of the CP 18).

For purposes of brevity, the details of the RC 16, CP 18, ETS 20, and external charger 22 will not be further described herein. Details of exemplary embodiments of these devices are disclosed in U.S. Pat. No. 6,895,280, which is expressly incorporated herein by reference. Other examples of electrical stimulation systems can be found at U.S. Pat. Nos. 6,181,969; 6,516,227; 6,609,029; 6,609,032; 6,741,892; 7,949,395; 7,244,150; 7,672,734; and 7,761,165; 7,974,706; 8,175,710; 8,224,450; and 8,364,278; and U.S. Patent Application Publication No. 2007/0150036, as well as the other references cited above, all of which are incorporated by reference.

Figure 2:
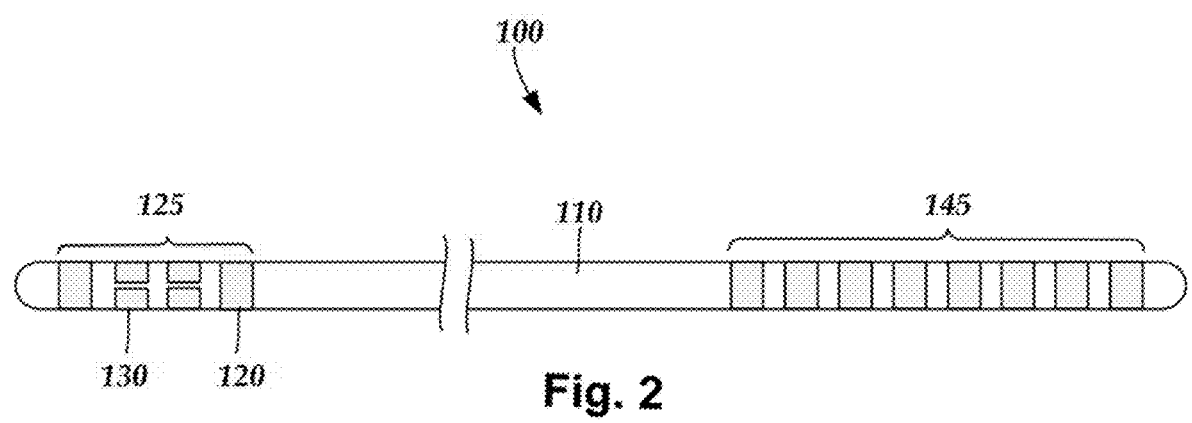
FIG. 2 is a schematic side view of one embodiment of an electrical stimulation lead, according to described techniques.

FIG. 2 is an example schematic side view of one embodiment of an electrical stimulation lead. FIG. 2 illustrates a lead 110 with electrodes 125 disposed at least partially about a circumference of the lead 110 along a distal end portion of the lead and terminals 145 disposed along a proximal end portion of the lead. The lead 110 can be implanted near or within the desired portion of the body to be stimulated such as, for example, the brain, spinal cord, or other body organs or tissues. In one example of operation for deep brain stimulation, access to the desired position in the brain can be accomplished by drilling a hole in the patient's skull or cranium with a cranial drill (commonly referred to as a burr), and coagulating and incising the dura mater, or brain covering. The lead 110 can be inserted into the cranium and brain tissue with the assistance of a stylet (not shown). The lead 110 can be guided to the target location within the brain using, for example, a stereotactic frame and a microdrive motor system. In some embodiments, the microdrive motor system can be fully or partially automatic. The microdrive motor system may be configured to perform one or more the following actions (alone or in combination): insert the lead 110, advance the lead 110, retract the lead 110, or rotate the lead 110.

In some embodiments, measurement devices coupled to the muscles or other tissues stimulated by the target neurons, or a unit responsive to the patient or clinician, can be coupled to the implantable pulse generator or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in, for example, tremor frequency or amplitude in response to stimulation of neurons. Alternatively, the patient or clinician can observe the muscle and provide feedback.

The lead 110 for deep brain stimulation can include stimulation electrodes, recording electrodes, or both. In at least some embodiments, the lead 110 is rotatable so that the stimulation electrodes can be aligned with the target neurons after the neurons have been located using the recording electrodes.

Stimulation electrodes may be disposed on the circumference of the lead 110 to stimulate the target neurons. Stimulation electrodes may be ring-shaped so that current projects from each electrode equally in every direction from the position of the electrode along a length of the lead 110. In the embodiment of FIG. 2, two of the electrodes 120 are ring electrodes 120. Ring electrodes typically do not enable stimulus current to be directed from only a limited angular range around of the lead. Segmented electrodes 130, however, can be used to direct stimulus current to a selected angular range around the lead. When segmented electrodes are used in conjunction with an implantable pulse generator that delivers constant current stimulus, current steering can be achieved to more precisely deliver the stimulus to a position around an axis of the lead (i.e., radial positioning around the axis of the lead). To achieve current steering, segmented electrodes can be utilized in addition to, or as an alternative to, ring electrodes.

The lead 100 includes a lead body 110, terminals 145, and one or more ring electrodes 120 and one or more sets of segmented electrodes 130 (or any other combination of electrodes). The lead body 110 can be formed of a biocompatible, non-conducting material such as, for example, a polymeric material. Suitable polymeric materials include, but are not limited to, silicone, polyurethane, polyurea, polyurethane-urea, polyethylene, or the like. Once implanted in the body, the lead 100 may be in contact with body tissue for extended periods of time. In at least some embodiments, the lead 100 has a cross-sectional diameter of no more than 1.5 mm and may be in the range of 0.5 to 1.5 mm. In at least some embodiments, the lead 100 has a length of at least 10 cm and the length of the lead 100 may be in the range of 10 to 70 cm.

The electrodes 125 can be made using a metal, alloy, conductive oxide, or any other suitable conductive biocompatible material. Examples of suitable materials include, but are not limited to, platinum, platinum iridium alloy, iridium, titanium, tungsten, palladium, palladium rhodium, or the like. Preferably, the electrodes are made of a material that is biocompatible and does not substantially corrode under expected operating conditions in the operating environment for the expected duration of use.

Each of the electrodes can either be used or unused (OFF). When the electrode is used, the electrode can be used as an anode or cathode and carry anodic or cathodic current. In some instances, an electrode might be an anode for a period of time and a cathode for a period of time.

Deep brain stimulation leads and other leads may include one or more sets of segmented electrodes. Segmented electrodes may provide for superior current steering than ring electrodes because target structures in deep brain stimulation or other stimulation are not typically symmetric about the axis of the distal electrode array. Instead, a target may be located on one side of a plane running through the axis of the lead. Through the use of a radially segmented electrode array ("RSEA"), current steering can be performed not only along a length of the lead but also around a circumference of the lead. This provides precise three-dimensional targeting and delivery of the current stimulus to neural target tissue, while potentially avoiding stimulation of other tissue. Examples of leads with segmented electrodes include U.S. Pat. Nos. 8,473,061; 8,571,665; and 8,792,993; U.S. Patent Application Publications Nos. 2010/0268298; 2011/0005069; 2011/0130803; 2011/0130816; 2011/0130817; 2011/0130818; 2011/0078900; 2011/0238129; 2012/0016378; 2012/0046710; 2012/0071949; 2012/0165911; 2012/197375; 2012/0203316; 2012/0203320; 2012/0203321; 2013/0197424; 2013/0197602; 2014/0039587; 2014/0353001; 2014/0358208; 2014/0358209; 2014/0358210; 2015/0045864; 2015/0066120; 2015/0018915; 2015/0051681; U.S. patent application Ser. Nos. 14/557,211 and 14/286,797; and U.S. Provisional Patent Application Ser. No. 62/113,291, all of which are incorporated herein by reference.

Any number of segmented electrodes 130 may be disposed on the lead body 110 including, for example, one, two three, four, five, six, seven, eight, nine, ten, eleven, twelve, thirteen, fourteen, fifteen, sixteen or more segmented electrodes 130. It will be understood that any number of segmented electrodes 130 may be disposed along the length of the lead body 110. A segmented electrode 130 typically extends only 75%, 67%, 60%, 50%, 40%, 33%, 25%, 20%, 17%, 15%, or less around the circumference of the lead.

The segmented electrodes 130 may be grouped into sets of segmented electrodes, where each set is disposed around a circumference of the lead 100 at a particular longitudinal portion of the lead 100. The lead 100 may have any number segmented electrodes 130 in a given set of segmented electrodes. The lead 100 may have one, two, three, four, five, six, seven, eight, or more segmented electrodes 130 in a given set. In at least some embodiments, each set of segmented electrodes 130 of the lead 100 contains the same number of segmented electrodes 130. The segmented electrodes 130 disposed on the lead 100 may include a different number of electrodes than at least one other set of segmented electrodes 130 disposed on the lead 100.

The segmented electrodes 130 may vary in size and shape. In some embodiments, the segmented electrodes 130 are all of the same size, shape, diameter, width or area or any combination thereof. In some embodiments, the segmented electrodes 130 of each circumferential set (or even all segmented electrodes disposed on the lead 100) may be identical in size and shape.

Each set of segmented electrodes 130 may be disposed around the circumference of the lead body 110 to form a substantially cylindrical shape around the lead body 110. The spacing between individual electrodes of a given set of the segmented electrodes may be the same, or different from, the spacing between individual electrodes of another set of segmented electrodes on the lead 100. In at least some embodiments, equal spaces, gaps or cutouts are disposed between each segmented electrode 130 around the circumference of the lead body 110. In other embodiments, the spaces, gaps or cutouts between the segmented electrodes 130 may differ in size or shape. In other embodiments, the spaces, gaps, or cutouts between segmented electrodes 130 may be uniform for a particular set of the segmented electrodes 130, or for all sets of the segmented electrodes 130. The sets of segmented electrodes 130 may be positioned in irregular or regular intervals along a length the lead body 110.

Conductor wires (not shown) that attach to the ring electrodes 120 or segmented electrodes 130 extend along the lead body 110. These conductor wires may extend through the material of the lead 100 or along one or more lumens defined by the lead 100, or both. The conductor wires couple the electrodes 120, 130 to the terminals 145.

Figure 3E:
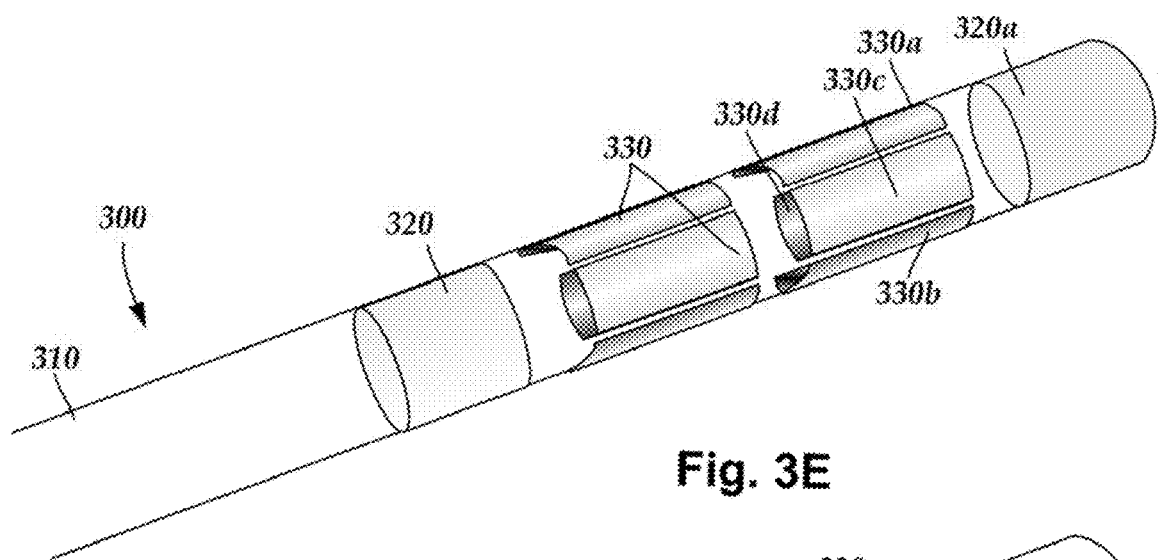
Figure 3F:
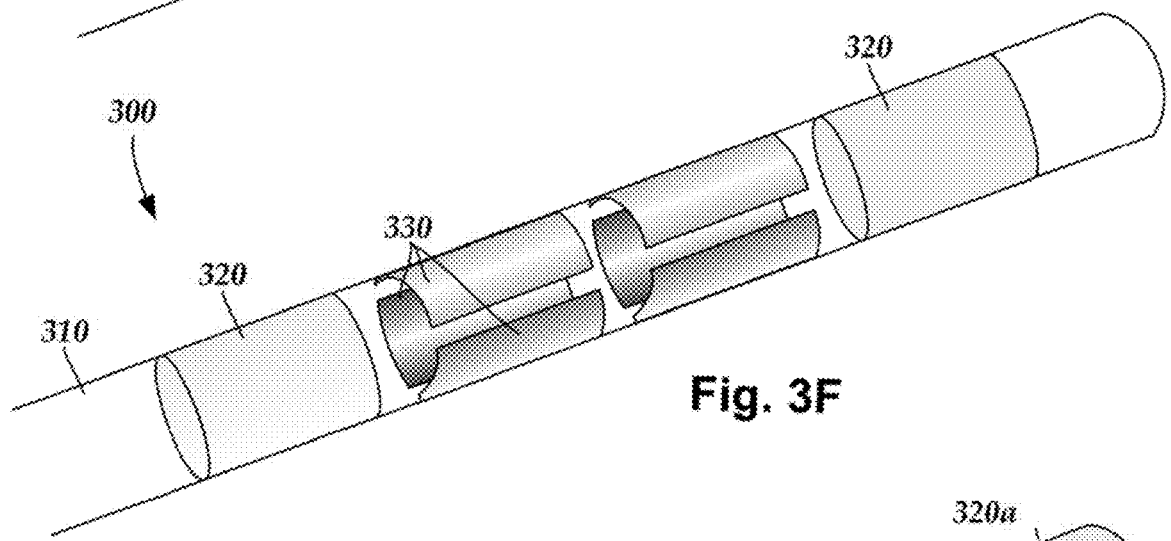
Figure 3G:
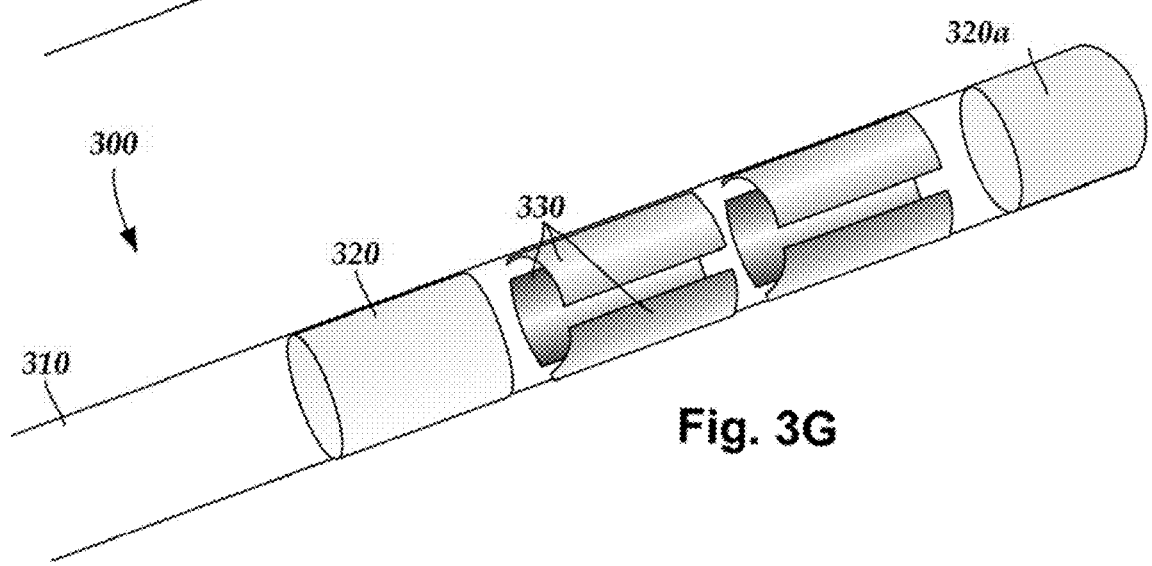
Figure 3H:
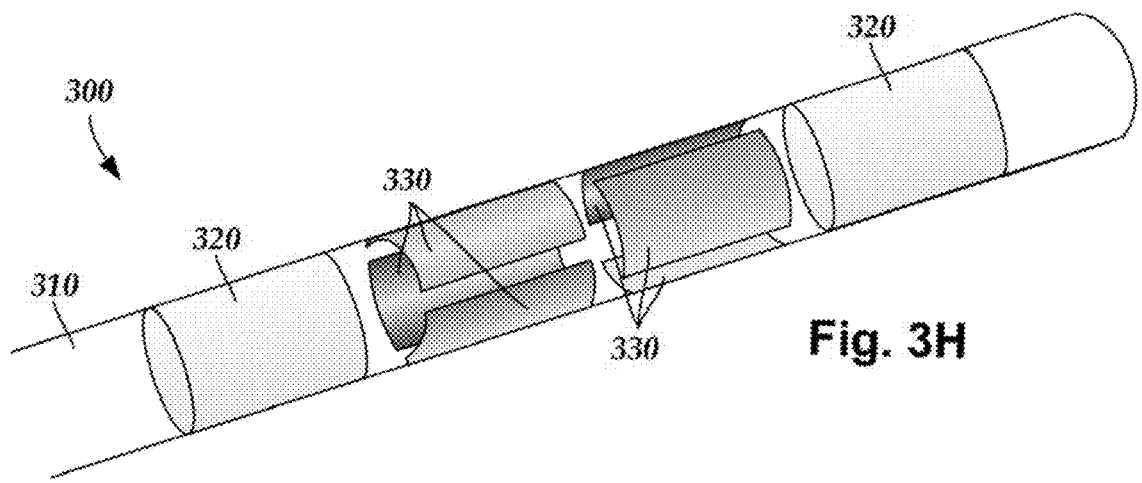

FIGS. 3A-3H illustrate different embodiments of leads 300 with segmented electrodes 330, optional ring electrodes 320 or tip electrodes 320a, and a lead body 310. The sets of segmented electrodes 330 each include either two (FIG. 3B), three (FIGS. 3E-3H), or four (FIGS. 3A, 3C, and 3D) or any other number of segmented electrodes including, for example, three, five, six, or more. The sets of segmented electrodes 330 can be aligned with each other (FIGS. 3A-3G) or staggered (FIG. 3H).

When the lead 100 includes both ring electrodes 120 and segmented electrodes 130, the ring electrodes 120 and the segmented electrodes 130 may be arranged in any suitable configuration. For example, when the lead 100 includes two ring electrodes 120 and two sets of segmented electrodes 130, the ring electrodes 120 can flank the two sets of segmented electrodes 130 (see e.g., FIGS. 2, 3A, and 3E-3H—ring electrodes 320 and segmented electrode 330). Alternately, the two sets of ring electrodes 120 can be disposed proximal to the two sets of segmented electrodes 130 (see e.g., FIG. 3C—ring electrodes 320 and segmented electrode 330), or the two sets of ring electrodes 120 can be disposed distal to the two sets of segmented electrodes 130 (see e.g., FIG. 3D—ring electrodes 320 and segmented electrode 330). One of the ring electrodes can be a tip electrode (see, tip electrode 320*a* of FIGS. 3E and 3G). It will be understood that other configurations are possible as well (e.g., alternating ring and segmented electrodes, or the like).

By varying the location of the segmented electrodes 130, different coverage of the target neurons may be selected. For example, the electrode arrangement of FIG. 3C may be useful if the physician anticipates that the neural target will be closer to a distal tip of the lead body 110, while the electrode arrangement of FIG. 3D may be useful if the physician anticipates that the neural target will be closer to a proximal end of the lead body 110.

Any combination of ring electrodes 120 and segmented electrodes 130 may be disposed on the lead 100. For example, the lead may include a first ring electrode 120, two sets of segmented electrodes; each set formed of four segmented electrodes 130, and a final ring electrode 120 at the end of the lead. This configuration may simply be referred to as a 1-4-4-1 configuration (FIGS. 3A and 3E—ring electrodes 320 and segmented electrode 330). It may be useful to refer to the electrodes with this shorthand notation. Thus, the embodiment of FIG. 3C may be referred to as a 1-1-4-4 configuration, while the embodiment of FIG. 3D may be referred to as a 4-4-1-1 configuration. The embodiments of FIGS. 3F, 3G, and 3H can be referred to as a 1-3-3-1 configuration. Other electrode configurations include, for example, a 2-2-2-2 configuration, where four sets of segmented electrodes are disposed on the lead, and a 4-4 configuration, where two sets of segmented electrodes, each having four segmented electrodes 130 are disposed on the lead. The 1-3-3-1 electrode configuration of FIGS. 3F, 3G, and 3H has two sets of segmented electrodes, each set containing three electrodes disposed around the circumference of the lead, flanked by two ring electrodes (FIGS. 3F and 3H) or a ring electrode and a tip electrode (FIG. 3G). In some embodiments, the lead includes 16 electrodes. Possible configurations for a 16-electrode lead include, but are not limited to 4-4-4-4; 8-8; 3-3-3-3-3-1 (and all rearrangements of this configuration); and 2-2-2-2-2-2-2-2.

Any other suitable arrangements of segmented and/or ring electrodes can be used including, but not limited to, those disclosed in U.S. Provisional Patent Application Ser. No. 62/113,291 and U.S. Patent Applications Publication Nos. 2012/0197375 and 2015/0045864, all of which are incorporated herein by reference. As an example, arrangements in which segmented electrodes are arranged helically with respect to each other. One embodiment includes a double helix.

One or more electrical stimulation leads can be implanted in the body of a patient (for example, in the brain or spinal cord of the patient) and used to stimulate surrounding tissue. The lead(s) are coupled to the implantable pulse generator (such as IPG 14 in FIG. 1). After implantation, a clinician will program the implantable pulse generator using the clinician programmer, remote control, or other programming device. According to at least some programming techniques, the clinician enters stimulator parameters for a stimulation program and the stimulation program is used to stimulate the patient. The clinician observes the patient response. In at least some instances, the clinician asks the patient to describe, rate, or otherwise provide information about the effects of the stimulation such as what portion of the body is affected, how strong is the stimulation effect, whether there are side effects or negative effects, and the like.

In at least some instances, the clinician may be remote from the patient. For example, the clinician may be in another room, treatment or care facility, city, state, or even country. This may be advantageous as it can allow skilled clinicians to interact with patients that are remote from the clinician without requiring travel or loss of time by the clinician. As another example, the patient may be sent home after surgery and the clinician can program the device remotely while the patient is at home.

Such remote programming, however, may encounter difficulties such as, for example, limited bandwidth, speech impaired patients, deaf patients, patients who speak a different language from the clinician, noise over the phone or video connection between patient and clinician, patient difficulty hearing due to hearing aid devices, and the like.

In addition, current techniques for programming an electrical stimulation system (such as by programming IPG 14 in FIG. 1) are a tedious trial-and-error process which only explores certain possible programming parameters. With the introduction of multiple independent sources of current and complex lead geometries, the exploration of which parameters to manipulate and how to program them becomes more difficult to express and visualize as well as to set and track.

Accordingly, in at least some instances, it may be desirable to program the implantable pulse generator (or other deep brain stimulation device) using a semi- or wholly automated system such as that described herein that obtains feedback from the patient, generates new stimulator parameter values using machine learning techniques, and tests them to determine whether the parameter values have caused a therapeutic response that is more desirable. This process iterates until stimulation parameter values are determined that cause therapeutic responses within a designated tolerance or until a stop condition is reached. The feedback that is obtained is used in conjunction with the machine learning techniques to explore the stimulation parameter space for parameter values that potentially provide better outcomes for the patient, faster programming of the device, increased battery life, and/or control multiple independent current sources and directional leads. Determining which parameter values cause therapeutic responses within the designated tolerance or within other potentially specifiable parameters (such as with least battery usage and the soonest) is also referred to as finding "optimal" stimulation parameter values.

In some instances, the feedback loop stimulation parameter control system is completely automatic and responses to changes in the stimulation parameter values are obtained from one or more sensors associated with the patient. Having a sensor allows the response to be directly monitored by the feedback loop stimulation parameter control system instead of depending upon potentially subjective entry of patient feedback. This automated system provides a feedback loop to a machine learning based control system that tries to intelligently choose new parameter values based upon the observables from the patient (or other patient data) and a set of rules. Feedback loop programming of a deep brain stimulator using machine learning techniques is discussed in further detail with respect to FIGS. 5-8. Deep brain stimulation is used herein as an example of the systems and methods, but it will be understood that the systems and methods can be used in other stimulation techniques including, but not limited to, spinal cord stimulation, peripheral nerve stimulation, organ stimulation, and the like.

In at least one embodiment, a feedback loop stimulation parameter control system such as that described in FIGS. 5-8 may take into account the type of electrode (e.g., ring or segmented) as well as the location of the electrode on the lead. These different types of electrodes cause complexities in the exploration of the stimulation parameter space in determining optimal parameter values. As the control system determines how to move within the stimulation parameter space to explore the next set of parameter values to test, the system may move differently between segmented electrodes than from a ring electrode to a segmented electrode, from a ring electrode to a ring electrode, etc. Thus different types of electrodes that may be present on a lead may result in different calculations and determinations by an example stimulation parameter feedback loop control system.

In at least some instances, a treating physician may wish to tailor the stimulation parameters (such as which one or more of the stimulating electrode contacts to use, the stimulation pulse amplitude (such as current or voltage amplitude depending on the stimulator being used) the stimulation pulse width, the stimulation frequency, or the like, (or any combination thereof) for a particular patient to improve the effectiveness of the therapy.

The programming procedure performed in conventional electrical stimulation (such as deep brain or spinal cord stimulation) is often performed in an initial session and, in at least some instances, at later sessions. The procedure can involve, for example, testing different sets of stimulation parameters (which can include variations in the electrodes that are selected as well as different electrical parameters such as amplitude, duration, pulse frequency, and the like) and annotating when there is a beneficial therapeutic effect or an unwanted side effect. In at least some embodiments, the clinician performs a monopolar review testing each electrode individually and recording therapeutic/beneficial effects and side effects for each electrode on the lead corresponding to different values of the stimulation amplitude or other stimulation parameters. The clinician may also perform bipolar or multipolar reviews using two or more electrodes.

In contrast to these conventional methods, the feedback loop stimulation parameter control system described here can be used to provide information (e.g., which stimulation parameters to set and to what values) or can be integrated into other components of a stimulation system to set stimulation parameters while programming the device. For example, the feedback loop stimulation parameter control system can be integrated with programming software (such as the IPG software). In addition, the feedback loop stimulation parameter control system can be integrated into clinical response software to provide recommendations or new settings based upon observed (or detected) clinical responses. In at least some embodiments, the stimulation parameter feedback loop control system, programming software, and clinical response software are all integrated.

In at least some of these scenarios, the clinician may use the feedback loop stimulation parameter control system to monitor a patient during programming, to transfer data (such as stimulation parameter values) to another device, or may not be involved—the feedback loop stimulation parameter control system may be used to determine stimulation parameters and set the patient's device without the presence of the clinician.

All such permutations of location of the feedback loop stimulation parameter control system into the general environment of a stimulation system and the extent of involvement of the clinician are contemplated.

Figure 4:
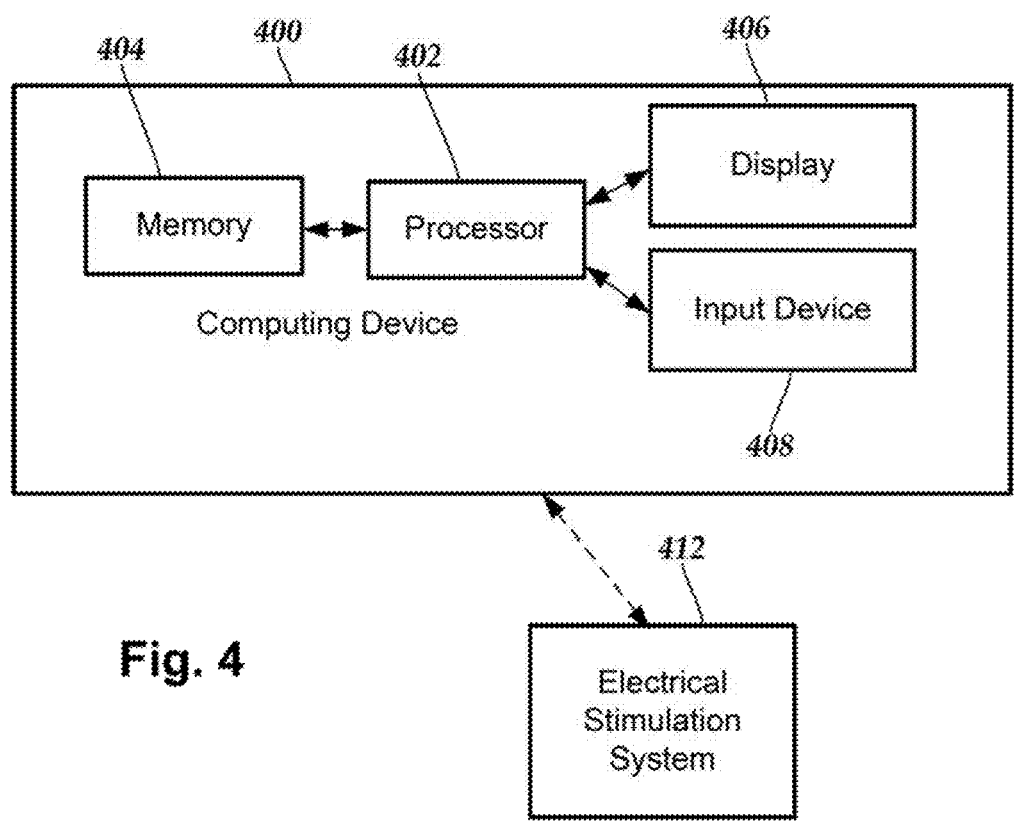
FIG. 4 is a schematic block diagram of one embodiment of a computing system, for programming an electrical stimulation system according to described techniques.

FIG. 4 illustrates one embodiment of a computing device 400 for running the software, hardware, or firmware embodiments of a stimulation parameter feedback loop control system. The computing device 400 includes a processor 402 and a memory 404, a display 406, and an input device 408. Optionally, the computing device 400 may be connected to or otherwise integrated with the electrical stimulation system 412 (such as the system 10 in FIG. 1). For example, in some embodiments, the computing device 400 is part of the electrical stimulation system 412, such as part of the clinician programmer 18 (FIG. 1), remote control 16 (FIG. 1), or external trial stimulator 20 (FIG. 1). In other embodiments, the computing device 400 is separate from the electrical stimulation system 412.

The computing device 400 can be a computer, tablet, mobile device, or any other suitable device for processing information. The computing device 400 can be local to the user or can include components that are non-local to the computer including one or both of the processor 402 or memory 404 (or portions thereof). For example, in some embodiments, the user may operate a terminal that is connected to a non-local processor or memory.

Other examples of computing devices can include a watch, wristband, smart phone, or the like. Such computing devices can wirelessly communicate with the other components of the electrical stimulation system, such as the clinician programmer 18 (FIG. 1), remote control 16 (FIG. 1), external trial stimulator 20 (FIG. 1), or IPG 14 (FIG. 1). Such devices may also be useful for gathering patient information, such as general activity level or present queries or tests to the patient to identify or score pain, depression, stimulation effects or side effects, cognitive ability, or the like. For example, the device may ask the patient to take a periodic test (for example, every day) for cognitive ability to monitor, for example, Alzheimer's disease. Such devices may also be used to sense patient responses to therapy such as, for example, tremor, heart rate, or the like. The device may communicate with the clinician programmer 18 (FIG. 1), remote control 16 (FIG. 1), external trial stimulator 20 (FIG. 1), or IPG 14 (FIG. 1) to direct changes to the stimulation parameters using a closed loop algorithm, as described below, which may be on the device or the IPG. This device could be given to the patient to wear only during programming sessions; or, it could be worn all of the time and continually make adjustments to the stimulation parameters. The algorithm could be on the patient's phone, which is connected to the IPG and possibly an evaluating device (e.g. a wristband or watch), to make changes to the stimulation parameters. These devices may also be used to record and send information to the clinician.

The computing device 400 can utilize any suitable processor 402 including one or more hardware processors that may be local to the user or non-local to the user or other components of the computing device. The processor 402 is configured to execute instructions provided to the processor.

Any suitable memory 404 can be used for the computing device 402. The memory 404 illustrates a type of computer-readable media, namely computer-readable storage media. Computer-readable storage media may include, but are not limited to, nonvolatile, non-transitory, removable, and nonremovable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, Bluetooth™, near field communication, and other wireless media.

The display 406 can be any suitable display or presentation device, such as a monitor, screen, display, or the like, and can include a printer. The input device 408 can be, for example, a keyboard, mouse, touch screen, track ball, joystick, voice recognition system, or any combination thereof, or the like. Another input device 408 can be a camera from which the clinician can observe the patient. Yet another input device 408 is a microphone where the patient or clinician can provide responses or queries.

The electrical stimulation system 412 can include, for example, any of the components illustrated in FIG. 1. The electrical stimulation system 412 may communicate with the computing device 400 through a wired or wireless connection or, alternatively or additionally, a user can provide information between the electrical stimulation system 412 and the computing device 400 using a computer-readable medium or by some other mechanism. As mentioned, in some embodiments, the computing device 400 may include part of the electrical stimulation system, such as, for example, the IPG, CP, RC, ETS, or any combination thereof.

Figure 5:
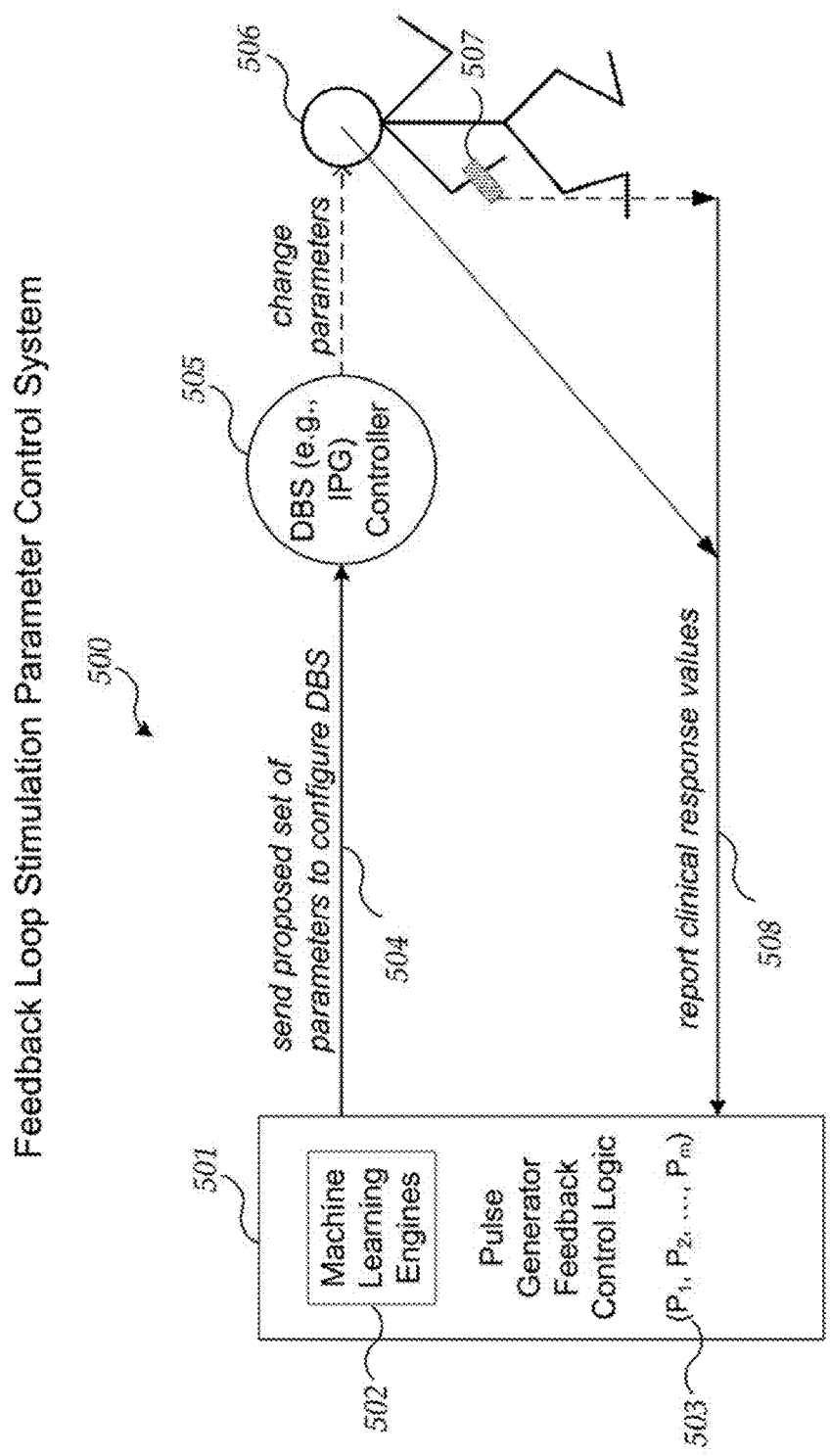
FIG. 5 is a schematic block diagram for a feedback loop stimulation parameter control system for determining electrical stimulator programming settings according to described techniques.

FIG. 5 is an example block diagram of an example feedback loop stimulation parameter control system. In at least some embodiments, the feedback loop stimulation parameter control system (FLSPCS) 500 includes pulse generator feedback control logic 501 which determines and sends parameters (504) to configure a deep brain stimulator controller 505 (such as IPG 14 or ETS 20 in FIG. 1). The deep brain stimulator controller 505 then modifies the stimulation parameters of the various leads (such as lead 100 in FIG. 2 or leads 300 in FIGS. 3A-3H) potentially causing different effects upon the patient 506 in which the IPG is implanted. The patient 506 provides feedback which is reported as clinical response values 508 to the pulse generator feedback control logic 501. In some embodiments, the patient 506 provides feedback automatically or semi-automatically via a sensor 507 which are sent to the pulse generator feedback control logic 501 as clinical response values 508. The control logic 501 then adjusts the values of stimulation parameters 503 based upon the received feedback 508 and based upon models implemented by one or more machine learning engines 502. The control logic 501 then sends these adjusted (new or revised) stimulation parameter values (504) to further configure the controller 505 to change the stimulation parameters of the leads implanted in patient 506 to the adjusted values. The feedback-control loop then continues until an outcome is reached that is considered optimal, desired, or acceptable, or until some other stop condition is reached such as number of iterations, time spent in programming session, or the like. An outcome may be considered optimal, desired, or acceptable if it meets certain threshold values or tests (e.g., better outcomes for the patient, faster programming of the device, increased battery life, and/or control multiple independent current sources and directional lead).

In some embodiments, the clinical response values 508 may be weighted according to the time at which the test took place. It has been found that, for at least some patients or at least some testing procedures, patient fatigue occurs over time which may degrade or otherwise change the clinical response values (whether obtained from the patient, clinician, or a sensor). For example, more recent clinical response values 508 may be weighted higher than earlier clinical response values as the more recent clinical response values are more predictive of the clinical response to the adjusted stimulation parameters because these later tests have a similar amount of patient fatigue. Examples of weights can be, but are not limited to, values in a range from 1.05 to 1.5.

Note that in at least some embodiments, the FLSPCS 500 may be executed on its own and is not connected to a controller. In such instances it may be used to merely determine and suggest programming parameters, visualize a parameter space, test potential parameters, etc.

In at least some embodiments, the machine learning engines 502 facilitate the feedback loop stimulation parameter control system (or a user of the system) to explore the possible stimulation parameter space in order to choose values for programming the deep brain simulator controller 505. Any type of machine learning engine, supervised or unsupervised, can be incorporated into the feedback loop stimulation parameter control system 500, including for example, Naïve Bayes classifiers, support vector machines (SVMs), ensemble classifiers, neural networks, Kalman filters, regression analyzers, etc. The role of the machine learning engines 502 in the FLSPCS 500 is to predict the outcomes for various stimulation parameter values to aid (e.g., a clinician) in exploring the stimulation parameter space more effectively and more efficiently to produce results that are optimal, desired, or acceptable. That is, a machine learning engine 502 generally trains itself on data to generate a model of the data. (In supervised machine learning the data is known a priori; in unsupervised machine learning, the model is derived from the data without a known initial structure.) Using the derived data model, the engines 502 can predict information about or classify a new piece of unknown data based upon what it already "knows."

In this instance, the machine learning engines 502 build models which are used to predict outcomes of sets of stimulation parameter values. A set of stimulation parameter values defines a value for each stimulation parameter being determined. For example, if current amplitude and contact location are the stimulation parameters being explored or adjusted, then a set of stimulation parameter values is a group of values—one for amplitude and one or more that describe the contact location (segmented contacts may have x, y, z directional components as well as a position on the axis of the lead). Outcomes of each set of stimulation parameter values may be further described as "optimal" if it meets certain criteria. Optimal outcome metrics may be predesignated or settable (variable) and refer to attributes such as: 1) time to outcome—fastest optimal outcome (assuming multiple outcomes with same clinical response); 2) best outcome—best possible clinical outcome within the parameter set chosen (global versus local optimal setting); and/or 3) battery savings—optimal outcome with least battery usage (assuming multiple outcomes with same clinical response).

In some embodiments, the machine learning engines 502 can utilize imaging data to inform the choice of the next set of values. This will be particularly useful, when the algorithm finds itself in a region of parameter space that is fairly flat and the choice of next step is not apparent from the patient response alone. Imaging data that provides information about the location of the lead in the patient's brain along with priors informing the algorithm of which directions may be better choices for the next step could lead to faster convergence.

In some embodiments, the machine learning engines 502 determine expected outcomes for parameter values that have not yet been tested based upon what the engines have "learned" thus far and provide a recommendation for a next set of values to test. Here, testing refers to the iterative testing required to find optimal parameters for configuring the deep brain stimulation controller 505. The recommendation for a next set of values to test is based upon which of the determined expected outcomes meet a set of designated (determined, selected, preselected, etc.) criteria (e.g., rules, heuristics, factors, and the like). For example, rules considered may include such factors as: the next set of values cannot be one of the last 10 settings tested or cannot be too close to previously tested setting. Examples of additional such rules are described with reference to FIGS. 7 and 8. Accordingly, the pulse generator feedback control logic 501 with its machine learning engines 502 is used to systematically explore the stimulation parameter space based upon what it has learned thus far and (optionally) different rules and/or heuristics that contribute to achieving optimal outcomes more efficiently.

The process for determining expected outcomes for (sets of) parameter values that have not yet been tested may involve use of other data for machine learning. For example, data from other programming sessions for the same patient as well as from other patients may be used to train the machine learning engines 502. In some embodiments, no prior data may be used. In this case, the machine learning engines 502 will use data learned from this patient only in one particular setting. In other embodiments, data from the same patient but from previous sessions may be used. In some embodiments all patient data from all sessions may be used. In some embodiments all patient data utilizing lead location information (knowledge of lead location in space relative to anatomy) may be used. Different other combinations are also possible.

In order to use this data for machine learning purposes, the data is first cleansed, optionally transformed, and then modeled. In some embodiments, new variables are derived, such as for use with directional leads, including central point of stimulation, maximum radius, spread of stimulation field, or the like Data cleansing and transformation techniques such as missing data imputation and dimension reduction may be employed to ready the data for modeling. When there is no prior data used, this step may not be necessary. (The model is built up as more data is observed by the system 500.)

In some embodiments, different types of models may be used to fit stimulation parameter data such as (including but not limited to):
1. Function-based models (splines, wavelets, kernel regression, additive models, generalized additive models, etc.);
2. Spatial or spatial-temporal models (variogram, dynamic or static models, random fields, copulas, etc.);
3. Time series models (autoregressive, moving average, autoregressive conditional heteroscedasticity models along with their variants—ARMA, VARMA, VARMAX, ARIMA, GARCH, etc.);
4. Latent variable models (factor analysis, structural equation modeling, hidden Markov models, etc.);
5. Graph models (Directed Acyclic Graphs, Bayesian networks, undirected graphs, etc.);
6. Other models (linear or non-linear regression, mixture models, hierarchical models, etc.)

In addition, each machine learning engine 502, when more than one is used, may derive its own model using types that are distinct from each other (although not necessary). When this occurs, the logic 501 may let each machine learning engine 502 come to its own conclusion for recommending the next set of stimulation parameter values to test. In some instances, the machine learning engines 502 may "vote" on the recommendation with recommendations by engines that have historically provided optimal answers potentially weighted higher than those determined by engines that have not. Other variations and other voting schemes are possible.

The machine learning engines 502 also may desire to determine how best a predicted outcome meets the optimal outcome metrics. To do this, in some embodiments a variety of different optimization techniques may be used, including:
1. All of the optimization algorithms and estimation procedures that were used to fit the model to the data (e.g., gradient descent, Kalman filter, Markov chain, Monte Carlo, and the like);
2. Optimization algorithms reformulated for search (e.g., simulated annealing);
3. Spatial interpolation (e.g., kriging, inverse distance weighting, natural neighbor, etc.);
4. Supplementary methods that aid the optimization process (e.g., variable selections, regularization, cross validation, etc.); and
5. Search algorithms (e.g., "golden section" search, binary search, etc.).

Using these techniques, the machine learning engines 502 can decide whether a particular predicted outcome for a set of stimulation parameter values is the fastest optimal outcome, the best possible clinical outcome, or the optimal outcome with least battery usage, for example.

As mentioned, in some embodiments, a golden section search may be used as an optimization algorithm to determine whether a predicted outcome meets the optimal outcome metrics. The golden section search is performed as follows:
First search in one dimension, then in a subsequent dimension;
Search dimension is broken into parts, relative clinical score determines an excluded portion of space, and search continues iteratively;
Search range and/or epsilon value can be adaptive as nearing ideal location;
For cylindrical lead, dimensions are typically amplitude and contact location; for directional lead, rotation angle may be added.

Other embodiments may support other types of search and/or optimization algorithms. In some embodiments, optimization of results may be performed at the same time as initial search for acceptable outcomes, or may be performed at a different time.

As mentioned, the pulse generator feedback control logic 501 may be used to search and configure (and/or visualize and/or test) different types of stimulation parameters of the various leads potentially causing different effects upon the patient 506 in which the IPG is implanted. Embodiments of a feedback loop stimulation parameter control system 500 may support a variety of different stimulation parameters to be configured, including one or more of the following:

1. Contact Configurations/Polarities
    a. Monopoles only—only use single contact cathodes
    b. Monopoles and fractionalization—use single contact cathodes or two adjacent contact cathodes (e.g., which electrodes are on/off to steer current)
    c. Bipoles only—use adjacent contacts as anode-cathode, search all possible pairings
    d. Any possible settings—all configurations possible with given system including anodes
2. Pulse Widths
    a. Single pulse width—only use a single pulse width for entire search (e.g., 60 us, 30 us)
    b. Multiple pulse widths—allow search to take place between varying pulse widths
3. Frequencies
    a. Single frequency—only use a single frequency for entire search (e.g, 130 Hz)
    b. Multiple frequencies—allow search to take place between varying frequencies
4. Amplitude
    a. Single amplitude—only use a single amplitude for entire search
    b. Multiple amplitudes—allow search to take place at varying amplitudes Given these possible stimulation parameters, the FLSPCS 500 can move about the parameter space in different orders, by different increments, and limited to specific ranges. Namely, in some embodiments of the FLSPCS 500, techniques for determining incremental steps to test may include one or more of (including in combination where the combination makes sense):

1. Basic monopolar review—progress along a single contact until side effects are prohibitive, then proceed to adjacent control
2. Steering—select contact, increase amplitude until therapeutic effect is seen, steer along main axis of the lead (move up and down and around—circumnavigate—the lead)
3. Model based—select next step according to parameters selected by the model, based on previous parameters or previous patients' experience
4. Random—select next step at random; may be among entire space or among a subset of candidates (may be used at beginning of session to explore the space, then move to one of the other techniques)
5. Spatial search algorithm—use optimized search algorithm to traverse stimulation parameter space and find optimal settings.

In some embodiments, step size limitations may include:
1. No limit—can test any parameter combination
2. Step size limit based off of previous step
3. Step size limit based off of all previous search points
4. Step size limit based off of the number of steps already taken.

In some embodiments, search range limitations may include one or more of (including in combination where makes sense):
1. No limits—can test any parameter combination
2. Amplitude limit—can only test to a certain amplitude
3. Charge limit—can only test to certain amplitude*pulse width limit
4. Defined limit—physician/clinician does a monopolar review-like search to identify side effect boundaries at each contact; these are then used as inputs for search bounds.

Different combinations of increments, increment sizes, search range limitations or other parameters affecting movement about the parameter space may be incorporated.

In addition, the feedback loop stimulation parameter control system 500 may allow the user to provide search range limitations to one or more of the stimulation parameters to limit the range for that stimulation parameter over which the system will search for parameters. For example, the user may restrict which electrodes can be used for stimulation or may restrict the amplitude or pulse width to a certain range or with a selected maximum or minimum. As one illustration, based on the site of implantation, the user may be aware that the distal-most and proximal-most electrodes are unlikely to produce suitable stimulation and the user limits the range of electrodes to exclude these two electrodes.

For a lead with segmented electrodes, the number of possibilities for parameter selection can be very large when combinations of electrodes and different amplitudes on each electrode are possible. In some embodiments using a lead with segmented electrodes, the selection of electrodes used for stimulation may be limited to fully directional selections (i.e., selection of only a single segmented electrode) and fully concentric selections (i.e., all electrodes in a single set of segmented electrodes are active with the same amplitude). In other embodiments, the initial movement through parameter space may be limited to fully directional and fully concentric selections. After a set of stimulation parameters is identified using these limits, variation in the selection of electrodes may be opened up to other possibilities near the selection in the identified set of stimulation parameters to further optimize the stimulation parameters.

In some embodiments, the number of stimulation parameters that are varied and the range of those variations may be limited. For example, some stimulation parameters (e.g., electrode selection, amplitude, and pulse width) may have larger effects when varied than other stimulation parameters (e.g., pulse shape or pulse duration). The movement through parameter space may be limited to those stimulation parameters which exhibit larger effects. In some embodiments, as the feedback loop stimulation parameter control system 500 proceeds through testing of sets of stimulation parameters, the system may observe which stimulation parameters provide larger effects when varied and focus on exploring variation in those stimulation parameters.

In at least some embodiments, the feedback loop stimulation parameter control system 500 includes a user interface (not shown in FIG. 5) for visualizing exploration of the stimulation parameter space as the system determines new and better parameter values to test until a solution is determined that fits within certain designated thresholds or a stop condition is reached. In some embodiments of the FLSPCS 500, the user interface is part of the pulse generator feedback control logic 501. In other embodiments, the user interface may be part of another computing system that is part of the FLSPCS 500 or may be remote and communicatively connected to the FLSPCS 500. The user interface may present to a user (such as a clinician, physician, programmer, etc.) a visualization of the predicted expected outcomes for (some of) the stimulation parameter values not yet tested and a recommendation for the next set of stimulation parameter values to test. An example of such a user interface for searching for an optimal set of stimulation parameter values is described with reference to FIGS. 6A-6J.

In some embodiments where a deep brain stimulator is actually configured via a controller 505 with at least one set of stimulation parameter values forwarded by pulse generator feedback control logic 501, the physician/clinician may monitor the patient throughout the process and record clinical observables in addition to the patient 506 being able to report side effects. When a side effect is observed/recorded, the various search algorithms will take that fact into account when selecting/suggesting a next set of values to test. In some embodiments, for example, those that select contacts via monopolar review, other parameters may be changed until they cause a side effect, which case is noted as a boundary. For example, in monopolar review where amplitude is another stimulation parameter being varied, the amplitude may be increased progressively until a side-effect is observed.

In some embodiments, more than one clinical metric (e.g., tremor, bradykinesia, etc.) may be important observables. Different embodiments of the FLSPCS 500 may handle these metrics differently. For example, some embodiments might identify an ideal location for each metric and choose one ideal location between them, set in the patient's remote controller so the patient can choose as needed, or chose a best combined outcome. As another example, some embodiments may search multiple outcomes at the same time and use the best combined score as the best outcome or find a best location for each metric individually. As yet another example, some embodiments may use a sequential process for selecting stimulation parameter values for multiple outcomes. For example, a system may search parameter space for a first outcome (e.g., bradykinesia) and, upon finding a suitable end condition, then search parameter space for a second outcome (e.g., rigidity). While searching parameter space for the first outcome, clinical response values for both the first and second outcomes can be obtained. Thus, when the system switches to the second outcome there are already a number of clinical response values for that outcome which will likely reduce the length of the search.

In some embodiments, two stimulation leads may be implanted to produce stimulation effects on two sides of the body (e.g., the right and left sides of the body). The same procedure described herein can be used to either jointly determine the stimulation parameters for the two leads by exploring the joint parameter space or individually determine stimulation parameters for the two leads by exploring the parameter space for each lead individually. In some embodiments, the user may determine for each side of the body which clinical response is dominant or most responsive. This may be done, for example, by having the patient perform a single task which captures multiple responses (e.g. connecting dots on the screen to monitor tremor and bradykinesia of the movement) or a small series of tasks. This enables the system to determine which clinical response to use to identify the stimulation parameters for that side of the body. #

As noted, the feedback may be provided directly by the patient 506, entered by an observer such as a clinician (not shown), or may be provided by means of a sensor 507 associated with and in physical, auditory, or visual contact with the patient 506. In an embodiment where the feedback can be monitored automatically or semi-automatically, such as with use of sensor 507, it may not be necessary for a clinician or other observer to be present to operate the FLSPCS 500. Accordingly, in such embodiments a user interface may not be present in system 500.

FIGS. 6A-6J are example display screens for a user interface for visualizing stimulation parameter determinations using the feedback loop stimulation parameter control system according to described techniques. Other user interfaces are possible. In the example demonstrated, searching the parameter space is emphasized to find optimal parameter values, where optimal is as described above: fastest time to outcome, best possible clinical outcome, and/or optimal with least battery usage. The stimulation parameters that can be varied in this example user interface are contact location and amplitude (in milliamps). Contact location may be specified as a single value of a contact along the axis of a lead for ring electrodes, and may have a x, y, z (around circumference) component to specify which segment is specified in a segmented or directional lead. In some embodiments the contact location may be a "virtual" contact location, meaning that the stimulation may be split in some fraction between two or adjacent contacts and the resulting stimulation has a centroid that lies between the two contacts, looking as though it's coming from a virtual contact in between the two or more contacts. Other embodiments and arrangements are possible.

Figure 6A:
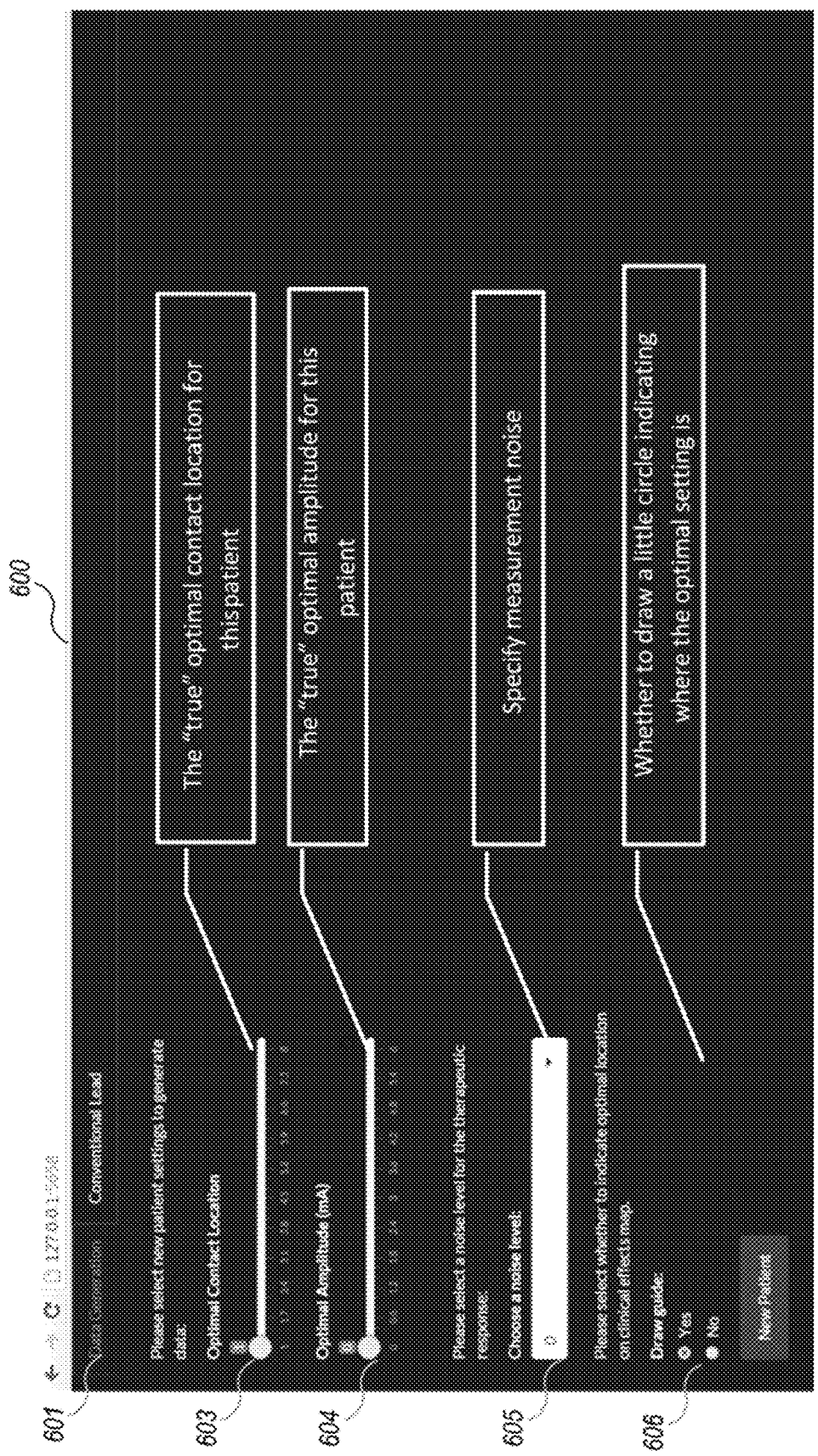

More specifically, in FIG. 6A, the display screen 600 shows initial data generation for a new patient. The data generation tab 601 shows a gauge for optimal contact location 603 and a gauge for optimal amplitude 604. The values for these gauges are determined as a result of running the feedback loop stimulation parameter control system (system 500 in FIG. 5), presented here as an application. Noise level indicator 605 specifies the measurement noise for the therapeutic response and is measured on a scale from 0 to 4 (other scales may be used). Radio button 606 indicates whether the program should draw a circle indicating the location of the optimal setting on the clinical effects map.

In FIG. 6B, the display screen 600 has been randomly filled out for this patient since no previous data exists. If it did, screen 600 would reflect those values.

Figure 6C:
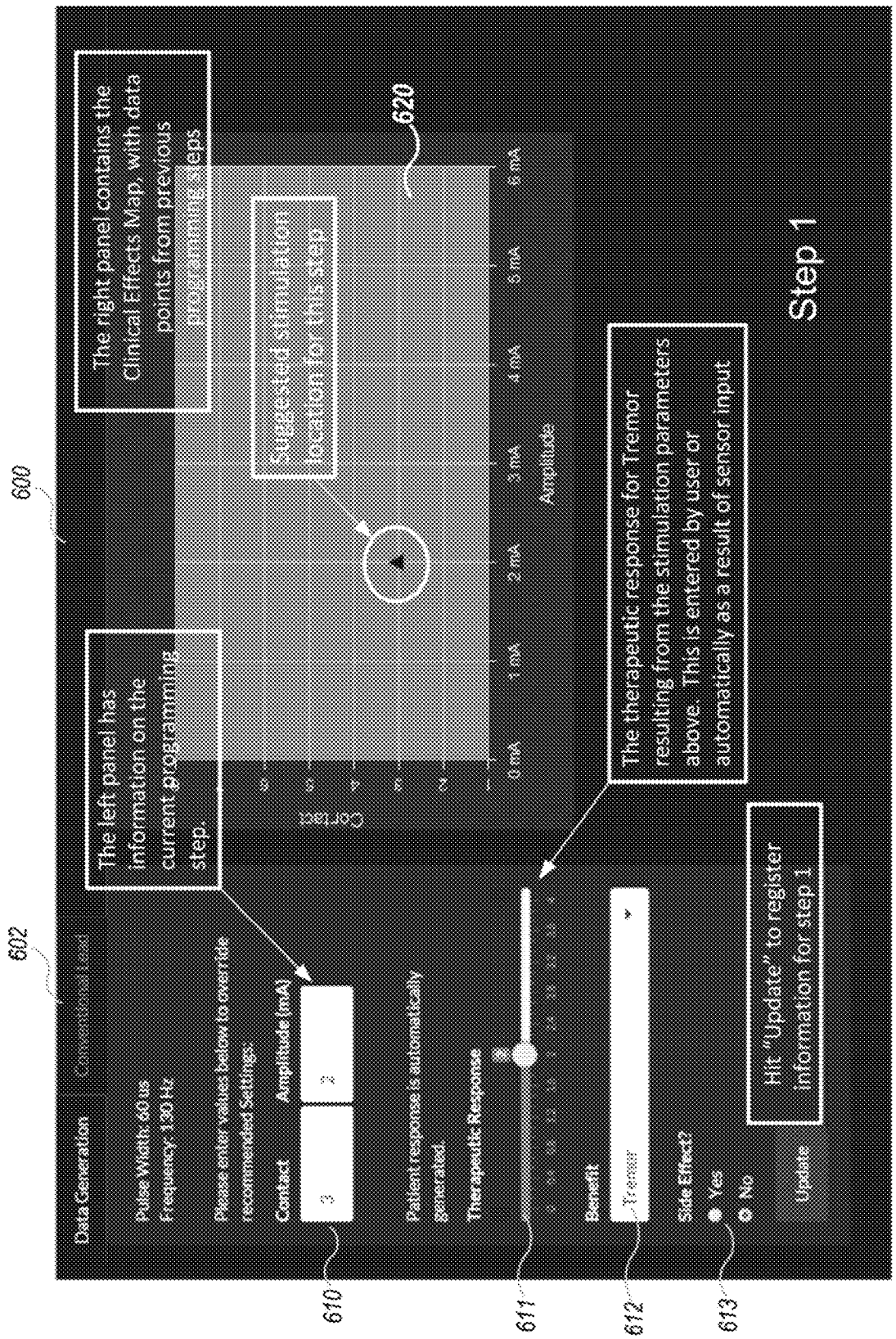

In FIG. 6C, the user has changed the display screen 600 to the conventional lead data determination tab 602. Here, as in each subsequent step, the feedback loop stimulation parameter control system shows the therapeutic response 611 (the observables) that results from programming the deep brain stimulator controller (e.g. controller 505 in FIG. 5) with the parameter values 610 indicating contact location and amplitude values that the system suggests. The user (e.g. a clinician) may overwrite these values in fields 610. Of course different values would be pertinent and potentially different numbers of fields shown if different parameters are being determined and tested. The system also shows the stimulation parameter values that have been tested so far in clinical effects map 620.

Figure 6D:
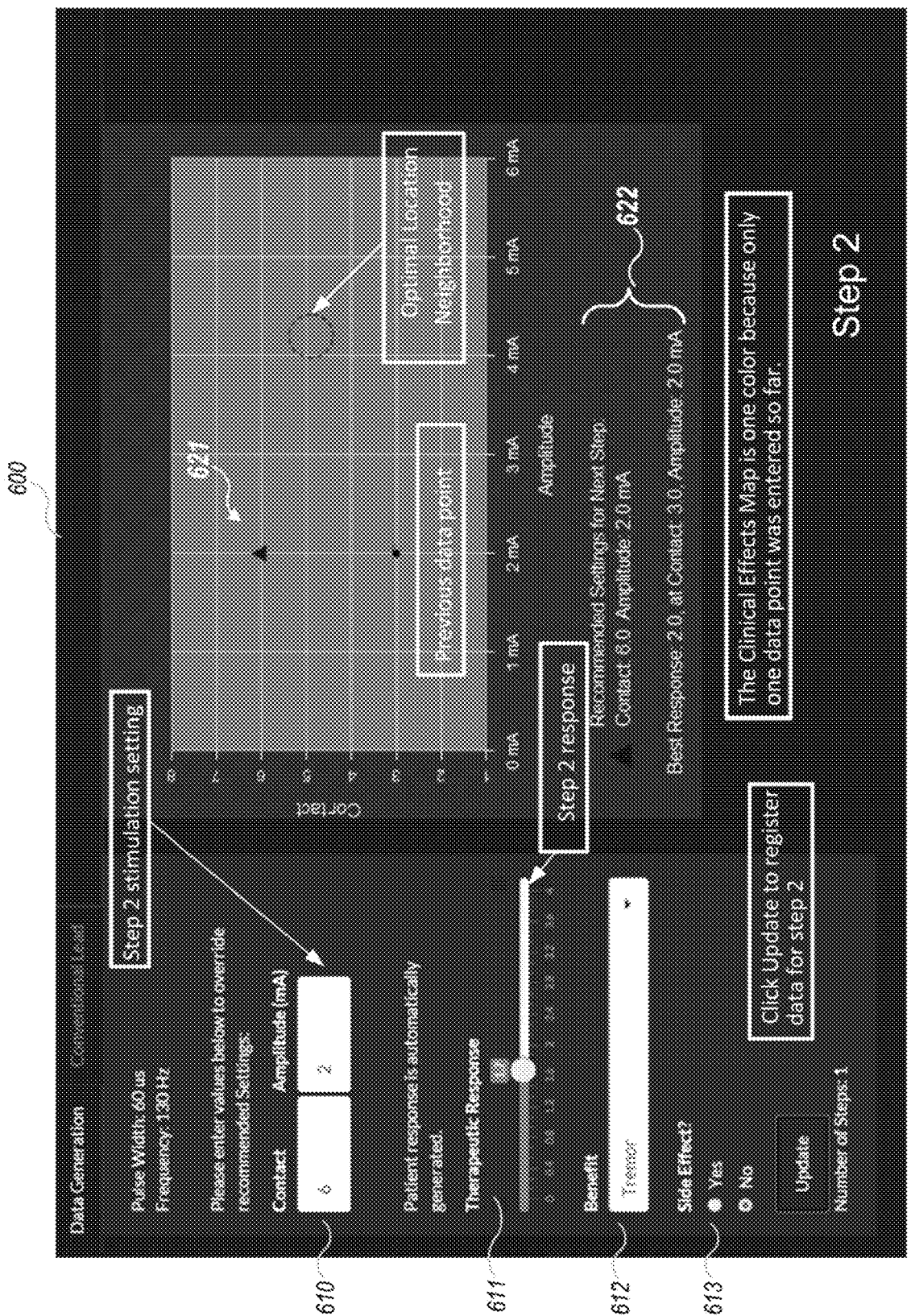

In FIG. 6D, the feedback loop stimulation parameter control system shows the therapeutic response 611 at 1.7 for the stimulation parameter values (contact=6, amplitude=2) in fields 610. When the controller is programmed to these values, therapeutic response measurements 611 are shown with respect to tremor. The therapeutic response 611 for other benefits can be shown by selecting a different benefit using the pulldown menu 612. Any side effects can be indicated using radio buttons 613. In this instance there is no side effect noted. As at each step, if the clinician (or other user) wants to accept these values as data to be incorporated into the model, the clinician selects the update button. At this point the clinical effects map shows only one previous data point (from step 1 of programming the controller, described with reference to FIG. 6C). The next suggested set of stimulation parameter values (this step of programming) is shown in the map as triangle 621. Comments 622 track the best clinical response observed thus far (step 1 values).

Figure 6E:
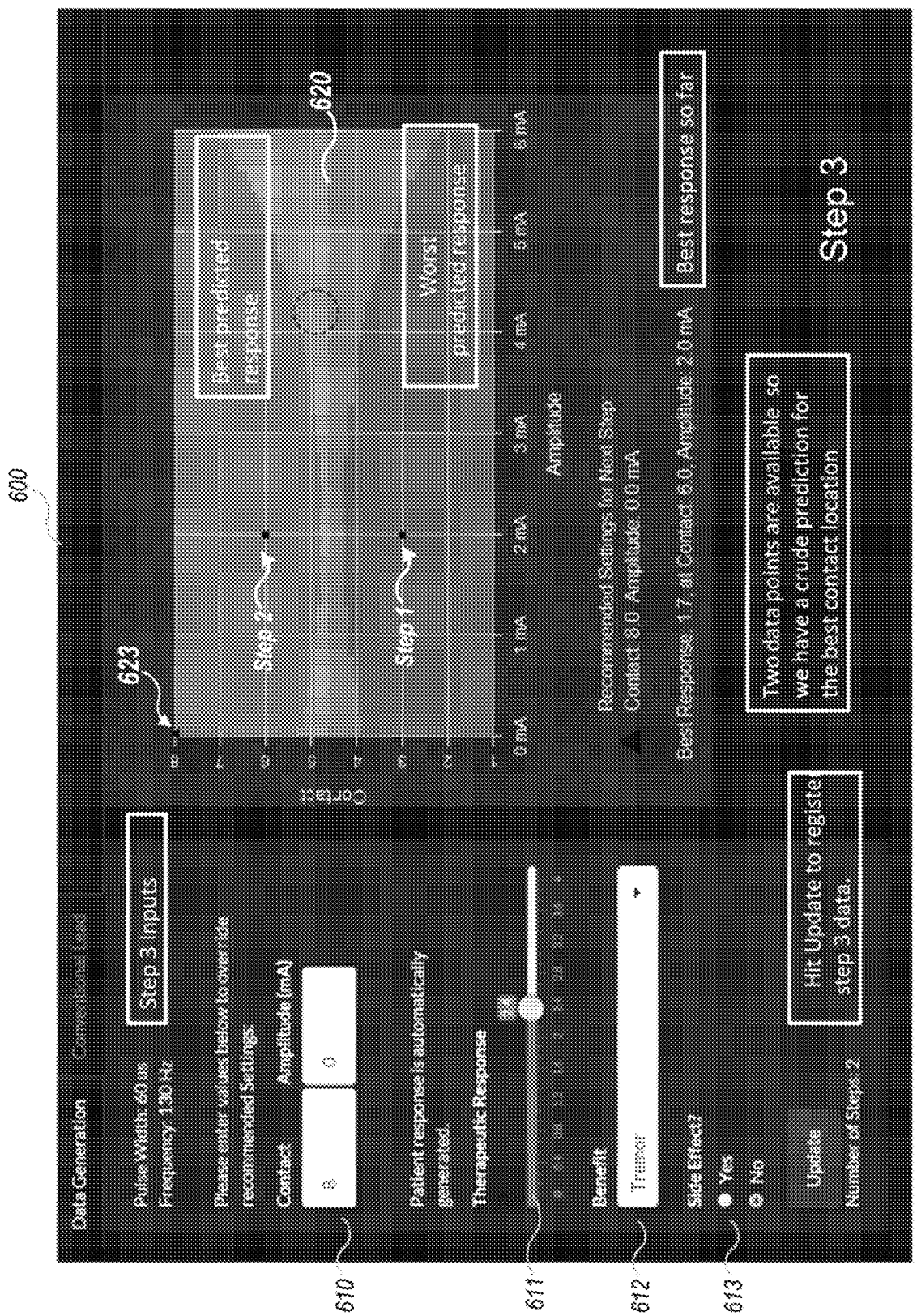

In FIG. 6E, the feedback loop stimulation parameter control system displays in screen 600 the results of suggested stimulation parameter values for step 3 of programming the controller. In this case the values 610 are for contact=8 and amplitude=0. The observed therapeutic response 611 is 2.4 for tremor (benefit 612) and there is no side effect indicated (613). Pressing the update button enters the step 3 data into the system. The clinical effects map 620 shows both prior steps of programming and indicates where this step (recommended values for the next step) falls on the map (location 623). Of note, as the machine learning engines are given more data, they are able to predict based upon the data what sets of values are likely to lead to the best predicted response (upper portion of FIG. 6E and, in one embodiment, colored purple) and what sets of values are likely to lead to the worst predicted response (lower portion of FIG. 6E and, in one embodiment, colored dark grey). In the subsequent Figures, the colorations or shadings change because more data is processed and the models become more complete. How the system determines the next set of stimulation parameter values is described with respect to FIGS. 7 and 8.

In some embodiments, the feedback loop stimulation parameter control system may suggest to the user the amount of wash-in time to wait after applying stimulation at the particular stimulation settings before obtaining a clinical response value. In at least some cases, it is found that when stimulating at new parameters which are close in proximity to the stimulation parameters which immediately preceded them (e.g. stimulating using an electrode at 2 mA, then stimulating using the same electrode at 2.5 mA), that there does not need to be as long of a wash-in time as when the parameters are far apart. Based on the distance from the previous stimulation parameters, the system can suggest an appropriate wash-in time. Alternatively or additionally, it may be desirable to test the patient's specific wash-in time for the specific clinical response being evaluated. For instance, at the start of a programming session, the patient would be programmed with some generic, acceptable stimulation parameters and we would measure the clinical response every 30 seconds and then observing how long after initially changing the settings it would take for the response to asymptote and come to a steady response. That would be used as the wash-in time for that patient or hemisphere.

Figure 6F:
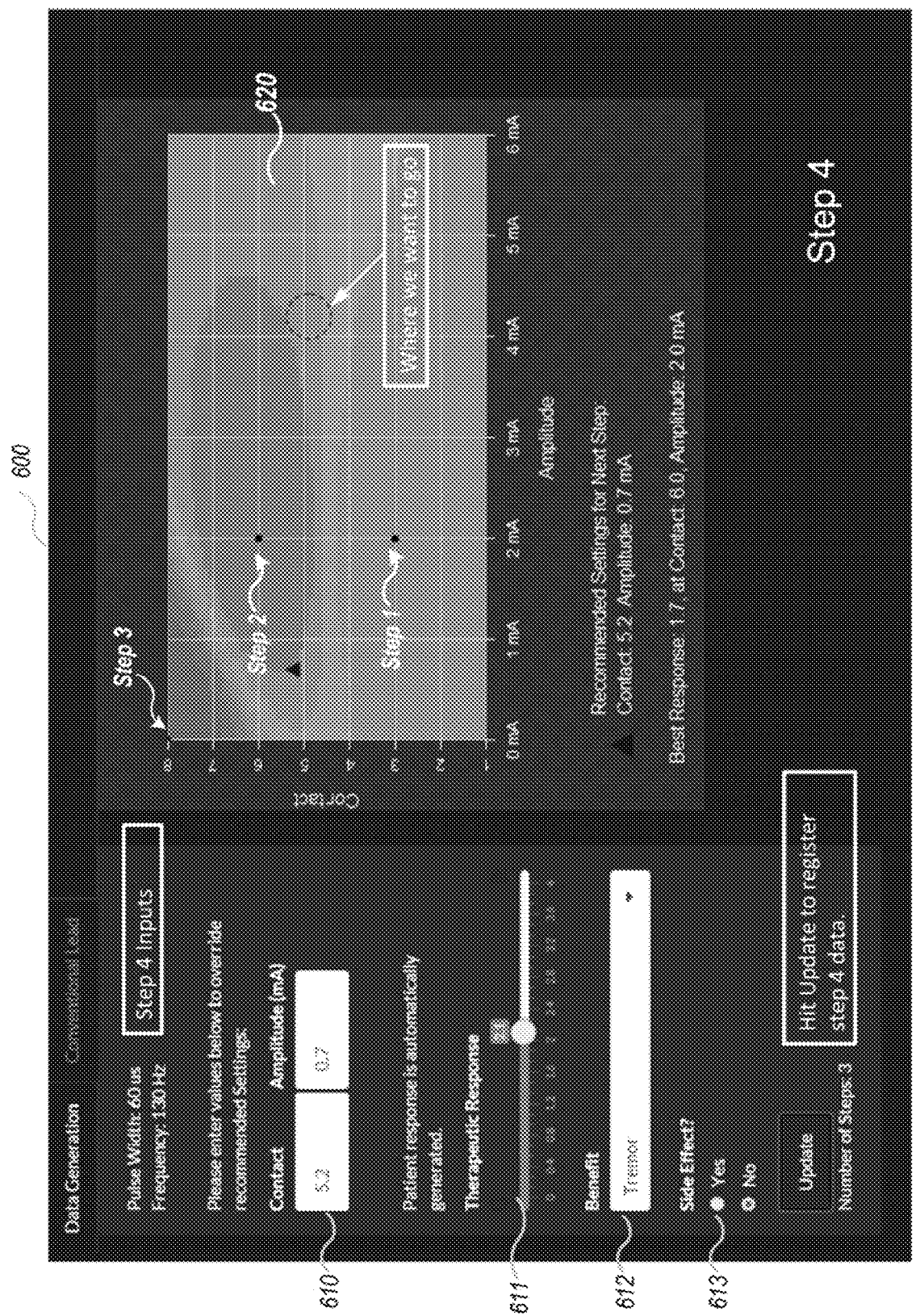

In FIG. 6F, the feedback loop stimulation parameter control system displays in screen 600 the results of suggested stimulation parameter values for step 4 of programming the controller. In this case the values 610 are for contact=5.2 and amplitude=0.7. The observed therapeutic response 611 is 2.1 for tremor (benefit 612) and there is no side effect indicated (613). Pressing the update button enters the step 4 data into the system. The clinical effects map 620 shows all three prior steps of programming and where they fall into the predicted best and worst response ranges (for example, purples and greys) based upon the data processed thus far. It also indicates where this step (recommended values for the next step) falls on the map (the triangle). It can now be seen that the step 2 values, which are indicated in the comment area as the best response tracked so far, are right in the center of the best predicted response area.

Figure 6G:
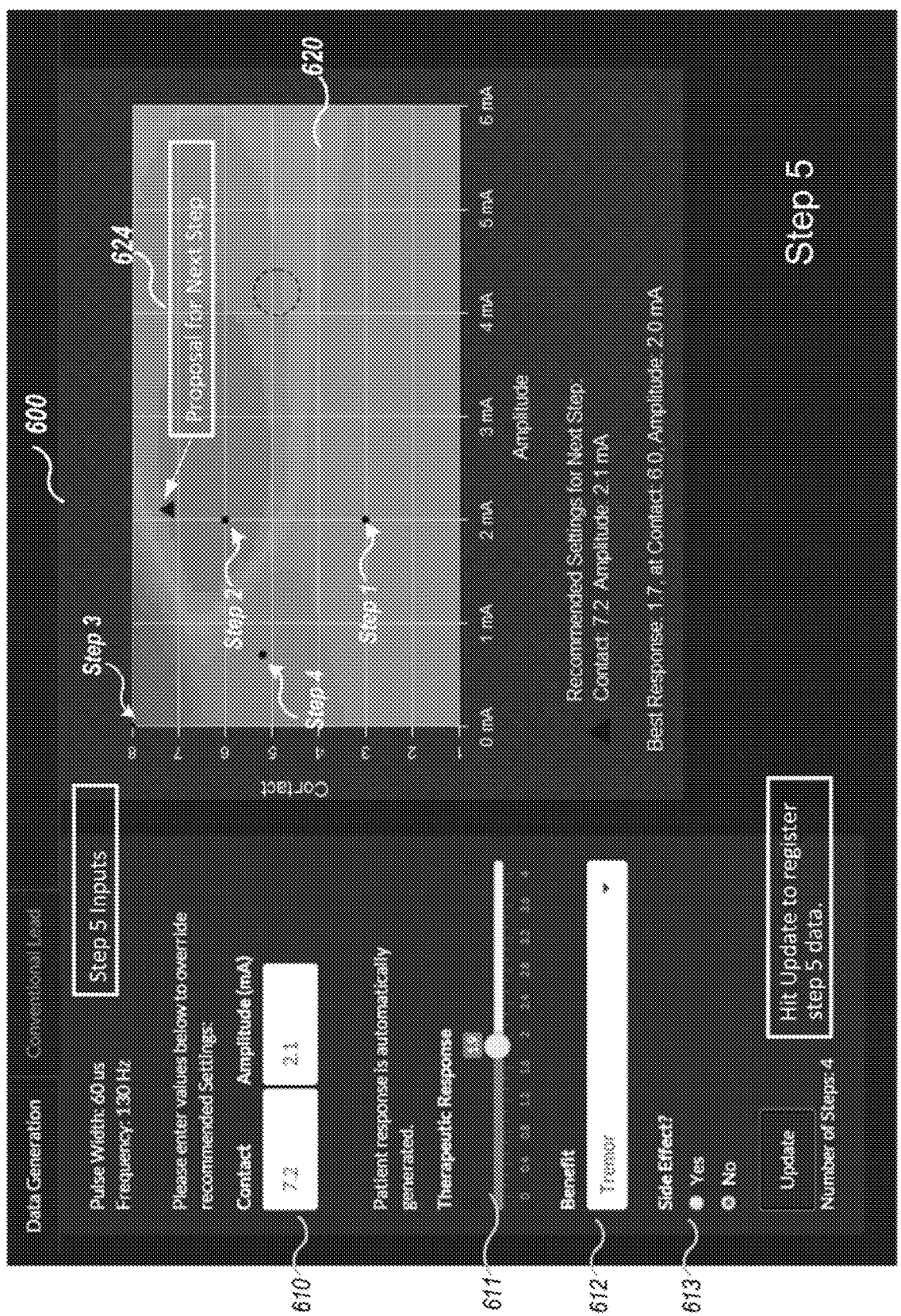

In FIG. 6G, the feedback loop stimulation parameter control system displays in screen 600 the results of suggested stimulation parameter values for step 5 of programming the controller. In this case the values 610 are for contact=7.2 and amplitude=2.1. The observed therapeutic response 611 is 1.9 for tremor (benefit 612) and there is no side effect indicated (613). Pressing the update button enters the step 5 data into the system. The clinical effects map 620 shows all four prior steps of programming and where they fall into the predicted best and worst response ranges (for example, purples and greys) based upon the data processed thus far. It also indicates where this step 624 (recommended values for the next step) falls on the map (the triangle). It can still be observed that the step 2 values, which are indicated in the comment area as the best response tracked so far, are in the best predicted response area, although no longer centered.

Figure 6H:
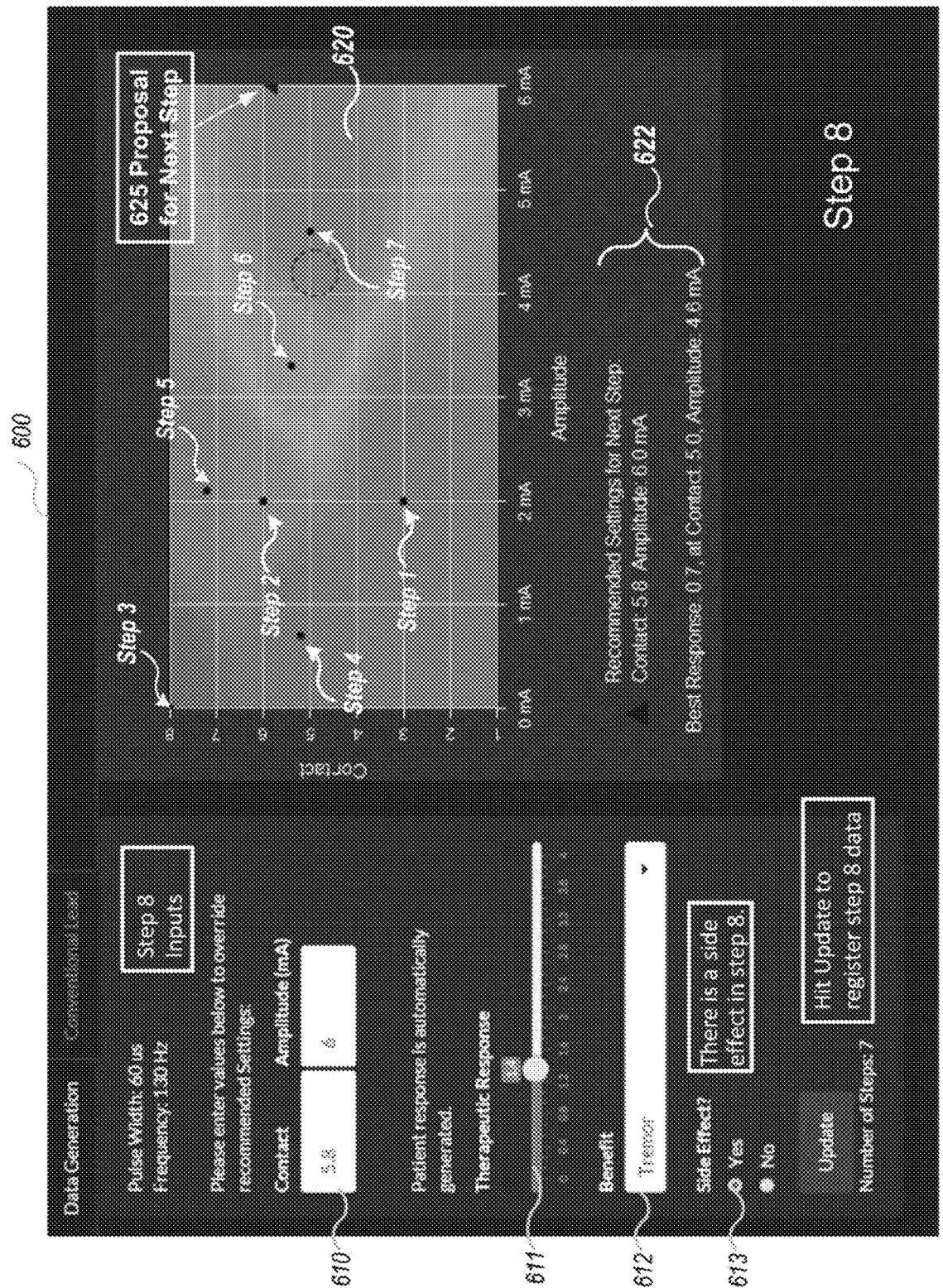

FIG. 6H shows the display screen 600 corresponding to programming step 8. The three intervening steps are not shown. In this step, the values 610 are for contact=5.8 and amplitude=6. The observed therapeutic response 611 is 1.4 for tremor (benefit 612) but there is a side effect indicated (613). Pressing the update button enters the step 8 data into the system. The clinical effects map 620 shows all seven prior steps of programming and where they fall into the predicted best and worst response ranges (for example, purples and greys) based upon the data processed thus far. It also indicates where this step 625 (recommended values for the next step) falls on the map (the triangle). The best response tracked so far has now been changed to the step 7 results.

Figure 6I:
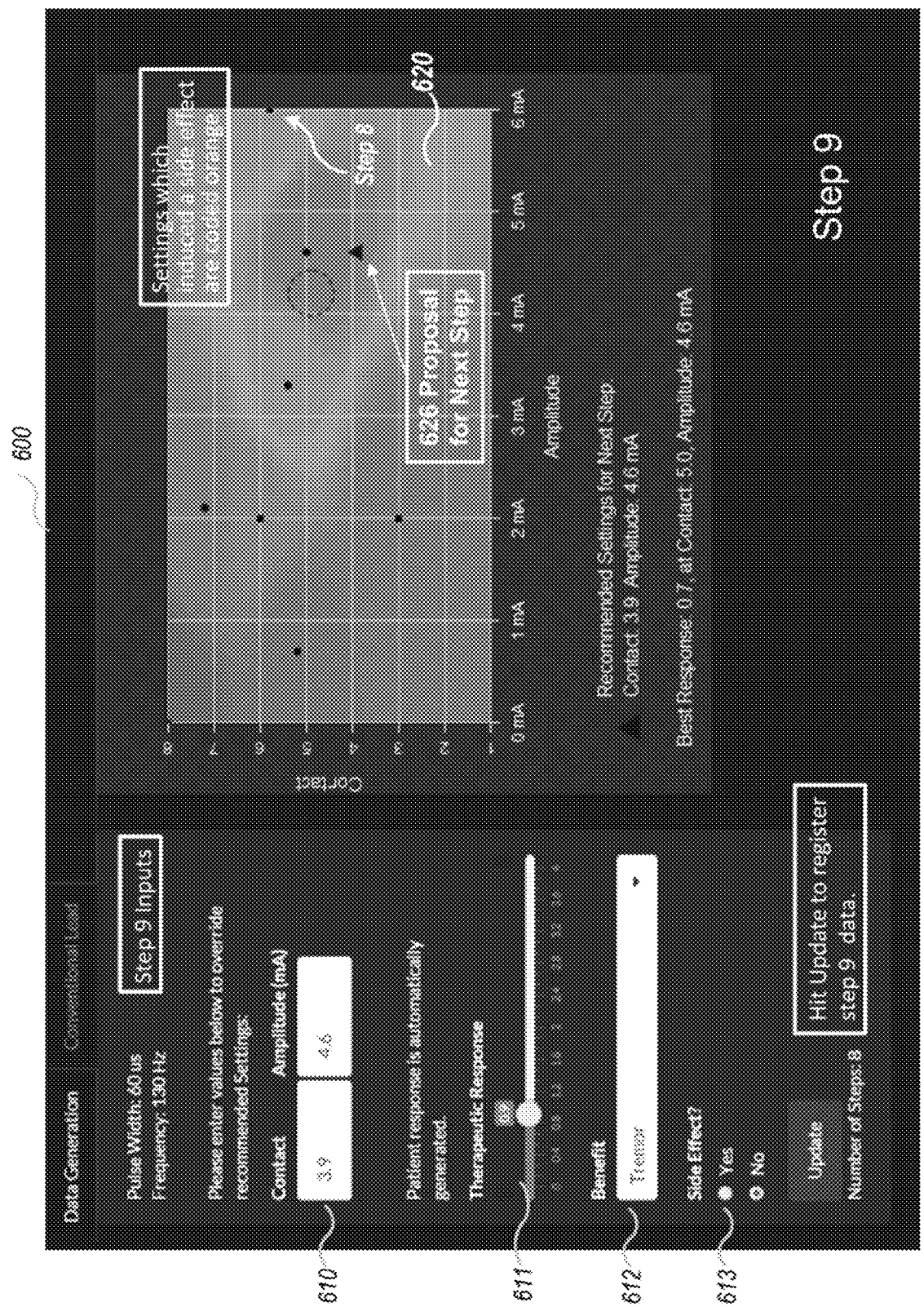

In FIG. 6I, the feedback loop stimulation parameter control system displays in screen 600 the results of suggested stimulation parameter values for step 9 of programming the controller. In this case the values 610 are for contact=3.9 and amplitude=4.6. The observed therapeutic response 611 is 0.9 for tremor (benefit 612) and there is no side effect indicated (613). Pressing the update button enters the step 9 data into the system. The clinical effects map 620 shows all eight prior steps of programming and where they fall into the predicted best and worst response ranges (for example, purples and greys) based upon the data processed thus far. Of note, any prior response (e.g., step 8) which produced a side effect (undesired) are coded differently. It also indicates where this step 626 (recommended values for the next step) falls on the map (the triangle). The best response tracked so far remains the step 7 results.

Figure 6J:
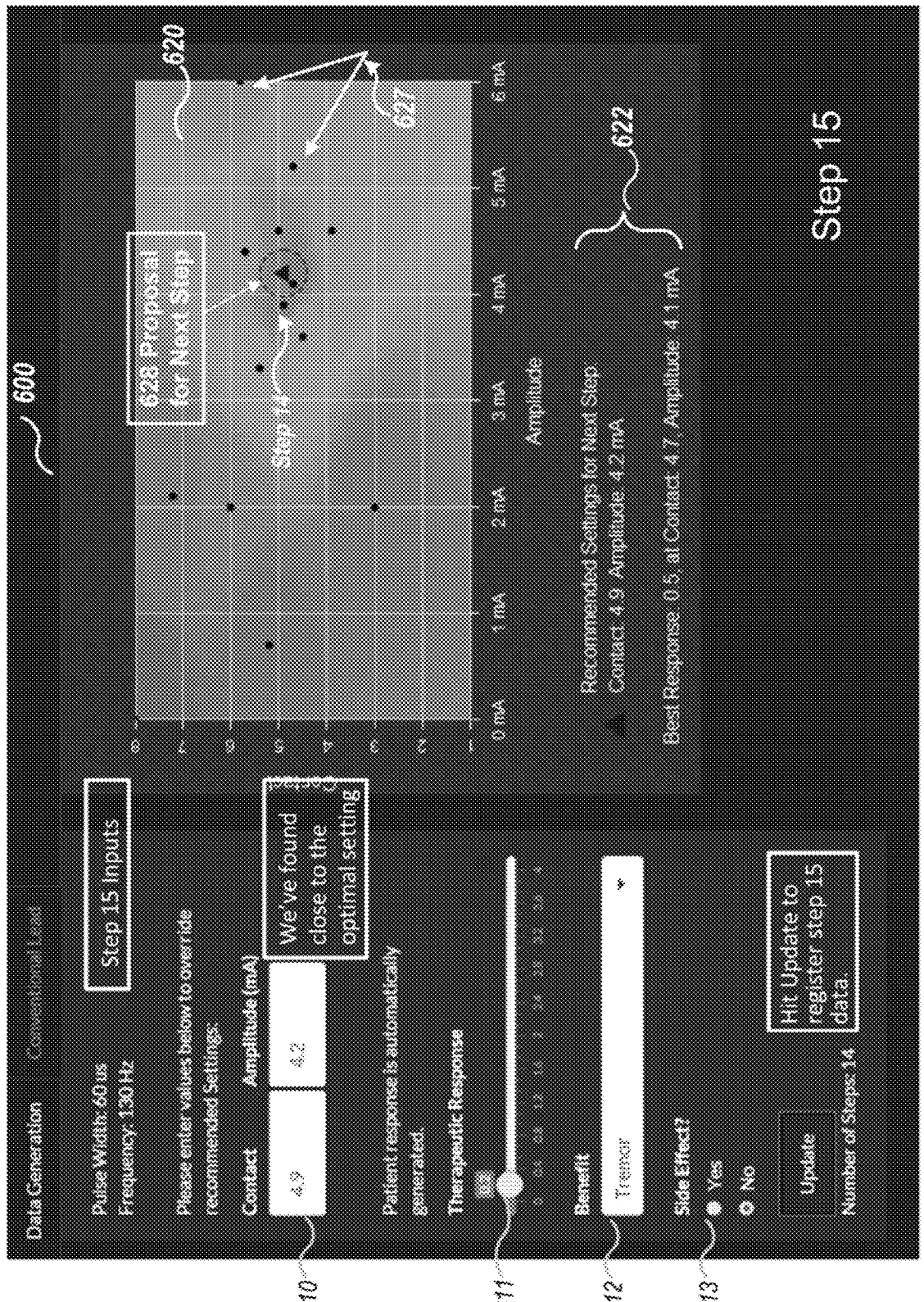

In FIG. 6J, the feedback loop stimulation parameter control system displays in screen 600 the results of suggested stimulation parameter values for step 15 of programming the controller (steps 10-14 are not shown). In this case the values 610 are for contact=4.9 and amplitude=4.2. The observed therapeutic response 611 is 0.2 for tremor (benefit 612) and there is no side effect indicated (613). Pressing the update button enters the step 15 data into the system. The clinical effects map 620 shows all fourteen prior steps of programming and where they fall into the predicted best and worst response ranges (for example, purples and greys) based upon the data processed thus far. Of note, the prior responses that produced side effect 627 are coded differently. It also indicates where this step 628 (recommended values for the next step) falls on the map (the triangle). The best response tracked so far is now the step 15 results. At this point, the programming may continue to run or stop as the values are converging into a best predicted zone. Other stop conditions may be incorporated such as number of iterations, time, subjective determination of the user, or the like.

Figure 6K:
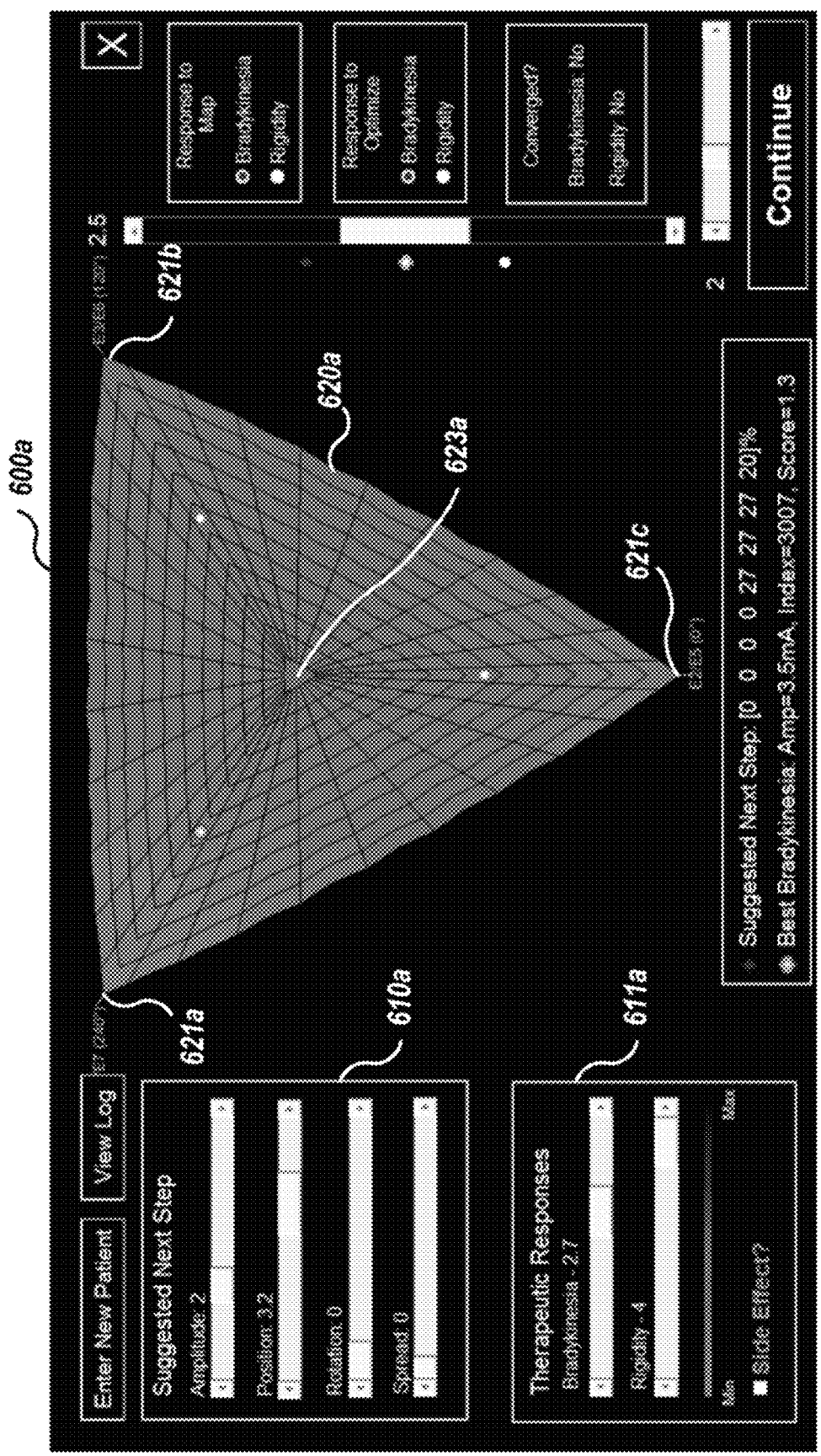

FIG. 6K illustrates an alternative screen 610a for use with sets of segmented electrodes and representing a clinical effects map 620a. The system may allow the user to move up or down the lead displaying a different clinical effects map for each set of segmented electrodes. In this case, there are three segmented electrodes in each set (see, for example, FIGS. 3F-3H) with each apex 621a, 621b, 621 of the triangle corresponding to stimulation using only one of the electrodes and positions between the apexes corresponding to combinations of electrodes. The amplitude of stimulation is represented by distance from the center of the diagram 623a. The parameter values 610a for the next set of stimulation parameters are presented, as well as therapeutic response measurements 611a. With respect to the parameter values 610a, the "Position", "Rotation", and "Spread" values refer to electrode selection with position being the longitudinal position along the lead, rotation being the angular direction of stimulation, and spread related to the angular width of the stimulation. These parameters are discussed in more detail in U.S. Provisional Patent Application Ser. No. 62/480,942, which is incorporated herein by reference.

As described with reference to FIG. 5, the feedback loop stimulation parameter control system 500 determines and sends stimulation parameters to configure a deep brain stimulator controller 505. The deep brain stimulator controller 505 modifies the stimulation parameters of an implanted device (or test device), and, iteratively, based upon feedback, adjusts the stimulation parameters sent to configure the controller until a desired outcome or stop condition is reached.

Figure 7:
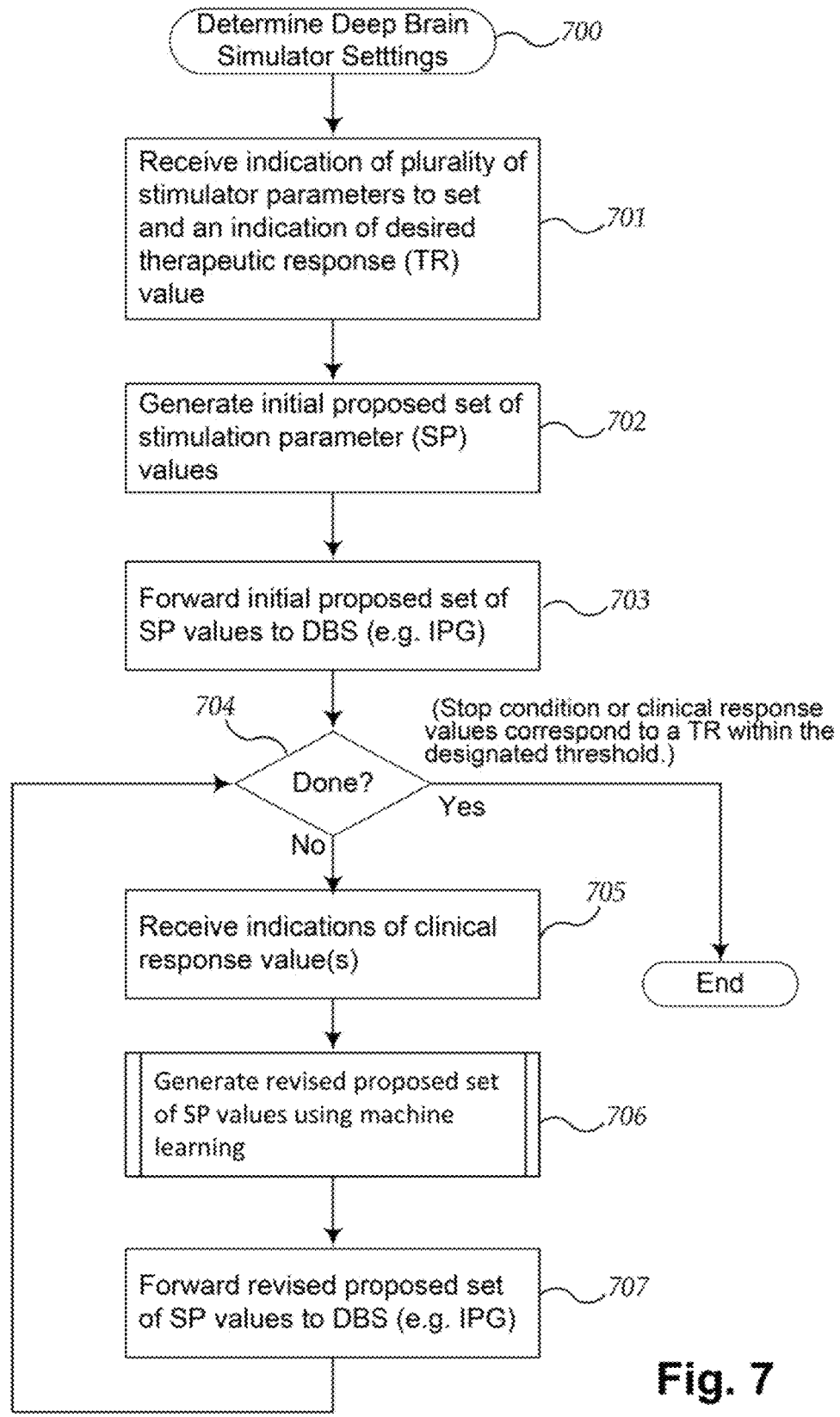
FIG. 7 is an example flow diagram of an example method for determining electrical simulator programming settings according to described techniques.

FIG. 7 describes an example method 700 for determining deep brain simulator programming settings according to an example feedback loop stimulation parameter control system such as system 500. Specifically, in block 701, the logic (such as pulse generator feedback control logic 501 in FIG. 5) receives an indication of a plurality of stimulation parameters to set and an indication of a desired therapeutic response. For example, in the example user interface described with reference to FIGS. 6A-6J, the set of stimulation parameters being adjusted comprise contact location and amplitude. It is possible to include other stimulation parameters in the set, for example, pulse width and frequency. Directional leads may include additional parameters including x, y, and z coordinates, angle, and shape. Thus, the set of stimulation parameters is potentially large. In addition, directional leads may be parameterized in other ways, including describing the location and shape of the stimulated tissue using:
1. The centroid of the stimulation (x, y, z coordinates) plus amplitude.
2. The centroid of the stimulation (x, y, z coordinates) plus single value to describe the radius.
3. The centroid of the stimulation (x, y, z coordinates) plus three values to describe the radii (also x, y, z).
4. The centroid of the stimulation (x, y, z coordinates) plus volume.
5. The centroid of the stimulation (x, y, z coordinates) plus two values to describe cross-sectional surface areas (e.g. x-y and y-z).
6. Pre-computing the volumes for each of the steering states that are created by our programming controls. Typically, the volumes generated are coherent volumes which are approximately spherical. These generated volumes could then be searched for the volume that is most closely aligned with the desired volume and the corresponding stimulation setting identified.
7. Using the three cylindrical coordinates (z, theta, r) to approximate the longitudinal position, rotational position, and amplitude (ignoring spread control).
8. Current fractionalizations assigned to each contact, plus overall amplitude (this would be 9 dimensions, and would likely require a method such as machine learning to handle).
9. Dividing the process up into several stages, where "Ring Mode" is first used to search for best longitudinal position and amplitude, then best rotational position and amplitude, and then best spread and amplitude. Ring Mode refers to stimulation settings where the electrodes on any active directional row of a lead can be treated like a cylindrical electrode by activating them at approximately the same percentage (e.g., 33% for a row with three electrodes).

In block 702, the logic generates an initial proposed set of stimulation parameter (SP) values. These include a value for each stimulation parameter being adjusted. For example, when the set of stimulation parameters include contact location and amplitude, the initial proposed set may be "contact=3" and "amplitude=2 mA" as shown in FIG. 6C.

In one example embodiment, the initial proposed set of stimulation parameter values is chosen arbitrarily because data has not been collected yet for this patient. In another example embodiment, the logic is expanded to use the distribution of optimal settings (e.g. amplitude and/or contact location) from previous patients to pick the starting setting for a new patient. This allows clinicians to begin the programming session with settings that other patients have found beneficial. In addition, new patients may be matched to previous patients via external information, such as diagnosis, imaging data, or baseline symptom severity.

In block 703, the logic forwards the initial proposed set of stimulation parameter values to the deep brain stimulator. In one embodiment, this is done by forwarding the parameter values to the DBS controller (see message 504 in FIG. 5) which adjusts the actual implanted device.

In blocks 704-707, the logic performs a loop (iterates) to received therapeutic responses, predict and propose new stimulation parameter values to try, and forwards them to set the DBS, until a stop condition is reached or a clinical response value that corresponds to a therapeutic response that is within a designated threshold is reached.

Specifically, in block 704, the logic determines whether an end condition is reached. For example, the logic may determine whether a clinical response has been received that corresponds to a therapeutic response within a designated threshold. For example, if tremor is what is being observed, a (beneficial) therapeutic response that is under 2.0 (on a scale of 0 to 4) may be considered a sufficient stopping point. In some embodiments, other stop conditions are designated such as a certain number of iterations has been performed, the therapeutic response changes less than x % with y number of iterations, or the user is satisfied with the result. Other stop conditions are possible.

In block 705, the logic receives indications of clinical response values. As discussed above, these values may be received from a patient by observation, or directly from a sensor associated with the patient, for example, an accelerometer located on the patient's wrist. In some embodiments, the indications of clinical values may be received from a clinician or physician observing the patient.

In block 706, the logic executes additional logic steps to generate a revised proposed set of stimulation parameter values incorporating machine learning techniques. Examples of these additional steps are described in further detail with reference to FIG. 8.

In block 707, the logic forwards the revised proposed set of stimulation parameter values to set the DBS to the revised values and returns to the beginning of the loop in block 704.

In some embodiments, steps 704 through 707 are performed for a first therapeutic response while obtaining clinical response values for both the first therapeutic response and a second therapeutic response. After finding the end condition for the first therapeutic response, steps 704 through 707 can be performed for a second therapeutic response. This procedure can be repeated for other therapeutic responses and provides a sequential process for selecting stimulation parameter values to obtain multiple therapeutic effects. For example, the first therapeutic effect may be bradykinesia and the second therapeutic effect can be rigidity. Steps 704 through 707 are preformed until an end condition is found for bradykinesia, although clinical response values are obtained for both bradykinesia and rigidity. Thus, when steps 704 through 707 are subsequently performed for rigidity, there are already a number of clinical response values existing for rigidity.

In addition, these techniques described by FIG. 7 may be used for stimulation of multiple leads. If the resulting solution produces multiple locations which are optimal (either for the same clinical response or two or more different clinical responses), the logic could subsequently identify settings which best stimulate both locations, either at the same time or at different times.

Figure 8:
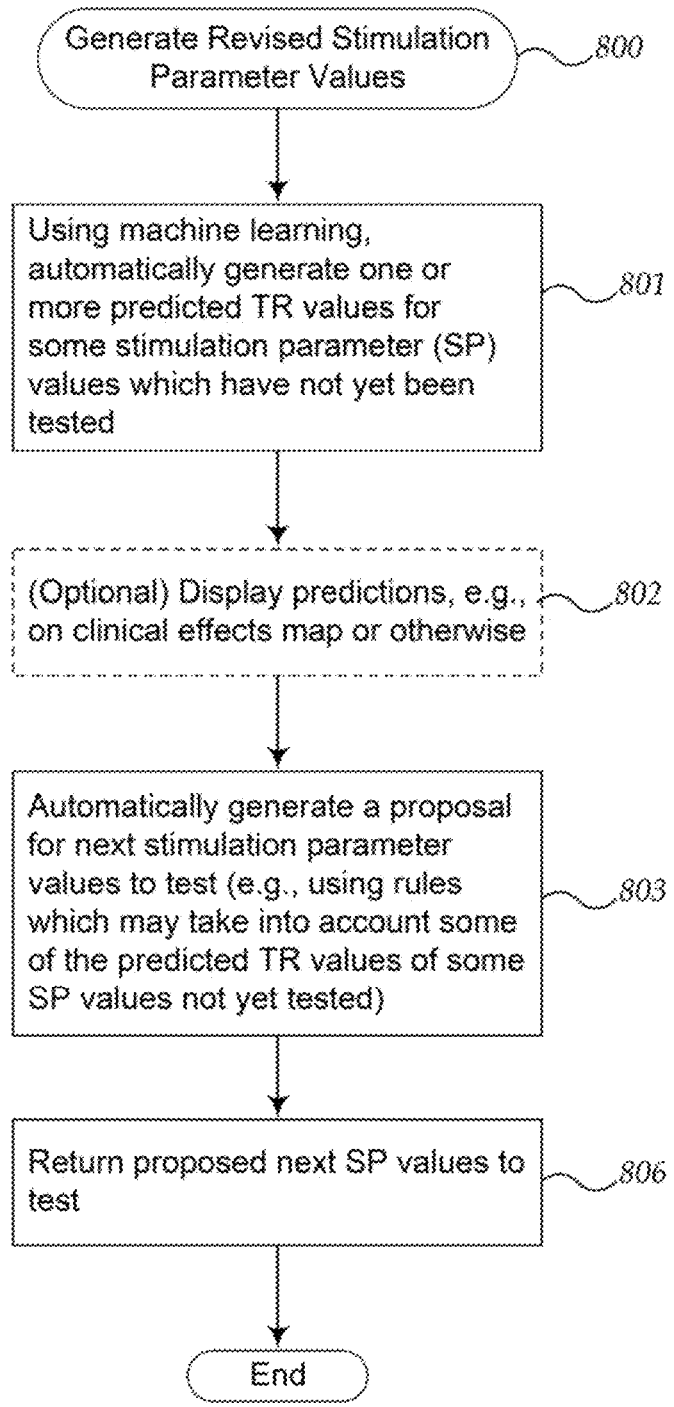
FIG. 8 is an example flow diagram of an example method for generating, using predicted therapeutic response values, a revised proposed set of stimulation parameter values to test.

FIG. 8 describes an example method 800 for generating a revised proposed set of stimulation parameter values using machine learning techniques. In particular, the logic comprises two phases: 1) a prediction phase where a therapeutic response is predicted using machine learning for some number of values that have not yet been tested/tried; and 2) a proposal phase where the logic suggests the next set of stimulation parameter values based upon the results of the prediction phase and a set of rules/heuristics. As discussed above, measured clinical response values may be weighted based on the time at which the testing occurred due to test fatigue or other factors. For example, more recent clinical response values may be weighted more than earlier clinical response values as the more recent clinical response values are more predictive of the therapeutic responses.

Specifically, in block 801, the logic automatically generates, using machine learning techniques, one or more therapeutic response values for stimulation parameter values that have not yet been tested. For example, in an embodiment in which the set of stimulation parameters include two parameters: contact location and amplitude, it may be desirable to visualize (and set) the values for contact location from 1 to 8 and amplitude from 0 mA to 6 mA in 0.1 increments. If one were to visualize these possible values on a clinical effects map (like clinical effects map 620 in FIG. 6C), these possible values would result in 4331 grid locations (71×61). The logic allows for 10% of total current delivered to be shifted between adjacent contacts, and the location along the contact axis tracks the centroid of the volumes (i.e. location 2.3 means that contact 2 has 70% of the current and contact 3 has 30%). In other example embodiments different amounts of current can be shifted between contacts.

At programming step t+1 (e.g., iteration of the loop shown in FIG. 7), there is a training data set, comprised of "X" a t×m matrix of stimulation settings and "y" a t×1 vector of therapeutic responses, where t denotes the number of already tested settings and m denotes the number of stimulation parameters. The goal is to predict a therapeutic response for each of the (4331−t) untested settings based on the training data.

Figure 9:
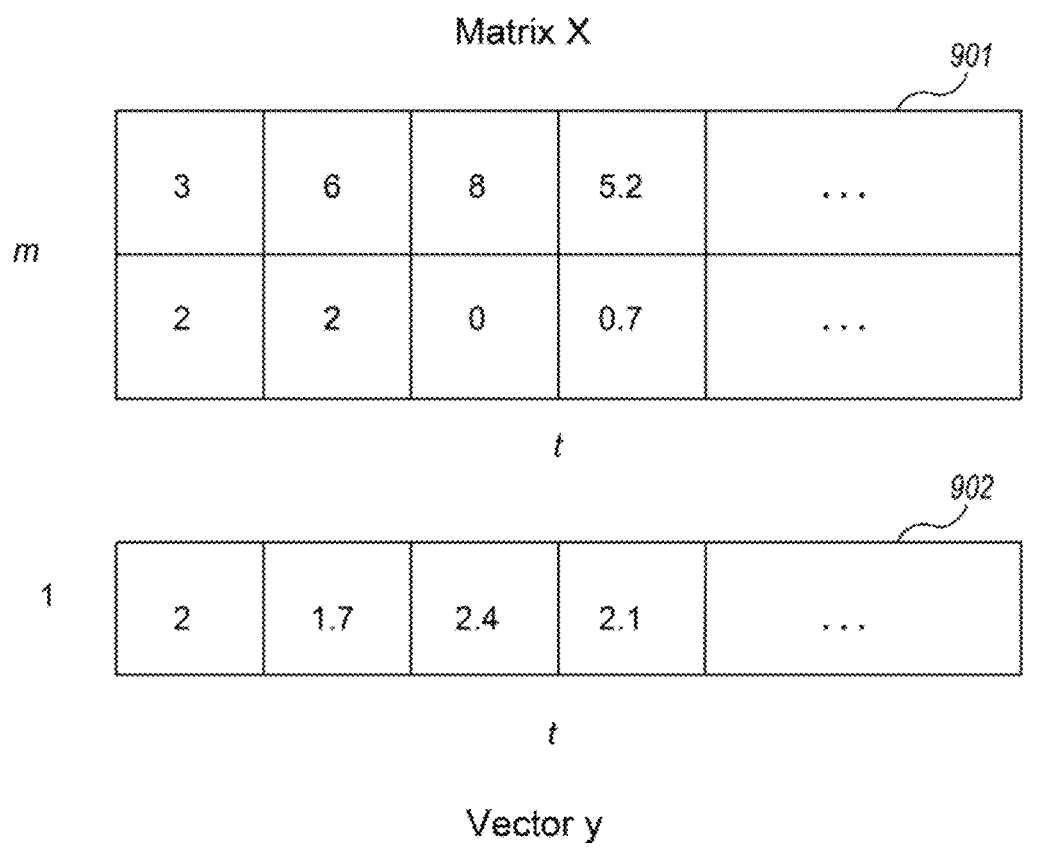

For example, if m=2 (contact location and amplitude), then "X," the t×m matrix, may be represented as a sparse matrix 901 illustrated in FIG. 9. The values shown in matrix 901 are the same as those in the example programming steps 1-4 shown in FIG. 6C-6F. The vector "y" 902 in FIG. 9 shows the corresponding therapeutic response values.

A number of machine learning methods can accomplish this task as described earlier. If there are two or more adverse symptoms to control, then the prediction phase may generate a separate prediction for each therapeutic response for each matrix location. Alternatively, the prediction phase may generate a combined score based upon combining the multiple systems in a variety of ways, including weighting them based upon importance, aggregating them, and the like.

In some embodiments, multiple machine learning methods may be used (concurrently) to generate multiple predictions and the results scored in some manner. For example, when programming deep brain stimulators, patient response to stimulation is unlikely to follow an established parametric distribution, is prone to noise, and is patient-specific. In some embodiments, predictions from several machine learning methods can be stored in memory and then analyzed for accuracy after new data are collected. Machine learning methods that produce accurate predictions will be "up-voted" while methods that produce inaccurate predictions will be "down-voted". This process allows high performing prediction methods to drive the search process, as a single method may be unlikely to work for all patients or for the entire duration of a programming session.

The prediction techniques of block 801 could also take into account previously acquired local field potential (LFP) data, which would give an approximation of the prediction space.

In block 802, the logic optionally displays or presents the predictions resulting from block 801. As noted in FIGS. 6A-6J, when the set of stimulation parameters is small, for example contact location and amplitude, it is possible to visualize responses from each iteration of programming the DBS using a clinical effects map. As additional stimulation parameters are added, this becomes more difficult. In addition, coming up with a proposal for a next set of stimulation parameter values also becomes more challenging.

In at least some embodiments, a confidence score can be generated and displayed to indicate the likelihood that the predictions will produce a good outcome or the predicted outcome. For example, the confidence score may be based on repeatability of the responses (e.g. if the same or similar settings are used or predicted and the responses vary too much, the outcome may be questionable), or the confidence score may be based on robustness of the clinical response (e.g. if all of the patient responses are a 3.9 or 4.0 out of 4, then the procedure will likely not converge to a good solution).

In block 803, the logic performs phase two of the process: it automatically proposes a next set of stimulation parameters to test. In an example embodiment, this phase takes into account one or more of the predictions of therapeutic responses for parameter values that have not yet been tested and may also incorporate rules and/or heuristics to provide more efficient selection of a next proposed set of stimulation parameter values. In some embodiments, the rules/heuristics are directed to eliminating those values that are unlikely to yield desirable results for one reason or another. For example, in one embodiment, inappropriate grid locations are eliminated using a set of rules, then the R remaining locations are ranked in different ways according to predefined criteria, for example from 1="best" to R="worst." In this case, the grid location chosen for the next programming step is the location with the lowest overall rank. In some embodiments, an option is provided where several of the top candidates are returned, thereby giving the programmer/clinician more manual control over the programming path. In addition, an option to completely override the suggestion(s) provided by the logic is also possible.

In one embodiment, the following example rules are incorporated to eliminate inappropriate sets of stimulation parameter values (e.g. locations in the grid of 4331 values):
1. Cannot be one of the last 10 settings (values) tested, i.e. re-testing is possible though unlikely.
2. Cannot be too close to previously tested settings, where closeness (or mathematical proximity) is defined by a mathematical function dependent on the number of programming steps already taken.
3. Cannot have an amplitude that is 1.5 mA higher than the last setting tested.
4. If an adverse side effect is observed in previous programming steps, then all settings of higher amplitude and within ±0.3 of the contact location of the setting which caused the side effect are eliminated.

In some embodiments, the mathematical function used to determine closeness to previous determined settings may take into account a "geometry" associated with the stimulation parameter values formed by already viewed grid locations. For example, a next set of stimulation parameter values may be located in the center of this geometry.

Other embodiments may incorporate additional or different rules.

Next, the remaining possible sets of stimulation parameter values (e.g. remaining grid locations) are ranked. For example, in one embodiments, the sets of values are given three rankings according to the following criteria:
1. Rank by predicted therapeutic response, from best to worst.
2. Rank by total distance to already tested locations, from farthest to closest.
3. Rank by similarity in distances to already tested locations, from most similar to least similar.

The relative importance of these rankings may shift during a DBS programming session. In the beginning of the session, the goal is to explore the parameter space, so distance rankings are more important. Towards the end of a session, it may be necessary to pinpoint an optimal grid location, so the therapeutic response ranking may become more important. A mathematical function can be used to summarize the three rankings into one overall ranking according to how far the programming session has progressed. In other words, there may be a gradual decrease in the acceptance of a worse solution (unfavorable predicted therapeutic response) to allow for early exploration of the parameter space.

The logic can gradually be made more complex by adding more rankings. If there are two adverse symptoms to control, then the proposal phase can be adapted by adding a fourth ranking based on predictions for the second therapeutic response. In addition, in some embodiments an option can be added to allow external inputs to lock in the importance of the therapeutic response rankings, for scenarios where a clinician wishes to emphasize a particular response. Multiple predictions from different machine learning methods can also be incorporated into the proposal phase by adding more rankings. For each new feature added, fine-tuning of how the ranks come together and vary in importance during the programming session is specified.

When the number of stimulation parameters in a set is greater than 2, as is the case for directional leads, an exhaustive search through all the possible parameter sets (e.g., grid locations) becomes prohibitively slow. In one embodiment, the logic adapted such that only a subset of possible sets of stimulation parameter values (e.g., grid locations) is examined at each programming step. For example, in one example directional lead algorithm, the starting point is to determine an optimal grid location for the omnidirectional ring mode, which is equivalent to finding an optimal grid location in a 4-contact conventional lead. After the parameter space has been narrowed down to the vicinity of the best ring mode configuration, a 3-dimensional space around the lead can be constructed. The logic can then proceed to search in m=4 dimensions (x, y, z coordinates plus amplitude) in the same way that it searches in m=2 dimensions. A separate algorithm can convert the 3-dimensional location to stimulation settings.

Recognizing that the control logic can learn from previous programming sessions (for this patient or other patients, the logic can steer the search path towards parameter regions with a high density of prior optimal settings. By testing settings that have worked for other patients first, the clinician will likely need less programming steps to optimize therapeutic response. This logic may be incorporated into rules for proposing a next set of stimulation parameter values.

In block 806, the logic returns the proposed set of stimulation parameter values. As described with reference to FIG. 7, this revised set is then forward to the DBS and indications of new clinical results are received.

It will be understood that the system can include one or more of the methods described hereinabove with respect to FIGS. 7 and 8 in any combination. The methods, systems, and units described herein may be embodied in many different forms and should not be construed as limited to the embodiments set forth herein. Accordingly, the methods, systems, and units described herein may take the form of an entirely hardware embodiment, an entirely software embodiment or an embodiment combining software and hardware aspects. The methods described herein can be performed using any type of processor or any combination of processors where each processor performs at least part of the process.

It will be understood that each block of the flow diagram illustrations, and combinations of blocks in the flow diagram illustrations and methods disclosed herein, can be implemented by computer program instructions. These program instructions or code logic may be provided to a processor to produce a machine, such that the instructions, which execute on the processor, create means for implementing the actions specified in the flow diagram block or blocks disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

The above specification provides a description of the structure, manufacture, and use of the invention. Since many embodiments of the invention can be made without departing from the spirit and scope of the invention, the invention also resides in the claims hereinafter appended.

What is claimed as new and desired to be protected by Letters Patent of the United States is:

1. A system for facilitating programming settings of an implantable pulse generator associated with a patient, the system comprising:
    a processor;
    a memory; and
    control logic, stored in the memory, and configured, when executed by the processor, to perform actions comprising:
        a) automatically generating a proposed set of stimulation parameter values using one or more machine learning engines;
        b) receiving one or more clinical response values arising from testing of the proposed set of stimulation parameter values by stimulating the patient using the proposed set of stimulation parameter values;
        c) predicting one or more therapeutic response values for each of a plurality of sets of untested stimulation parameter values using the one or more machine learning engines and the one or more received clinical response values;
        d) selecting, based on at least the one or more predicted therapeutic response values, a revised proposed set of stimulation parameter values from the plurality of sets of untested stimulation parameter values;
        e) receiving one or more clinical response values arising from testing of the revised proposed set of stimulation parameter values by stimulating the patient using the revised proposed set of stimulation parameter values; and
        f) repeating actions c) to e) until a stop condition has been reached or the one or more received clinical response values indicates a value that corresponds to a therapeutic response indication within a designated tolerance.

2. The system of claim 1, wherein the selecting comprises selecting, based on at least the one or more predicted therapeutic response values and on a distance of each set of untested stimulation parameter values from one or more tested sets of stimulation parameter values, the revised proposed set of stimulation parameter values from the plurality of sets of untested stimulation parameter values.

3. The system of claim 1, wherein the system further comprises at least one sensor, wherein each instance of receiving one or more clinical response values comprises automatically receiving at least one of the one or more clinical response values from the at least one sensor.

4. The system of claim 1, wherein the automatically generating comprises using multiple machine learning techniques to automatically generate the proposed set of stimulation parameter values.

5. The system of claim 1, wherein the predicting comprises using multiple machine learning techniques to predict the one or more therapeutic response values.

6. The system of claim 1, wherein the predicting comprises using multiple machine learning engines to generate multiple predictions of each of the one or more predicted therapeutic response values.

7. The system of claim 1, wherein the selecting comprises selecting the revised proposed set of stimulation parameter values based upon one or more rules.

8. The system of claim 7, wherein the one or more rules includes at least one of: 1) a rule based upon retrying stimulation locations within a number of iterations; 2) a rule based upon mathematical proximity of the untested sets of stimulation parameter values to the sets of stimulation parameter values already tested; 3) a rule based upon values of a stimulation parameter leading to adverse side effects, or 4) a rule based upon a size of step between values of a same stimulation parameter.

9. The system of claim 1, wherein the selecting comprises selecting the revised proposed set of stimulation parameter values in each repetition of steps c) to e) in contact order, wherein contact order means testing along a first contact on a lead until side effects are prohibitive before testing a next contact on the lead.

10. The system of claim 1, the selecting comprises selecting the revised proposed set of stimulation parameter values in each repetition of steps c) to e) by selectively choosing contacts along a lead and varying other stimulation parameters for each selectively chosen contact.

11. The system of claim 1, wherein the selecting comprises selecting the revised proposed set of stimulation parameter values in each repetition of steps c) to e) randomly, based upon at least one of: a model of the patient, a spatial search algorithm, or by varying a distance to the revised proposed set of stimulation parameter values.

12. A computer-implemented method for automatically determining patient programming settings for an electrical stimulator, comprising:
    a) automatically generating a proposed set of stimulation parameter values using one or more machine learning engines;
    b) receiving one or more clinical response values arising from testing of the proposed set of stimulation parameter values by stimulating a patient using the proposed set of stimulation parameter values;
    c) predicting one or more therapeutic response values for each of a plurality of sets of untested stimulation parameter values using the one or more machine learning engines and the one or more received clinical response values;
    d) selecting, based on at least the one or more predicted therapeutic response values, a revised proposed set of stimulation parameter values from the plurality of sets of untested stimulation parameter values;
    e) receiving one or more clinical response values arising from testing of the revised proposed set of stimulation parameter values by stimulating the patient using the revised proposed set of stimulation parameter values; and
    f) repeating steps c) to e) until a stop condition has been reached or the one or more received clinical response values indicates a value that corresponds to a therapeutic response indication within a designated tolerance.

13. The method of claim 12, wherein automatically generating comprises automatically generating the proposed set of stimulation parameter values using a training data set based upon prior data for one or more subjects.

14. The method of claim 12, wherein the selecting comprises selecting, based on at least the one or more predicted therapeutic response values and on a distance of each set of untested stimulation parameter values from one or more tested sets of stimulation parameter values, the revised proposed set of stimulation parameter values from the plurality of sets of untested stimulation parameter values.

15. The method of claim 12, wherein the automatically generating comprises using multiple machine learning techniques to automatically generate the proposed set of stimulation parameter values.

16. The method of claim 12, wherein the predicting comprises using multiple machine learning techniques to predict the one or more therapeutic response values.

17. A computer-readable memory medium containing instructions that control a computer processor, when executed, to determine programming settings of an implantable pulse generator (IPG) associated with a patient by performing a method comprising:
   a) automatically generating a proposed set of stimulation parameter values using one or more machine learning engines;
   b) receiving one or more clinical response values arising from testing of the proposed set of stimulation parameter values by stimulating the patient using the proposed set of stimulation parameter values;
   c) predicting one or more therapeutic response values for each of a plurality of sets of untested stimulation parameter values using the one or more machine learning engines and the one or more received clinical response values;
   d) selecting, based on at least the one or more predicted therapeutic response values, a revised proposed set of stimulation parameter values from the plurality of sets of untested stimulation parameter values;
   e) receiving one or more clinical response values arising from testing of the revised proposed set of stimulation parameter values by stimulating the patient using the revised proposed set of stimulation parameter values; and
   f) repeating actions c) to e) until a stop condition has been reached or the one or more received clinical response values indicates a value that corresponds to a therapeutic response indication within a designated tolerance.

18. The computer-readable memory medium of claim 17, wherein the selecting comprises selecting, based on at least the one or more predicted therapeutic response values and on a distance of each set of untested stimulation parameter values from one or more tested sets of stimulation parameter values, the revised proposed set of stimulation parameter values from the plurality of sets of untested stimulation parameter values.

19. The computer-readable memory medium of claim 17, wherein the automatically generating comprises using multiple machine learning techniques to automatically generate the proposed set of stimulation parameter values.

20. The computer-readable memory medium of claim 17, wherein the predicting comprises using multiple machine learning techniques to predict the one or more therapeutic response values.

* * * * *